US005453414A

United States Patent [19]
Tice et al.

[11] Patent Number: 5,453,414
[45] Date of Patent: * Sep. 26, 1995

[54] 2-ARYLPYRIMIDINES AND HERBICIDAL USE THEREOF

[75] Inventors: Colin M. Tice, Philadelphia; Vincent A. Musco, Southampton; Renee C. Roemmele, Maple Glen; Harlow L. Warner, Hatboro, all of Pa.

[73] Assignee: Rohm and Haas Company, Philadelphia, Pa.

[*] Notice: The portion of the term of this patent subsequent to Apr. 5, 2011 has been disclaimed.

[21] Appl. No.: 185,579

[22] Filed: Jan. 18, 1994

Related U.S. Application Data

[63] Continuation-in-part of Ser. No. 62,802, May 20, 1993, Pat. No. 5,300,477.

[51] Int. Cl.$^6$ .......................... A01N 43/54; A01N 43/66; A01N 55/10
[52] U.S. Cl. .......................... 504/133; 504/134; 504/136; 504/193; 504/242
[58] Field of Search .................... 504/242, 243, 504/193, 136, 133

[56] References Cited

U.S. PATENT DOCUMENTS

| | | | |
|---|---|---|---|
| 4,431,440 | 2/1984 | Bhalla et al. | 544/289 |
| 4,771,040 | 9/1988 | Maurer et al. | 514/86 |
| 4,908,379 | 3/1990 | Nakajima et al. | 514/274 |
| 5,300,477 | 4/1994 | Tice | 504/242 |

FOREIGN PATENT DOCUMENTS

| | | |
|---|---|---|
| 339105 | 11/1989 | European Pat. Off. |
| 243496 | 3/1987 | Germany |

OTHER PUBLICATIONS

Kronberg, L. et al. Acta. Pharm. Suecica, pp. 37–46, 1970.
Kronberg, L. et al. Acta. Pharm. Suecica, pp. 489–500, 1969.
Staskun, B. et al. J. Chem. Soc. 4708–4710, 1956.
Hirokami, S. et al. J. OrganChem., 2455–2468, 1987.
Heinz, P. et al. Z. Chem., 336, 1968.
Mussetta, M. T., et al. C. R. Acad. Sci. Ser. C. 1341–1344, 1973.
Harris, R. L. N. et al. Angew. Chem. Int. Ed(Engl), pp. 779–780, 1977.
Nishio, T. et al. J. Chem. Soc Perkin, pp. 2523–2529, 1987.
Oostveen, E. A. et al. Recl. Trav. Chim. Pays–Bas, pp. 68–72, 1977.
Culbertson, T. B. J. Heterocycl. Chem., pp. 1423–1424, 1979.
Botta, M. et al. Arch Pharm. (Weinheim), pp. 203–207, 1991.
Briel, D. et al. Arch Pharm. (Weinheim), pp. 1145–1147, 1985.
Juby, P. F. et al. J. Med. Chem., pp. 263–269, 1979.
Gupta, K. A. et al. Synthesis, pp. 905–907, 1981.

*Primary Examiner*—Peter O'Sullivan
*Assistant Examiner*—B. Bembenick
*Attorney, Agent, or Firm*—Clark R. Carpenter

[57] ABSTRACT

A class of 2-arylpyrimidines which is useful in the control of weeds of the general formula:

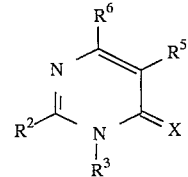

wherein $R^2$ is an optionally substituted aromatic ring; $R^3$ is a saturated or unsaturated alkyl group; $R^5$ is selected from acyl, alkoxyalkyl, alkoxyimino, dialkoxyalkyl, formyl, hydroxyalkyl, and hydroxyimino; $R^6$ is selected from hydrogen, halo, alkyl, haloalkyl, aryl, and alkoxy; and X is oxygen or sulfur.

3 Claims, No Drawings

2-ARYLPYRIMIDINES AND HERBICIDAL USE THEREOF

This application is a continuation-in-part of application Ser. No. 08/062,802 filed May 20, 1993, now U.S. Pat. No. 5,300,477.

BACKGROUND OF THE INVENTION

A need continues for novel and improved herbicidal compounds and compositions. This is particularly so since the targets of herbicides can become resistant to known herbicides over time and after use of such compositions. Additionally, economic and environmental considerations can favor herbicides having different modes of performance than those currently used. This invention relates to novel arylpyrimidines and their use as broad spectrum herbicides.

SUMMARY OF THE INVENTION

2-Arylpyrimidines which are useful in the control of weeds have been discovered. These compounds are of the general formula:

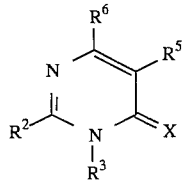

wherein $R^2$ is a substituted or unsubstituted aryl or heteroaromatic group; $R^3$ is an alkyl, haloalkyl, polyhaloalkyl, alkenyl, haloalkenyl, polyhaloalkenyl, alkynyl, haloalkynyl, polyhaloalkynyl, alkenynyl, alkoxyalkyl, dialkoxyalkyl, haloalkoxyalkyl, oxoalkyl, trimethylsilylalkynyl, cyanoalkyl or aryl group; $R^5$ is a hydrogen, halo, acyl, alkyl, alkenyl, alkynyl, alkoxy, alkylthio, alkoxyalkyl, alkoxyimino, alkoxycarbonylalkyl, dialkoxyalkyl, formyl, haloalkyl, haloalkenyl, haloalkynyl, haloalkoxy, hydroxyalkyl, hydroxyimino, polyhaloalkyl, polyhaloalkenyl, polyhaloalkynyl, polyhaloalkoxy, trimethylsilylalkynyl, or cyano group; and $R^6$ is a hydrogen, halo, alkyl, alkenyl, alkynyl, alkoxy, alkylthio, haloalkylthio, alkoxyalkyl, alkoxycarbonyl, alkoxycarbonylalkyl, haloalkyl, haloalkoxy, haloalkenyl, haloalkynyl, polyhaloalkyl, polyhaloalkoxy, polyhaloalkylthio, polyhaloalkenyl, polyhaloalkynyl, cycloalkyl, aryl, aryloxy, heterocyclyl, aralkyl, alkylamino, dialkylamino, dialkylaminocarbonyl, or cyano group; and X is oxygen or sulfur. It is to be understood that the prefix term "halo" designates a halogen substituent (such as fluorine, chlorine, bromine, or iodine) and that "polyhalo" designates two or more substituents independently selected halogens. It is further to be understood that, unless otherwise specified, use of the prefix "halo" without a concurrent use of the prefix "polyhalo" is not intended to limit the invention to singularly halogenated compounds. This invention also teaches methods of preparing these compounds as well as methods of using the compounds as herbicides.

EMBODIMENTS OF THE INVENTION

Embodiments of the present invention are described in the following compound embodiments, methods of preparation, methods of use and compositions (formulations). While the invention is exemplified in these descriptions, such are not intended to limit the scope of the invention.

Compound Embodiments

An embodiment of the present invention are compounds of the general formula:

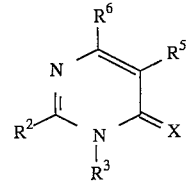

wherein $R^2$ is a substituted or unsubstituted aryl group (e.g. aromatic ring structure having six to ten carbon atoms) or a substituted or unsubstituted heteroaromatic group (e.g. a heteroaromatic ring structure having four to five carbon atoms and one heteroatom selected from the group consisting of nitrogen, sulfur and oxygen); $R^3$ is an alkyl, haloalkyl, polyhaloalkyl, haloalkenyl, polyhaloalkenyl, alkenyl, alkynyl, haloalkynyl, polyhaloalkynyl, alkenynyl, alkoxyalkyl, dialkoxyalkyl, haloalkoxyalkyl, oxoalkyl, trimethylsilylalkynyl, cyanoalkyl or aryl group; $R^5$ is a hydrogen, halo, acyl, alkyl, alkenyl, alkynyl, alkoxy, alkylthio, alkoxyalkyl, alkoxyimino, alkoxycarbonylalkyl, dialkoxyalkyl, formyl, haloalkyl, haloalkenyl, haloalkynyl, haloalkoxy, hydroxyalkyl, hydroxyimino, polyhaloalkyl, polyhaloalkenyl, polyhaloalkynyl, polyhaloalkoxy, trimethylsilylalkynyl, or cyano group; and $R^6$ is a hydrogen, halo, alkyl, alkenyl, alkynyl, alkoxy, alkylthio, alkoxyalkyl, alkoxycarbonyl, alkoxycarbonylalkyl, haloalkyl, haloalkenyl, haloalkynyl, haloalkoxy, haloalkylthio, polyhaloalkyl, polyhaloalkenyl, polyhaloalkynyl, polyhaloalkoxy, polyhaloalkylthio, cycloalkyl, aryl, aryloxy, heterocyclyl, aralkyl, alkylamino, dialkylamino, dialkylaminocarbonyl, or cyano group; and X is oxygen or sulfur.

$R^2$ is an aryl or heteroaromatic group, preferably furyl, phenyl, naphthyl, pyridyl, or thienyl, and may be optionally substituted with up to three substituents independently selected from bromo; chloro; fluoro; $(C_1-C_{12})$alkyl, preferably $(C_1-C_6)$alkyl; cyclo$(C_3-C_8)$alkyl, preferably cyclo$(C_5-C_6)$alkyl; $(C_2-C_{12})$alkenyl, preferably $(C_2-C_6)$alkenyl; cyclo$(C_3-C_8)$alkenyl; $(C_2-C_{12})$alkynyl, preferably $(C_2-C_6)$alkynyl; halo$(C_1-C_{12})$alkyl, preferably halo$(C_1-C_6)$alkyl; polyhalo$(C_1-C12)$alkyl, preferably polyhalo$(C_1-C_6)$alkyl; halo$(C_2-C_{12})$alkenyl, preferably halo$(C_2-C_6)$alkenyl; polyhalo$(C_2-C_{12})$alkenyl, preferably polyhalo$(C_2-C_6)$alkenyl; halo$(C_2-C_6)$alkynyl; polyhalo$(C_2-C_6)$alkynyl; $(C_1-C_{12})$alkoxy, preferably $(C_1-C_6)$alkoxy; $(C_1-C_{12})$alkylthio, preferably $(C_1-C_6)$alkylthio; $(C_1-C_{12})$alkylsulfonyl; $(C_1-C_{12})$alkylsulfinyl; phenyl; phen$(C_1-C_{12})$alkyl; phen$(C_2-C_{12})$alkenyl; phen$(C_2-C_{12})$alkynyl; cyano; halo$(C_1-C_{12})$alkoxy, preferably halo$(C_1-C_6)$alkoxy; 1,3-dioxalan-2-yl; hydroxyimino, polyhalo$(C_1-C_{12})$alkoxy,; and nitro. Substituent groups can be branched or unbranched. Preferred phenyl groups are phenyl, 3-methylphenyl, 3-methoxyphenyl, 3-nitrophenyl, 4-fluorophenyl, 4-chlorophenyl, 3-trifluoromethylphenyl, 3-bromophenyl, 3-chlorophenyl, 3-fluorophenyl, 3-trifluoromethoxyphenyl, 3-cyanophenyl, 3-(1,3-dioxolan-2-yl)phenyl, 3-(hydroxyimino)phenyl, 2-fluorophenyl, 2-chlorophenyl, 2-trifluoromethoxyphenyl, 3,5-difluorophenyl, 3,5-dichlorophenyl, 2,4-difluorophenyl, 2,5-difluorophenyl, 3-chloro-4-fluorophenyl, 3,4-difluorophenyl, 3-fluoro-5-trifluoromethylphenyl, 3,4,5-trifluorophenyl; more preferably phenyl, 3-fluorophenyl, and 3-chlorophenyl. Preferred pyridyl groups are 6-chloro-2-pyridyl; 3-pyridyl; 1-methyl-3-pyridinium; 5-bromo-3-pyridyl; 5,6-dichloro-3-pyridyl;

5-chloro-3-pyridyl, 1-oxo-3-pyridyl; 4-pyridyl; 2-fluoro-4-pyridyl; 2-chloro- 4-pyridyl; 2 -chloro-6-methyl-4-pyridyl; 2-methyl-4-pyridyl, 2-methoxy-4-pyridyl, 2-cyano-4-pyridyl, 1-oxo-4-pyridyl, 2,6-difluoro-4-pyridyl and 2,6-dichloro-4-pyridyl. More preferred are 2-chloro-4-pyridyl; 2-fluoro-4-pyridyl; and 2,6-dichloro-4-pyridyl. The pyridyl groups can also be present as a salt, such as 1-methyl-3-pyridinium iodide or 3-pyridinium hydrochloride. Preferred furyl groups are 2-furyl and 3-furyl. A preferred naphthyl group is 2-naphthyl. Preferred thienyl groups are 2-thienyl, 3-thienyl, 4-chloro-2 -thienyl, 5-chloro-2-thienyl, 5-chloro-3-thienyl and 2,5-dichloro-3-thienyl.

In the case of $R^2$ being a pyridyl group, an additional selection of substituent groups is oxygen substituted on the nitrogen atom of the pyridyl ring; e.g. N-oxo groups, such as 1-oxo-3-pyridyl or 1-oxo-4-pyridyl. Optionally, each of the furyl, phenyl, naphthyl, pyridyl and thienyl groups can have a fused ring moiety such that the fused ring is composed of alkylenedioxy, e.g. an oxymethyleneoxy (—O—$CH_2$—O—) link or an oxyethyleneoxy (—O—$CH_2CH_2$—O—) link which is bonded to adjacent carbon atoms of the group. For example, 3,4-methylenedioxyphenyl.

$R^3$ is an alkyl, alkenyl, alkynyl, alkenynyl, alkoxyalkyl, dialkoxyalkyl, haloalkoxyalkyl, oxoalkyl, trimethylsilylalkynyl, cyanoalkyl or aryl group. Preferably, $R^3$ is a ($C_1$-$C_3$)alkyl; ($C_3$-$C_4$)alkenyl; or ($C_3$-$C_6$)alkynyl group, each of which may be optionally substituted with up to five halogens; or a ($C_1$-$C_6$)alkoxy($C_1$ -$C_6$)alkyl, di($C_1$-$C_6$)alkoxy($C_1$-$C_6$)alkyl, halo($C_1$-$C_6$)alkoxy($C_1$-$C_6$)alkyl, 2-oxo($C_2$-$C_3$)alkyl trimethylsilyl($C_3$-$C_4$)alkynyl or cyano($C_1$-$C_6$)alkyl group. A preferred ($C_1$-$C_3$)alkyl group is ethyl. Preferred alkenyl and halogen substituted alkenyl groups are ($C_3$-$C_4$)alkenyls, such as allyl and 3-chloroallyl. Preferred alkynyl groups are ($C_3$-$C_6$)alkynyl, such as pentynyl, propynyl and butynyl, more preferably pent-2-ynyl, prop-2-ynyl, and but-2-ynyl. Preferred halogen substituted ($C_3$-$C_6$)alkynyl groups are iodopropargyl and bromopropargyl. Preferred ($C_1$-$C_6$)alkoxy($C_1$-$C_6$)alkyls are ($C_1$-$C_2$)alkoxy($C_1$-$C_3$)alkyl, more preferably methoxymethyl and 2-methoxyethyl, and most preferably methoxymethyl. Preferred di($C_1$-$C_6$)alkoxy($C_1$-$C_6$)alkyls are di($C_1$-$C_2$)alkoxy($C_1$-$C_3$)alkyls, more preferably 2,2-dimethoxypropyl. A preferred 2-oxo($C_2$-$C_3$)alkyl is acetonyl. A preferred trimethylsilyl ($C_3$-$C_4$)alkynyl is 3-(trimethylsilyl)propargyl. A preferred cyano ($C_1$-$C_6$)alkyl is cyanomethyl. Preferred alkenynyls are ($C_5$-$C_6$)alkenynyls, more preferably pent-4-en-2-ynyl.

$R^5$ is a hydrogen, halo, acyl, alkyl, alkenyl, alkynyl, alkoxy, alkylthio, alkoxyalkyl, alkoxyimino, alkoxycarbonylalkyl, dialkoxyalkyl, formyl, haloalkyl, haloalkenyl, haloalkynyl, haloalkoxy, hydroxyalkyl, hydroxyimino, polyhaloalkyl, polyhaloalkenyl, polyhaloalkynyl, polyhaloalkoxy, trimethylsilylalkynyl or cyano group. Preferred $R^5$ substituents are hydrogen, ($C_1$-$C_6$)acyl, ($C_1$-$C_5$)alkyl, ($C_3$-$C_6$)alkenyl, ($C_2$-$C_6$)alkynyl, trimethylsilyl($C_2$-$C_3$)alkynyl, ($C_1$-$C_6$)alkoxy, ($C_1$ -$C_6$)alkoxy($C_1$-$C_6$)alkyl, di($C_1$-$C_6$)alkoxy($C_1$-$C_6$)alkyl, formyl, ($C_1$-$C_6$)alkoxyimino, halo- or polyhalo($C_1$-$C_6$)alkyl, halo- or polyhalo($C_2$-$C_6$)alkenyl, halo- or polyhalo($C_2$-$C_6$)alkynyl, halo ($C_1$-$C_6$)alkoxy, polyhalo ($C_1$-$C_6$)alkoxy, hydroxy($C_1$-$C_6$)alkyl, hydroxyimino, ($C_1$-$C_3$)alkoxycarbonyl($C_1$-$C_3$)alkyl, ($C_1$-$C_6$)alkylthio, halo and cyano. Preferred ($C_1$-$C_5$)alkyls are methyl, ethyl, n-propyl and iso-propyl, more preferably methyl and ethyl. Preferred ($C_1$-$C_6$)acyls are ($C_1$-$C_3$)acyl. Preferred ($C_2$-$C_6$)alkynyls are ($C_2$-$C_4$)alkynyls, more preferably prop-2-ynyl. Preferred ($C_1$-$C_6$)alkoxys are ($C_1$ -$C_2$)alkoxys, more preferably methoxy. Preferred ($C_1$-$C_6$)alkylthios are ($C_1$-$C_2$)alkylthios, more preferably methylthio. A preferred alkoxycarbonyalkyl is methoxycarbonylmethyl. Preferred ($C_3$-$C_6$)alkenyls are ($C_3$-$C_4$)alkenyl, more preferably allyl. Preferred ($C_1$-$C_6$)alkoxy($C_1$-$C_6$)alkyls are ($C_1$-$C_2$)alkoxy($C_1$-$C_3$)alkyl, more preferably methoxymethyl and 2-methoxyethyl, and most preferably methoxymethyl. Preferred ($C_1$-$C_6$)alkoxyiminos are ($C_1$-$C_3$)alkoxyimino, more preferably methoxyimino. Preferred di($C_1$-$C_6$)alkoxy($C_1$-$C_6$)alkyls are di($C_1$-$C_2$)alkoxy($C_1$-$C_3$)alkyls, more preferably 1,3dioxalan-2-yl. Preferred halo($C_1$-$C_6$)alk and polyhalo($C_1$-$C_6$)alkyls are halo($C_1$-$C_2$)alkyls and polyhalo($C_1$-$C_2$)alkyls, more preferably fluoromethyl, difluoromethyl, and trifluoromethyl. Preferred halo($C_1$-$C_6$)alkoxys and polyhalo($C_1$-$C_6$)alkoxys are halo($C_1$-$C_2$)alkoxys, and polyhalo($C_1$-$C_2$)alkoxys more preferably difluoromethoxy and trifluoromethoxy. Preferred hydroxy($C_1$-$C_6$)alkyls are hydroxy($C_1$-$C_3$)alkyls, more preferably hydroxymethyl. Preferred halos are chloro and fluoro. A preferred trimethylsilyl($C_2$-$C_3$)alkynyl is trimethylsilylethynyl.

$R^6$ is a hydrogen, halo, alkyl, alkenyl, alkynyl, alkoxy, alkylthio, alkoxyalkyl, alkoxycarbonyl, alkoxycarbonylalkyl, haloalkyl, polyhaloalkyl, cycloalkyl, haloalkylthio, haloalkenyl, polyhaloalkenyl, haloalkynyl, polyhaloalkynyl, haloalkoxy, polyhaloalkoxy, polyhaloalkylthio, aryl, aryloxy, heterocyclyl selected from furyl, pyridyl and thienyl, aralkyl, alkylamino, dialkylamino, dialkylaminocarbonyl, or cyano group. Preferred $R^6$ are hydrogen, halo, straight ($C_1$-$C_8$)alkyl, branched ($C_3$-$C_8$)alkyl, ($C_2$-$C_6$)alkenyl, ($C_2$-$C_6$)alkynyl, halo($C_1$-$C_6$)alkyl or polyhalo($C_1$-$C_6$)alkyl, halo($C_2$-$C_6$)alkenyl or polyhalo($C_2$-$C_6$)alkenyl, halo($C_2$-$C_6$)alkynyl or polyhalo($C_2$-$C_6$)alkynyl, ($C_1$-$C_6$)alkoxy($C_1$-$C_4$)alkyl, ($C_1$-$C_6$)alkoxy, ($C_1$-$C_6$)alkylthio, ($C_1$-$C_3$)alkoxycarbonyl, ($C_1$-$C_3$)alkoxycarbonyl($C_1$ -$C_3$)alkyl, substituted or unsubstituted ($C_6$-$C_{10}$)aryl, substituted or unsubstituted ($C_6$-$C_{10}$)aryloxys, substituted or unsubstituted ar($C_1$-$C_4$)alkyl, cyclo($C_3$-$C_7$)alkyl, halo($C_1$ -$C_6$)alkylthio, polyhalo ($C_1$-$C_6$)alkythio, halo($C_1$-$C_6$)alkoxy, polyhalo ($C_1$-$C_6$)alkoxy, ($C_4$ -$C_5$)heterocyclyl, ($C_1$-$C_3$)alkylamino, di($C_1$-$C_3$)alkylamino, di($C_1$-$C_3$)alkylaminocarbonyl, and cyano. The aryl portion of the foregoing ($C_6$-$C_{10}$)aryl, ($C_6$-$C_{10}$)aryloxy and aryl($C_1$-$C_4$)alkyl groups can be optionally substituted with up to three substituents independently selected from bromo; chloro; fluoro; ($C_1$-$C_{12}$)alkyl, preferably ($C_1$-$C_6$)alkyl; cyclo($C_3$-$C_8$)alkyl, preferably cyclo($C_5$-$C_6$)alkyl; ($C_2$-$C_{12}$)alkenyl, preferably ($C_2$-$C_6$)alkenyl; cyclo($C_3$-$C_8$)alkenyl; ($C_2$-$C_{12}$)alkynyl, preferably ($C_2$-$C_6$)alkynyl; halo($C_1$-$C_{12}$)alkyl, preferably halo($C_1$-$C_6$)alkyl; polyhalo($C_1$ -$C_{12}$)alkyl, preferably polyhalo($C_1$-$C_6$)alkyl; halo($C_2$-$C_{12}$)alkenyl, preferably halo($C_2$ -$C_6$)alkenyl; polyhalo($C_2$-$C_{12}$)alkenyl, preferably polyhalo($C_2$-$C_6$)alkenyl; halo($C_2$ -$C_6$)alkynyl; polyhalo($C_2$-$C_6$)alkynyl; ($C_1$-$C_{12}$)alkoxy, preferably ($C_1$-$C_6$)alkoxy; ($C_1$ $C_{12}$)alkylthio, preferably ($C_1$-$C_6$)alkylthio; ($C_1$-$C_{12}$)alkylsulfonyl; ($C_1$-$C_{12}$)alkylsulfinyl; phenyl; phen($C_1$-$C_{12}$)alkyl; phen($C_2$-$C_{12}$)alkenyl; phen($C_2$-$C_{12}$)alkynyl; cyano; halo($C_1$ -$C_{12}$)alkoxy, preferably halo($C_1$-$C_6$)alkoxy; 1,3-dioxalan-2-yl; hydroxyimino; and nitro. Preferred ($C_1$-$C_8$)alkyls are straight ($C_1$-$C_7$)alkyls and branched ($C_3$-$C_8$)alkyls, preferably methyl, ethyl, n-propyl, n-butyl, n-pentyl, n-hexyl, n-heptyl, s-butyl, i-propyl, i-butyl and t-butyl; more preferably methyl, ethyl, n-propyl, s-butyl, i-propyl and t-butyl. A preferred ($C_2$-$C_6$)alkenyl is 2-methyl-1-propenyl. A preferred ($C_6$ -$C_{10}$)aryl is phenyl. A preferred ($C_6$-$C_{10}$)aryloxy is phenoxy. Preferred ($C_4$-$C_5$)heterocyclyls are 3-thienyl, 3-furyl, 2-thienyl and 4-pyridyl; most preferably 3 -thienyl. Preferred ($C_1$-$C_6$)alkoxys are ($C_1$-C5)alkoxys, more preferably methoxy and ethoxy. A preferred ($C_1$-

$C_3$)alkoxycarbonyl is ethoxycarbonyl. Preferred ($C_2$-$C_6$)alkynyls are but-2-ynyl, but-3-ynyl, and prop-2-ynyl. Preferred halos are fluoro, bromo, and chloro; more preferably chloro and bromo. Preferred halo($C_1$-$C_6$)alkyls and polyhalo($C_1$-$C_6$)alkyls are halo($C_1$-$C_3$)alkyls and polyhalo($C_1$-$C_3$)alkyls, more preferably trifluoromethyl, pentafluoroethyl, trichloromethyl, bromomethyl, chloromethyl, difluoromethyl, and chlorodifluoromethyl; most preferably trifluoromethyl. Preferred halo($C_1$-$C_6$)alkoxys and polyhalo($C_1$-$C_6$)alkoxys are halo($C_1$-$C_3$)alkoxys and polyhalo($C_1$-$C_3$)alkoxys, more preferably difluoromethoxy and trifluoromethoxy. Preferred ($C_1$-$C_6$)alkylthios are ($C_1$-$C_5$)alkylthios, more preferably methylthio. A preferred ($C_1$-$C_6$)alkoxy($C_1$-$C_4$)alkyl is methoxymethyl. A preferred ar($C_1$-$C_4$)alkyl is benzyl. Preferred cyclo($C_3$-$C_7$)alkyls are cyclopropyl, cyclobutyl and cyclopentyl. A preferred di($C_1$-$C_3$)alkylamino is dimethylamino. A preferred di($C_1$-$C_3$)alkylaminocarbonyl is dimethylaminocarbonyl.

X is oxygen or sulfur, preferably oxygen.

A preferred embodiment of this invention are the compounds represented by formula I wherein X is oxygen and $R^2$ is substituted or unsubstituted phenyl, pyridyl, or thienyl.

A more preferred embodiment of this invention are the compounds represented by formula I wherein X is oxygen; $R^2$ is substituted or unsubstituted phenyl, substituted or unsubstituted pyridyl or substituted or unsubstituted thienyl; and $R^3$ is ($C_3$-$C_6$)alkynyl.

A still more preferred embodiment of this invention is the compound represented by formula I wherein X is oxygen; $R^2$ is substituted or unsubstituted phenyl, substituted or unsubstituted pyridyl or substituted or unsubstituted thienyl; $R^3$ is ($C_3$-$C_6$)alkynyl; and $R^5$ and $R^6$ are independently selected from hydrogen, halo, ($C_1$-$C_4$)alkyl, polyhalo($C_1$-$C_4$)alkyl, and ($C_1$-$C_4$)alkoxy. $R^6$ can be also unsubstituted or substituted phenyl. $R^5$ can also be ($C_1$-$C_4$)acyl, ($C_1$-$C_4$)alkoxy($C_1$-$C_4$)alkyl, ($C_1$-$C_4$)alkoxyimino, di($C_1$-$C_4$)alkoxy($C_1$-$C_4$)alkyl, hydroxy($C_1$-$C_4$)alkyl, hydroxyimino, or formyl.

Even more preferred is the compound represented by formula I wherein X is oxygen; $R^2$ is phenyl, 3-substituted phenyl (i.e. meta-substituted phenyl), 3,5-disubstituted-phenyl or 3,4,5-trisubstituted phenyl, 2-substituted-4-pyridyl or 2,6-disubstituted-4-pyridyl or 3-thienyl or 5-substituted-3-thienyl; $R^3$ is ($C_3$-$C_6$)alkynyl; and $R^5$ and $R^6$ are independently selected from hydrogen, halo, ($C_1$-$C_4$)alkyl, polyhalo($C_1$-$C_4$)alkyl and ($C_1$-$C_4$)alkoxy. $R^6$ can be also unsubstituted or substituted phenyl. $R^5$ can also be ($C_1$-$C_4$)acyl, ($C_1$-$C_4$)alkoxy($C_1$-$C_4$)alkyl, ($C_1$-$C_4$)alkoxyimino, di($C_1$-$C_4$)alkoxy($C_1$-$C_4$)alkyl, hydroxy($C_1$-$C_4$)alkyl, hydroxyimino, or formyl.

A yet more preferred embodiment of this invention is the compound represented by formula I wherein X is oxygen; $R^2$ is phenyl, 3-fluorophenyl, 3-chlorophenyl, 3,5-difluorophenyl, 3,5-dichlorophenyl, 3,4,5-trifluorophenyl, 2-chloro-4-pyridyl, 2-fluoro-4-pyridyl, 2,6-dichloro-4-pyridyl or 3-thienyl or 5-chloro-3-thienyl; $R^3$ is propargyl; $R^5$ is hydrogen, methyl, ethyl, methoxy, hydroxymethyl, formyl, fluoro or chloro; and $R^6$ is methyl, ethyl, isopropyl, n-propyl, n-butyl, s-butyl, i-butyl, t-butyl, trifluoromethyl, difluoromethyl, phenyl, chloro, bromo, or fluoro.

Preferred compounds are (a) 5,6-diethyl-2-phenyl-3-propargyl-4(3H)-pyrimidinone;

(b) 5-ethyl-2-phenyl-3-propargyl-6-trifluoromethyl-4(3H)-pyrimidinone;

(c) 5-ethyl-6-(1-methylethyl)-2-phenyl-3-propargyl-4(3H)-pyrimidinone;

(d) 6-chloro-5-ethyl-2-phenyl-3-propargyl-4(3H)-pyrimidinone;

(e) 5,6-diethyl-2-(3-fluorophenyl)-3-propargyl-4(3H)-pyrimidinone;

(f) 2-(2,6-dichloro-4-pyridyl)-5,6-diethyl-3-propargyl-4(3H)-pyrimidinone;

(g) 5,6-diethyl-2-(3,5-difluorophenyl)-3-propargyl-4(3H)-pyrimidinone;

(h) 5-ethyl-2-phenyl-3-propargyl-6-propyl-4(3H)-pyrimidinone.

(i) 6-difluoromethyl-5-ethyl-2-phenyl-3-propargyl-4(3H)-pyrimidinone; or (j) 6-ethyl-5-methoxy-2-phenyl-3-propargyl-4(3H)- pyrimidinone.

Compounds encompassed by the present invention include, but are not limited to, those illustrated in Table 1. The synthesis methods (i.e., "A", "B" etc.) specified in the table are described hereinafter in this specification. The sequence of letters in the "Synthesis" column indicated the relative sequence of steps performed. For instance, "D+A" indicates the steps of procedure D were first performed, followed by the steps of Procedure A.

TABLE 1

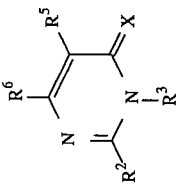

For the below table, "Me" is methyl, "Et" is ethyl, "Pr" is propyl, "Bu" is butyl, "Pe" is pentyl, "Bn" is benzyl, and "Ph" is phenyl; and except as noted, X = O (oxygen).

| Compound No. | $R^2$ | $R^3$ | $R^5$ | $R^6$ | MP °C. | Synthesis |
|---|---|---|---|---|---|---|
| 1 | —Ph | —CH$_2$CCH | —Me | —Me | 125–128 | D + A |
| 2 | —Ph | —CH$_2$CCH | —H | —Me | 148–149 | D + A |
| 4 | —Ph | —CH$_2$CCH | —H | —CF$_3$ | 118–120 | D + A |
| 5 | —Ph | —CH$_2$CCH | —Me | —Et | 115–117 | D + A |
| 6 | —Ph | —CH$_2$OCH$_3$ | —H | —CF$_3$ | 89–90 | D + Z6 |
| 7 | —Ph | —CH$_2$CCH | —Br | —CF$_3$ | 156–160 | D + Y1 + A |
| 8 | —Ph | —CH$_2$CCH | —Me | —Ph | 170–173 | D + A |
| 9 | —Ph | —CH$_2$CCH | —Cl | —Me | 131–134 | D + A |
| 11 | —Ph | —CH$_2$CCH | —H | -t-C$_4$H$_9$ | Oil | D + A |
| 12 | —Ph | —CH$_2$CCH | -i-Pr | —Pr | 72.5–74 | D + A |
| 13 | —Ph | —CH$_2$CCH | —Et | —Me | 79–80.5 | D + A |
| 14 | —Ph | —CH$_2$CCH | —Me | —Me | 103–106 | D + A |
| 15 | —Ph | —Et | —Me | —Me | 77–78 | D + A |
| 16 | —Ph | —CH$_2$CCH | —Me | —Cl | 137.5–139 | E + H + I + A |
| 17 | —Ph | —CH$_2$CCH | -n-Pe | —Me | 92–93.5 | D + A |
| 18 | —Ph | —CH$_2$CHCH$_2$ | —H | —CF$_3$ | Oil | D + A |
| 19 | —Ph | —CH$_2$CCH | —Me | —C(O)NMe$_2$ | 137–140 | D + A + Z1 |
| 20 | —Ph | —Et | —H | —CF$_3$ | Solid | B |
| 21 | —Ph | —CH$_2$CCCH$_2$CH$_3$ | —Et | —CF$_3$ | 99–100.5 | D + A |
| 22 | —Ph | —CH$_2$CCH | —Et | —Et | 101–103 | D + A |
| 23 | —Ph | —CH$_2$CCH | —Me | —NMe$_2$ | 111.5–113.5 | E + H + I + A + Z2 |
| 25 | —Ph | —CH$_2$C(O)Me | —Me | —C$_2$H$_5$ | 87–89 | D + Z3 |
| 26 | —Ph | —CH$_2$CCH | —H | —SMe | 156–159 | E + H + I + A + Z4 |
| 27 | —Ph | —CH$_2$CCH | —Et | —C$_2$F$_5$ | 134–136 | D + A |
| 28 | —Ph | —CH$_2$CCH | —Me | —Ph | 124–126 | D + A |
| 29 | —Ph | —CH$_2$CCH | -n-Pr | —CF$_3$ | 143–145 | D + A |
| 30 | —Ph | —CH$_2$CCH | —OMe | —CF$_3$ | 155–157 | D + A |
| 31 | —Ph | —CH$_2$CCH | —H | —CF$_3$ | 103–106 | D + A |
| 32 | —Ph | —CH$_2$CCH | —H | —C$_2$H$_5$ | 101–103 | D + A |
| 33 | —Ph | —CH$_2$CCH | —Me | —CH$_2$OMe | 125–127 | D + A |
| 35 | 4-ClPh | —CH$_2$CCH | —Me | —Et | 109–111 | D + A |
| 36 | —Ph | —CH$_2$C(OMe)$_2$Me | —Me | —Et | 85–88 | D + A + Z5 |
| 37 | —Ph | —CH$_2$CH$_2$OMe | —H | —CF$_3$ | 49–51 | B |
| 38 | —Ph | —CH$_2$CCH | —CN | —SMe | 189–191 | A |
| 39 | —Ph | —CH$_2$CCCH$_3$ | —H | —CF$_3$ | 85–88 | D + A |

TABLE 1-continued

| | | | | |
|---|---|---|---|---|
| 40 | —Ph | —CH₂CCH | —F | —Cl | 113–115 | D + H + I + A |
| 41 | —Ph | —Ph | —H | —CF₃ | 149–151 | B |
| 45 | —Ph | —CH₂CCH | —H | —CCl₃ | 86–91 | D + A |
| 46 | —Ph | —CH₂CCH | —Et | —CF₃ | 113–115 | BorD + A |
| 47 | —Ph | —CH₂CCH | —SMe | —CF₃ | 159–162 | D + A |
| 48 | —Ph | —CH₂CCH | —Me | i-Pr | 120–122 | D + A |
| 51 | —Ph | —CH₂CCH | —Me | —H | 135–136 | D + A |
| 52 | —Ph | —CH₂CCH | —Me | —CO₂Et | 147–150 | D + A |
| 53 | —Ph | —CH₂CHCH₂ | | —CF₃ | 73–76 | B |
| 54 | -2-Cl-4-pyridyl | —CH₂CCH | —Et | n-Bu | 82–84 | B |
| 55 | —Ph | —CH₂CCH | —Et | —CF₃ | 57–59 | D + A |
| 56 | -2-Cl-4-pyridyl | —CH₂CCH | —Et | —Et | 84–86 | D + A |
| 57 | -3,5-diClPh | —CH₂CCH | —Et | —Et | 113–114 | B |
| 58 | -4-pyridyl | —CH₂CCH | —Et | —CF₃ | 114–116 | D + A |
| 59 | -2-Cl-6-Me-4-pyridyl | —CH₂CCH | —Et | —Et | 119–121 | B |
| 60 | -3-pyridyl | —CH₂CCH | —Et | —CF₃ | 116–118 | D + A |
| 61 | -1-Me-3-pyridinium iodide | —CH₂CCH | —Et | —CF₃ | >170(dec) | B + Zl3 |
| 62 | -2-F-4-pyridyl | —CH₂CCH | —Et | —CF₃ | Oil | B |
| 63 | -5,6-diCl-3-pyridyl | —CH₂CCH | —Et | —CF₃ | 89–92 | D + A |
| 64 | -3,4-diFPh | —CH₂CCH | —Et | —Et | 97–99 | B |
| 65 | -2,6-diCl-4-pyridyl | —CH₂CCH | —Et | —CF₃ | 129–131 | B |
| 66 | -5-Br-3-pyridyl | —CH₂CCH | —Et | —CF₃ | 123–125 | B |
| 67 | -2,6-diCl-4-pyridyl | —CH₂CCH | —Et | i-Pr | solid | A |
| 68 | -4-FPh | —CH₂CCH | —Et | —Et | 107–109 | D + A |
| 69 | -3-formylPh | —CH₂CCH | —Cl | —Et | 82–86 | D + A + Z14 |
| 70 | -2,4-diFPh | —CH₂CCH | —H | —Et | 68–71 | D + A |
| 71 | -2,5-diFPh | —CH₂CCH | —SMe | —Et | 99–102 | D + A |
| 76 | —Ph | —Me | —H | —CF₃ | 135–138 | D + A |
| 77 | —Ph | —CH₂CCH | —H | —CF₃ | 103–106 | D + A |
| 79 | -2-thienyl | —CH₂CCH | —H | —Me | 110–112 | D + A |
| 80 | —Ph | —CH₂CCH | —H | —CH₂Cl/—CH₂Br mixture | 103.5–105 | A |
| 81* | -3-thienyl | —CH₂CCH | —H | —Et | solid | A |
| 83 | —Ph | —CH₂CCH | —CH₂CCH | —Et | 97–99 | D + A |
| 84 | —Ph | —CH₂CCH | —Et | —Et | 128–130 | D + A |
| 86 | —Ph | —CH₂CCH | —Et | i-Pr | 92–94 | D + A |
| 87 | -3-NO₂—Ph | —CH₂CCH | —Et | —Et | 114–119 | D + A |
| 88 | -3-CF₃—Ph | —CH₂CCH | —Br | —Et | 67–70 | D + A |
| 89 | -3-FPh | —CH₂CCH | —I | —Ph | 166–169 | D + A |
| 90 | —Ph | —CH₂CCH | —CCSiMe₃ | —Et | 114–116 | D + Y1 + A |
| 91 | -3-ClPh | —CH₂CCH | —Et | —Et | 175–177 | D + A |
| 92 | —Ph | —CH₂CCH | —Cl | —Et | Oil | D + Y2 + A |
| 94 | -2-FPh | —CH₂CCH | —SMe | —Et | 76.5–79 | D + Y2 + A + Z7 |
| 95 | -3-MePh | —CH₂CCH | —H | —Et | 70–73 | D + A |
| 96 | -3-MeO—Ph | —CH₂CCH | —H | —Et | 72–75 | D + A |
| 97 | —Ph | —CH₂CCH | —CH₂CCH | —Br | 94–95 | E + H + I + A |
| 98 | -3-ClPh | —CH₂CCH | —Et | —Et | 109–111.5 | D + A |
| 99 | -3-thienyl | —CH₂CCH | —Et | —Et | 123–126.5 | D + A |
| 103 | —Ph | —CH₂CCH | —Et | -n-Pr | 82.5–85 | D + A |
| 105 | —Ph | —CH₂CCH | —CH₂CO₂Me | —Et | 153–154 | D + Y3 + I + A |
| 106 | —Ph | —CH₂CCH | —Et | —Cl | 108–109.5 | E + H + I + A |
| 107 | —Ph | —CH₂CCH | —Et | —F | 132–134 | E + H + Y3 + I + A |
| 108 | —Ph | —CH₂CCH | —F | —Et | 95–99.5 | D + A |

TABLE 1-continued

| No. | | | | mp | method |
|---|---|---|---|---|---|
| 110 | 2,6-diCl-4-pyridyl | —CH₂CCH | —Et | 140–142 | D + A |
| 111 | —Ph | —CH₂CCCH₂ | —Et | 104–106 | B + Z12 |
| 112 | —Ph | —CH₂CCH | 3-furyl | 114–115 | D + A |
| 113 | —Ph | —CH₂CCH | 2-thienyl | 133–135 | D + A |
| 114 | —Ph | —Et | —Et | 61–65 | D + A |
| 115 | 3-FPh | —CH₂CCH | —CF₃ | 102–105 | D + A |
| 116 | —Ph | —CH₂CCH | 3-thienyl | 82–85 | D + A |
| 117 | 3-FPh | —CH₂CCH | -i-Pr | 124.5–127.5 | D + A |
| 118 | 3-ClPh | —CH₂CCH | -i-Pr | 112–115 | D + A |
| 119 | —Ph | —CH₂CCH | 4-pyridyl | Oil | D + A |
| 120 | —Ph | —CH₂CCH | cyclo-Bu | 113–115 | D + A |
| 121 | —Ph | —CH₂CCH | —CH₂Ph | 105–107 | D + A |
| 122 | 3,5-diFPh | —CH₂CCH | —Et | 125–126.5 | D + A |
| 123 | —Ph | —Et | —Et | Oil | D + A + Z10 |
| 124** | —Ph | —CH₂CCH | —CF₂Cl | 115–117 | D + A |
| 125 | —Ph | —CH₂CCH | -i-Bu | 83–86 | E + A |
| 126 | —Ph | —Me | —OMe | 90–93 | F + A |
| 127 | —Ph | —CH₂CCH | —OEt | 122–124 | D + A |
| 128 | —Ph | —CH₂CCH | cyclopropyl | 110–112 | D + A |
| 129 | —Ph | —CH₂CCH | —CF₃ | 123–125 | B |
| 130 | 3-ClPh | —CH₂CCH | —CHMe₂ | 94–97 | D + A |
| 131 | —Ph | —CH₂CCH | —Et | 97–99 | D + A |
| 132 | 3-BrPh | —CH₂CCH | —CF₃ | 129–131 | B + Z8 |
| 133 | 1-oxo-4-pyridyl | —CH₂CCH | —CF₃ | 149–152 | B |
| 134 | 2,6-diCl-4-pyridyl | —CH₂CCH | —Me | 168–170 | D + A |
| 135 | 2,6-diCl-4-pyridyl | —Me | —Me | 138–140 | F + A |
| 136 | 2,6-diCl-4-pyridyl | —CH₂CCH | —Et | 115–120 | D + A |
| 137 | 3-CN—Ph | —CH₂CCH | —CF₃ | 80.5–83 | D + A + Z14 + Z17 |
| 138 | 3-(1,3-dioxolan-2-yl)—Ph | —CH₂CCH | —CF₃ | 190–192 | D + A + Z14 + Z16 |
| 139 | 3-(HONCH)—Ph | —CH₂CCH | —Et | 80–82 | D + A + Z14 + Z16 |
| 140 | 3-Cl-4-F—Ph | —CH₂CCH | —Et | 120–122 | B + Z8 + Z9 |
| 141 | 2-CN-4-pyridyl | —CH₂CCH | —CF₃ | Oil | D + A |
| 142 | 2,6-diMeO-4-pyridyl | —CH₂CCH | —Et | 132–134 | D + A |
| 143 | 2-MeO-4-pyridyl | —Et | —Et | 81–83 | B |
| 144 | 2-F-4-pyridyl | —CH₂CCH | —Et | 90–100 | D + A |
| 145 | 2,6-diCl-4-pyridyl | —CH₂CCH | -n-Pr | 147–150 | D + A |
| 146 | 2,6-diCl-4-pyridyl | —Me | -n-Pr | 140–142 | D + A |
| 147 | 3-Cl—Ph | —CH₂CCH | -n-Pr | 56–61 | D + A |
| 148 | —Ph | —CH₂CCH | -s-Bu | 86–87.5 | D + A |
| 149 | 3-F—Ph | —CH₂CCH | —CHF₂ | 55–58 | D + A |
| 150 | 2-CF₃O—Ph | —CH₂CCH | -n-pentyl | 73–75 | D + A |
| 151 | 2-Me-4-pyridyl | —CH₂CCH | —Et | 43–47 | D + A |
| 152 | —Ph | —CH₂CCH | —Et | 123–124 | B |
| 153 | —Ph | —CH₂CCH | cyclopentyl | 35–39 | D + A |
| 154 | 3,4-diF—Ph | —CH₂CCH | —Et | 75–79 | D + A |
| 155 | 3-CF₃O—Ph | —CH₂CCH | —Et | Oil | D + A |
| 156 | —Ph | —CH₂CCH | —Cl | 120–123 | D + A |
| 157 | 4-pyridyl | —CH₂CCH | —Et | 116–119 | E + H + I + A |
| 158 | 3-F—Ph | —CH₂CCH | —Cl | 80–82 | D + A |
| 159 | 3-pyridyl | —CH₂CCH | Cl | 92–94 | E + H + I + A |
| 160 | 3-Cl—Ph | —CH₂CCH | —Et | 103–106 | D + A + Z8 |
| 161 | 1-oxo-4-pyridyl | —CH₂CCH | —Et | 127–130 | |

TABLE 1-continued

| No. | R2 | R3 | R5 | R6 | M.p. | Meth. Synth. |
|---|---|---|---|---|---|---|
| 163 | 3-Cl—Ph | —CH₂CCH | —Et | i-Pr | 90–92 | D + A |
| 164 | 3-Cl—Ph | —CH₂CCH | —H | —Et | 123–125 | D + A |
| 165 | -1-oxo-3-pyridyl | —CH₂CCH | —Et | —Et | 108–111 | D + A + Z8 |
| 166 | -3,4,5-triF²—Ph | —CH₂CCH | —Et | —Et | 113–114 | D + A |
| 167 | 2-Cl—Ph | —CH₂CCH | —Et | —Et | 91–93.5 | D + A |
| 168 | —Ph | —CH₂CCH | —Et | -n-C₇H₁₅ | 63–66 | D + A |
| 169 | -6-Cl-2-pyridyl | —CH₂CCH | —H | —CF₃ | 120–121 | B |
| 170 | -4-Cl-2-thienyl | —CH₂CCH | —Et | —Et | 134–137 | D + A |
| 171 | -2-thienyl | —CH₂CCH | —Et | —Et | 135–136.5 | D + A |
| 172 | —Ph | —CH₂CCH | —Cl | —Et | 112–114 | D + Y4 + A |
| 173 | -2,6-diF-4-pyridyl | —CH₂CCH | —H | —CF₃ | 135–137 | B |
| 174 | -5-Cl-2-thienyl | —CH₂CCH | —Et | —Et | 131–133 | D + A |
| 175 | —Ph | —CH₂CN | —Et | —Et | 239–240 | D + A |
| 176 | -2,6-diCl-4-pyridyl | —CH₂CCH | —Me | —CF₃ | 131–134 | B |
| 177 | -5-Cl-3-thienyl | —CH₂CCH | —Et | —Et | 134–136.5 | D + A |
| 178 | -2,5-diCl-3-thienyl | —CH₂CCH | —Et | —CF₃ | Oil | B + Z3 |
| 179 | —Ph | —CH₂COCH₃ | —Et | —Et | 131–133 | D + A |
| 180 | -5-Cl-3-pyridyl | —CH₂CCH | —Et | —Et | Oil | D + A |
| 181 | —Ph | cis & trans —CH₂CHCHCl | —Et | —Et | Oil | D + A |
| 182 | —Ph | —CH₂CCSiMe₃ | —Et | —Et | 131–132.5 | D + A + Z11 |
| 183 | —Ph | —CH₂CCH | —OMe | —Et | 64–66 | B |
| 184 | -3-F-5-CF₃—Ph | —Et | —Et | —Et | 81–83 | D + Y2 + A + Z15 |
| 185 | —Ph | —CH₂CCH | —CF₃ | —Et | 117–119 | D + A |
| 207 | -3-furyl | —CH₂CCH | —H | —CF₃ | 148–150 | B |
| 212 | -3-Cl-4-Me—Ph | —CH₂CCH | —Et | —CF₃ | 113–115 | B + Z18 |
| 215 | -3,5-diCl-4-Me—Ph | —CH₂CCH | —H | —CF₃ | 120–125 | B |
| 219 | —Ph | —CH₂Cl | —Et | —CF₃ | — | B |
| 220 | -3,5-diCl-4-F-Ph | —CH₂CCH | —H | —CF₃ | | |

| Compound No. | R2 | R3 | R5 | R6 | M.p. | Meth. Synth. |
|---|---|---|---|---|---|---|
| 189 | Ph | CH2CCH | OMe | CHF2 | 131–135 | D + A |
| 190 | Ph | CH2CCH | OMe | CHF2 | 109–111.5 | D + A |
| 191 | Ph | CH2CCH | OMe | CHF2 | 128–131 | E + H + I + A |
| 199 | 2,6-diCl-4-pyridyl | CH2CCH | OMe | CHF2 | 109–115 | D + A |
| 203 | Ph | CH2CCH | H | OPh | 140–142 | E + Y5 + A |
| 209 | 3-F—Ph | CH2CCH | H | CF3 | 71–74 | B |
| 210 | 3,5-diCl—Ph | CH2CCH | H | CF3 | 149–152 | B |
| 216 | 3,4-methylenedioxy-Ph | CH2COMe | OMe | Et | 88–91 | D + A |
| 221 | 2,6-diCl-4-pyridyl | CH2CCH | OMe | Et | 173–178 | D + A + Z22 |
| 222 | 3-F—Ph | CH2CCH | OMe | Et | 120–122 | D + A |
| 223 | 3-Cl—Ph | CH2CCH | Et | Et | 71–73 | D + A |
| 224 | 2,6-diCl-4-pyridyl | CH2CCI | OMe | CHF2 | Oil | B |
| 225 | 3-Cl—Ph | CH2CCH | Et | CHF2 | 131–133 | B |
| 226 | 3-F—Ph | CH2CCH | Et | CHF2 | 94–96 | B |
| 227 | 3-F—Ph | CH2CCH | OMe | CHF2 | 90–92 | B |
| 228 | 2,6-diCl-4-pyridyl | CH2CCH | CH2CH2OMe | CF3 | 149–152 | B |
| 229 | Ph | CH2CCH | Et | CF3 | 151–152 | B |
| 230 | Ph | CH2CCMe | Et | Et | 123–124 | D + A |
| 231 | Ph | CH2CHCH2 | CF3 | Et | 83–85 | D + Y2 + A + Z15 |
| 232 | Ph | CH2CHCH2 | H | Et | Oil | D + Y2 + A + Z15 |

TABLE 1-continued

| | | | | | |
|---|---|---|---|---|---|
| 233 | Ph | CH2CCH | OMe | Me | 94-98 | D + A |
| 234 | 2,6-diCl-4-pyridyl | CH2CCH | OMe | Me | — | D + A |
| 235 | Ph | CH2CCH | OEt | Et | 144-148 | D + A |
| 236 | Ph | CH2CCH | CH2OH | CF3 | >220 | J + K + L + A |
| 237 | Ph | CH2CCH | H | CHF2 | 69-72 | B |
| 238 | 2,6-diCl-4-pyridyl | CH2CCH | H | CHF2 | 129-131 | B |
| 239 | 3,5-diCl—Ph | CH2CCH | OMe | Et | 126-130 | D + A |
| 240 | Ph | CH2CCH | CH2OMe | CF3 | 131-132 | J + K + L + A + Z19 |
| 241 | Ph | CH2CCH | CH2F | CF3 | 134-135 | J + K + L + A + Z20 |
| 242 | 2,6-diCl-4-pyridyl | CH2CCH | OMe | n-Pr | 108-109 | D + A |
| 243 | 2-Cl-4-pyridyl | CH2CCH | H | CF3 | 125-126 | B |
| 244 | Ph | CH2CH(OMe)2 | Et | CF3 | 71-73 | B |
| 245 | 3,5-diF—Ph | CH2CCH | OMe | Et | 97-100 | D + A |
| 246 | Ph | CH2CCH | CHO | CF3 | 110-112 | J + K + L + A + Z23 |
| 247 | Ph | CH2CCH | CHNOH | CF3 | >200 | J + K + L + A + Z23 + M |
| 248 | Ph | CH2CCH | CHNOMe | CF3 | 131-132 | J + K + L + A + Z23 + M |
| 249 | Ph | CH2CCH | CH(OCH2CH2O) | CF3 | 185-187 | J + K + L + A + Z24 |

For the below table, "Me" is methyl, "Et" is ethyl, "Pr" is propyl, "Bu" is butyl, "Pe" is pentyl, "Bn" is benzyl, and "Ph" is phenyl; and except as noted, X=O (oxygen).

TABLE 1

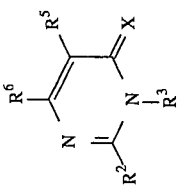

For the below table, "Me" is methyl, "Et" is ethyl, "Pr" is propyl, "Bu" is butyl,
"Pe" is penyl, "Bn" is benzyl, and "Ph" is phenyl; and except as noted, X = O (oxygen).

| Compound No. | $R^2$ | $R^3$ | $R^5$ | $R^6$ | MP °C. | Synthesis |
|---|---|---|---|---|---|---|
| 1 | —Ph | —CH$_2$CCH | —Me | —Me | 125–128 | D + A |
| 2 | —Ph | —CH$_2$CCH | —H | —Me | 148–149 | D + A |
| 4 | —Ph | —CH$_2$CCH | —H | —CF$_3$ | 118–120 | D + A |
| 5 | —Ph | —CH$_2$CCH | —Me | —Et | 115–117 | D + A |
| 6 | —Ph | —CH$_2$OCH$_3$ | —H | —CF$_3$ | 89–90 | D + Z6 |
| 7 | —Ph | —CH$_2$CCH | —Br | —CF$_3$ | 156–160 | D + Y1 + A |
| 8 | —Ph | —CH$_2$CCH | —Me | —Ph | 170–173 | D + A |
| 9 | —Ph | —CH$_2$CCH | —Cl | —Me | 131–134 | D + A |
| 11 | —Ph | —CH$_2$CCH | —H | —t-C$_4$H$_9$ | Oil | D + A |
| 12 | —Ph | —CH$_2$CCH | —i-Pr | —Pr | 72.5–74 | D + A |
| 13 | —Ph | —CH$_2$CCH | —Et | —Me | 79–80.5 | D + A |
| 14 | —Ph | —CH$_2$CCH | —H | —Me | 103–106 | D + A |
| 15 | —Ph | —Et | —Me | —Me | 77–78 | D + A |
| 16 | —Ph | —CH$_2$CCH | —Me | —Cl | 137.5–139 | E + H + I + A |
| 17 | —Ph | —CH$_2$CCH | —n-Pe | —Me | 92–93.5 | D + A |
| 18 | —Ph | —CH$_2$CCH | —H | —CF$_3$ | Oil | D + A |
| 19 | —Ph | —CH$_2$CHCH$_2$ | —Me | —C(O)NMe$_2$ | 137–140 | D + A + Z1 |
| 20 | —Ph | —CH$_2$CCH | —H | —CF$_3$ | Solid | B |
| 21 | —Ph | —Et | —Et | —CF$_3$ | 99–100.5 | D + A |
| 22 | —Ph | —CH$_2$CCCH$_2$CH$_3$ | —Me | —Et | 101–103 | D + A |
| 23 | —Ph | —CH$_2$CCH | —Me | —NMe$_2$ | 111.5–113.5 | E + H + I + A + Z2 |
| 25 | —Ph | —CH$_2$C(O)Me | —Me | —C$_2$H$_5$ | 87–89 | D + Z3 |
| 26 | —Ph | —CH$_2$CCH | —H | —SMe | 156–159 | E + H + I + A + Z4 |
| 27 | —Ph | —CH$_2$CCH | —Et | —C$_2$F$_5$ | 134–136 | D + A |
| 28 | —Ph | —CH$_2$CCH | —Me | —Ph | 124–126 | D + A |
| 29 | —Ph | —CH$_2$CCH | —n-Pr | —CF$_3$ | 143–145 | D + A |
| 30 | —Ph | —CH$_2$CCH | —OMe | —CF$_3$ | 155–157 | D + A |
| 31 | —Ph | —CH$_2$CCH | —H | —C$_2$H$_5$ | 103–106 | D + A |
| 32 | —Ph | —CH$_2$CCH | —Me | —CH$_2$OMe | 101–103 | D + A |
| 33 | —Ph | —CH$_2$CCH | —Me | —Et | 125–127 | D + A |
| 35 | 4-ClPh | —CH$_2$CCH | —Me | —Et | 109–111 | D + A |
| 36 | —Ph | —CH$_2$C(OMe)$_2$Me | —H | —CF$_3$ | 85–88 | D + A |
| 37 | —Ph | —CH$_2$CH$_2$OMe | —H | —CF$_3$ | 49–51 | D + A + Z5 |
| 38 | —Ph | —CH$_2$CCH | —CN | —SMe | 189–191 | B |
| 39 | —Ph | —CH$_2$CCCH$_3$ | —H | —CF$_3$ | 85–88 | A |

TABLE 1-continued

| | | | | | |
|---|---|---|---|---|---|
| 40 | —Ph | —CH₂CCH | —F | —Cl | 113–115 | D + H + I + A |
| 41 | —Ph | —Ph | —H | —CF₃ | 149–151 | B |
| 45 | —Ph | —CH₂CCH | —H | —CCl₃ | 86–91 | D + A |
| 46 | —Ph | —CH₂CCH | —Et | —CF₃ | 113–115 | BorD + A |
| 47 | —Ph | —CH₂CCH | —SMe | —CF₃ | 159–162 | D + A |
| 48 | —Ph | —CH₂CCH | —Me | i-Pr | 120–122 | D + A |
| 51 | —Ph | —CH₂CCH | —Me | —H | 135–136 | D + A |
| 52 | —Ph | —CH₂CCH | —Me | —CO₂Et | 147–150 | D + A |
| 53 | —Ph | —CH₂CHCH₂ | | —CF₃ | 73–76 | B |
| 54 | -2-Cl-4-pyridyl | —CH₂CCH | —Et | —CF₃ | 82–84 | B |
| 55 | —Ph | —CH₂CCH | —Et | -n-Bu | 57–59 | B |
| 56 | -2-Cl-4-pyridyl | —CH₂CCH | —Et | —Et | 84–86 | D + A |
| 57 | -3,5-diClPh | —CH₂CCH | —Et | —Et | 113–114 | D + A |
| 58 | -4-pyridyl | —CH₂CCH | —Et | —CF₃ | 114–116 | B |
| 59 | -2-Cl-6-Me-4-pyridyl | —CH₂CCH | —Et | —Et | 119–121 | D + A |
| 60 | -3-pyridyl | —CH₂CCH | —Et | —CF₃ | 116–118 | B |
| 61 | -1-Me-3-pyridinium iodide | —CH₂CCH | —Et | —CF₃ | >170(dec) | B + Z13 |
| 62 | -2-F-4-pyridyl | —CH₂CCH | —Et | —CF₃ | Oil | B |
| 63 | -5,6-diCl-3-pyridyl | —CH₂CCH | —Et | —CF₃ | 89–92 | B |
| 64 | -3,4-diFPh | —CH₂CCH | —Et | —Et | 97–99 | D + A |
| 65 | -2,6-diCl-4-pyridyl | —CH₂CCH | —Et | —CF₃ | 129–131 | B |
| 66 | -5-Br-3-pyridyl | —CH₂CCH | —Et | —CF₃ | 123–125 | B |
| 67 | -2,6-diCl-4-pyridyl | —CH₂CCH | —Et | i-Pr | solid | B |
| 68 | -4-FPh | —CH₂CCH | —Et | —Et | 107–109 | D + A |
| 69 | -3-formylPh | —CH₂CCH | —Et | —Et | 82–86 | D + A + Z14 |
| 70 | -2,4-diFPh | —CH₂CCH | —Et | —Et | 68–71 | D + A |
| 71 | -2,5-diFPh | —CH₂CCH | —Cl | —Et | 99–102 | D + A |
| 76 | —Ph | —CH₂CCH | —H | —CF₃ | 135–138 | D + A |
| 77 | -3-ClPh | —CH₂CCH | —SMe | —CF₃ | 103–106 | D + A |
| 79 | —Ph | —Me | | —Me | 110–112 | D + A |
| 80 | -2-thienyl | —CH₂CCH | —H | —CH₂Cl/—CH₂Br mixture | 103.5–105 | A |
| 81* | —Ph | —CH₂CCH | —H | —Et | solid | A |
| 83 | -3-thienyl | —CH₂CCH | —H | —Et | 97–99 | D + A |
| 84 | —Ph | —CH₂CCH | —H | i-Pr | 128–130 | D + A |
| 86 | —Ph | —CH₂CCH | | i-Pr | 92–94 | D + A |
| 87 | -3-NO₂—Ph | —CH₂CCH | —Et | —Et | 114–119 | D + A |
| 88 | -3-CF₃—Ph | —CH₂CCH | —Br | —Et | 67–70 | D + A |
| 89 | -3-ClPh | —CH₂CCH | | —Ph | 166–169 | D + Y1 + A |
| 90 | —Ph | —CH₂CCH | —I | —Et | 114–116 | D + A |
| 91 | -3-FPh | —CH₂CCH | —CCSiMe₃ | —Et | 175–177 | D + Y2 + A |
| 92 | -2-FPh | —CH₂CCH | —Et | —Et | Oil | D + Y2 + A |
| 94 | -3-FPh | —CH₂CCH | —Et | —Et | 76.5–79 | D + A |
| 95 | -3-MePh | —CH₂CCH | —Et | —Et | 70–73 | D + A |
| 96 | -3-MeO—Ph | —CH₂CCH | —Et | —Br | 72–75 | D + Y2 + A + Z7 |
| 97 | —Ph | —CH₂CCH | | —Et | 94–95 | D + A |
| 98 | -3-ClPh | —CH₂CCH | —CH₂CO₂Me | -n-Pr | 109–111.5 | E + H + I + A |
| 99 | -3-thienyl | —CH₂CCH | —Et | —Et | 123–126.5 | D + A |
| 103 | —Ph | —CH₂CCH | —Et | —Cl | 82.5–85 | D + A |
| 105 | —Ph | —CH₂CCH | —Et | —F | 153–154 | D + Y3 + I + A |
| 106 | —Ph | —CH₂CCH | —Et | —Et | 108–109.5 | E + H + I + A |
| 107 | —Ph | —CH₂CCH | —F | —Et | 132–134 | E + H + Y3 + I + A |
| 108 | —Ph | —CH₂CCH | —Et | —Et | 95–99.5 | D + A |

TABLE 1-continued

| No. | | | | mp | |
|---|---|---|---|---|---|
| 110 | -2,6-diCl-4-pyridyl | —CH₂CCH | —Et | 140–142 | D + A |
| 111 | —Ph | —CH₂CCCHCH₂ | —CF₃ | 104–106 | B + Z12 |
| 112 | —Ph | —CH₂CCH | -3-furyl | 114–115 | D + A |
| 114 | —Ph | —CH₂CCH | -2-thienyl | 133–135 | D + A |
| 115 | -3-FPh | —Et | —Et | 61–65 | D + A |
| 116 | —Ph | —CH₂CCH | —CF₃ | 102–105 | D + A |
| 117 | -3-FPh | —CH₂CCH | -3-thienyl | 82–85 | D + A |
| 118 | -3-FPh | —CH₂CCH | -i-Pr | 124.5–127.5 | D + A |
| 119 | -3-ClPh | —CH₂CCH | -i-Pr | 112–115 | D + A |
| 120 | —Ph | —CH₂CCH | -4-pyridyl | Oil | D + A |
| 121 | —Ph | —CH₂CCH | -cyclo-Bu | 113–115 | D + A |
| 122 | —Ph | —CH₂CCH | —CH₂Ph | 105–107 | D + A |
| 123 | -3,5-diFPh | —CH₂CCH | —Et | 125–126.5 | D + A |
| 124** | —Ph | —Et | —Et | Oil | D + A + Z10 |
| 125 | —Ph | —CH₂CCH | —CF₂Cl | 115–117 | D + A |
| 126 | —Ph | —CH₂CCH | -i-Bu | 83–86 | D + A |
| 126 | —Ph | —Me | —OMe | 90–93 | E + A |
| 128 | —Ph | —H | —OEt | 122–124 | F + A |
| 129 | —Ph | —CH₂CCH | -cyclopropyl | 110–112 | D + A |
| 130 | —Ph | —CH₂CCH | —CF₃ | 123–125 | B |
| 131 | —Ph | —CH₂CCH | —CHCMe₂ | 94–97 | D + A |
| 132 | -3-BrPh | —CH₂CCH | —Et | 97–99 | D + A |
| 133 | -1-oxo-4-pyridyl | —CH₂CCH | —CF₃ | 129–131 | B + Z8 |
| 134 | -2,6-diCl-4-pyridyl | —CH₂CCH | —CF₃ | 149–152 | B |
| 135 | -2,6-diCl-4-pyridyl | —H | —Me | 168–170 | D + A |
| 136 | -2,6-diCl-4-pyridyl | —Me | —Me | 138–140 | D + A |
| 137 | -3-CN—Ph | —CH₂CCH | —Et | 115–120 | D + A + Z14 + Z16 |
| 138 | -3-(1,3-dioxolan-2-yl)—Ph | —CH₂CCH | —Et | 80.5–83 | D + A |
| 139 | -3-(HONCH)—Ph | —CH₂CCH | —Et | 190–192 | D + A + Z14 + Z16 + Z17 |
| 140 | -3-Cl-4-F—Ph | —CH₂CCH | —Et | 80–82 | D + A + Z14 + Z16 |
| 141 | -2-CN-4-pyridyl | —CH₂CCH | —CF₃ | 120–122 | B + Z8 + Z9 |
| 142 | -2,6-diMeO-4-pyridyl | —CH₂CCH | —Et | Oil | D + A |
| 143 | -2,6-diCl-4-pyridyl | —H | —Et | 132–134 | D + A |
| 144 | -2-MeO-4-pyridyl | —CH₂CCH | —Et | 81–83 | D + A |
| 145 | -2-F-4-pyridyl | —CH₂CCH | —Et | 90–100 | D + A |
| 146 | -2,6-diCl-4-pyridyl | —Me | -n-Pr | 147–150 | D + A |
| 147 | -2,6-diCl-4-pyridyl | —CH₂CCH | -n-Pr | 140–142 | D + A |
| 148 | -3-Cl—Ph | —CH₂CCH | -n-Pr | 56–61 | D + A |
| 149 | -3-F—Ph | —CH₂CCH | —Et | 86–87.5 | D + A |
| 150 | -2-CF₃O—Ph | —CH₂CCH | —Et | 55–58 | D + A |
| 151 | -2-Me-4-pyridyl | —CH₂CCH | —Et | 73–75 | D + A |
| 152 | —Ph | —CH₂CCH | -s-Bu | 43–47 | D + A |
| 153 | —Ph | —CH₂CCH | —CHF₂ | 123–124 | B |
| 154 | —Ph | —CH₂CCH | -n-pentyl | 35–39 | D + A |
| 155 | -3,4-diF—Ph | —CH₂CCH | —Et | 75–79 | D + A |
| 156 | -3-CF₃O—Ph | —CH₂CCH | —Et | Oil | D + A |
| 157 | —Ph | —CH₂CCH | -cyclopentyl | 120–123 | D + A |
| 158 | -4-pyridyl | —CH₂CCH | —Et | 116–119 | E + H + I + A |
| 159 | -3-F—Ph | —CH₂CCH | —Cl | 80–82 | D + A |
| 160 | -3-pyridyl | —CH₂CCH | —Et | 92–94 | E + H + I + A |
| 161 | -3-Cl—Ph | —CH₂CCH | Cl | 103–106 | D + A |
| 162 | -1-oxo-4-pyridyl | —CH₂CCH | —Et | 127–130 | D + A + Z8 |

TABLE 1-continued

| Compound No. | R2 | R3 | R5 | R6 | M.p. | Meth. Synth. |
|---|---|---|---|---|---|---|
| 163 | 3-Cl—Ph | —CH₂CCH | —Et | —Me | 90–92 | D + A |
| 164 | 3-Cl—Ph | —CH₂CCH | —H | —Et | 123–125 | D + A |
| 165 | 1-oxo-3-pyridyl | —CH₂CCH | —Et | —Cl | 108–111 | D + A + Z8 |
| 166 | 3,4,5-triF—Ph | —CH₂CCH | —Et | —Et | 113–114 | D + A |
| 167 | 2-Cl—Ph | —CH₂CCH | —Et | —Et | 91–93.5 | D + A |
| 168 | —Ph | —CH₂CCH | —Et | —n-C₇H₁₅ | 63–66 | D + A |
| 169 | 6-Cl-2-pyridyl | —CH₂CCH | —H | —CF₃ | 120–121 | B |
| 170 | 4-Cl-2-thienyl | —CH₂CCH | —Et | —Et | 134–137 | D + A |
| 171 | 2-thienyl | —CH₂CCH | —Et | —Et | 135–136.5 | D + A |
| 172 | —Ph | —CH₂CCH | —Et | —Cl | 112–114 | D + Y4 + A |
| 173 | 2,6-diF-4-pyridyl | —CH₂CCH | —H | —CF₃ | 135–137 | B |
| 174 | 5-Cl-2-thienyl | —CH₂CCH | —Et | —Et | 131–133 | D + A |
| 175 | —Ph | —CH₂CN | —Et | —Et | 239–240 | D + A |
| 176 | 2,6-diCl-4-pyridyl | —CH₂CCH | —Me | —CF₃ | 131–134 | B |
| 177 | 5-Cl-3-thienyl | —CH₂CCH | —Et | —Et | 134–136.5 | D + A |
| 178 | 2,5-diCl-3-thienyl | —CH₂CCH | —Et | —Et | Oil | D + A |
| 179 | —Ph | —CH₂COCH₃ | —Et | —CF₃ | 131–133 | B + Z3 |
| 180 | 5-Cl-3-pyridyl | —CH₂CCH | —Et | —Et | Oil | D + A |
| 181 | —Ph | cis & trans —CH₂CHCHCl | —Et | —Et | Oil | D + A + Z11 |
| 182 | —Ph | —CH₂CCSiMe₃ | —Et | —Et | Oil | D + A |
| 183 | —Ph | —Et | —OMe | —Et | 131–132.5 | D + A |
| 184 | 3-F-5-CF₃—Ph | —CH₂CCH | —Et | —Et | 64–66 | B |
| 185 | —Ph | —CH₂CCH | —CF₃ | —Et | 81–83 | D + Y2 + A + Z15 |
| 207 | 3-furyl | —CH₂CCH | —H | —Et | 117–119 | D + A |
| 212 | 3-Cl-4-Me—Ph | —CH₂CCH | —Et | —CF₃ | 148–150 | B |
| 215 | 3,5-diCl-4-Me—Ph | —CH₂CCl | —H | —CF₃ | 113–115 | B |
| 219 | —Ph | —CH₂CCH | —Et | —CF₃ | 120–125 | B + Z18 |
| 220 | 3,5-diCl-4-F-Ph | —CH₂CCH | —H | —CF₃ | — | B |
| 189 | Ph | CH2CCH | OMe | i-Pr | 131–135 | D + A |
| 190 | Ph | CH2CCH | OMe | n-Pr | 109–111.5 | D + A |
| 191 | Ph | CH2CCH | OMe | Cl | 128–131 | E + H + I + A |
| 199 | 2,6-diCl-4-pyridyl | CH2CCH | H | Et | 109–115 | D + A |
| 203 | Ph | CH2CCH | H | OPh | 140–142 | E + Y5 + A |
| 209 | 3-F—Ph | CH2CCH | Et | CF3 | 71–74 | B |
| 210 | 3,5-diCl—Ph | CH2CCH | Et | CF3 | 149–152 | B |
| 216 | 3,4-methylenedioxy-Ph | CH2COMe | OMe | Et | 88–91 | D + A + Z22 |
| 221 | 2,6-diCl-4-pyridyl | CH2CCH | OMe | Et | 173–178 | D + A |
| 222 | 3-F—Ph | CH2CCH | Et | Et | 120–122 | D + A |
| 223 | 3-Cl—Ph | CH2CCH | Et | CHF2 | 71–73 | D + A |
| 224 | 2,6-diCl-4-pyridyl | CH2CCH | OMe | CHF2 | Oil | B |
| 225 | Ph | CH2CCH | Et | CHF2 | 131–133 | B |
| 226 | 3-Cl—Ph | CH2CCH | Et | CHF2 | 94–96 | B |
| 227 | 3-F—Ph | CH2CCH | OMe | CHF2 | 90–92 | B |
| 228 | 2,6-diCl-4-pyridyl | CH2CCH | CH2CH2OMe | CF3 | 149–152 | B |
| 229 | Ph | CH2CCH | Et | CF3 | 151–152 | D + A |
| 230 | Ph | CH2CCMe | CF3 | Et | 123–124 | B |
| 231 | Ph | CH2CHCH2 | Et | Et | 83–85 | D + Y2 + A + Z15 |
| 232 | Ph | CH2CHCH2 | H | Et | Oil | D + Y2 + A + Z15 |

TABLE 1-continued

| | | | | | |
|---|---|---|---|---|---|
| 233 | Ph | CH2CCH | OMe | Me | 94-98 | D + A |
| 234 | 2,6-diCl-4-pyridyl | CH2CCH | OMe | Me | — | D + A |
| 235 | Ph | CH2CCH | OEt | Et | 144-148 | D + A |
| 236 | Ph | CH2CCH | CH2OH | CF3 | >220 | J + K + L + A |
| 237 | 2,6-diCl-4-pyridyl | CH2CCH | H | CHF2 | 69-72 | B |
| 238 | 3,5-diCl—Ph | CH2CCH | H | CHF2 | 129-131 | B |
| 239 | Ph | CH2CCH | OMe | Et | 126-130 | D + A |
| 240 | 2,6-diCl-4-pyridyl | CH2CCH | CH2OMe | CF3 | 131-132 | J + K + L + A + Z19 |
| 241 | Ph | CH2CCH | CH2F | CF3 | 134-135 | J + K + L + A + Z20 |
| 242 | 2,6-diCl-4-pyridyl | CH2CCH | OMe | n-Pr | 108-109 | D + A |
| 243 | 2-Cl-4-pyridyl | CH2CCH | H | CF3 | 125-126 | B |
| 244 | Ph | CH2CH(OMe)2 | Et | CF3 | 71-73 | B |
| 245 | 3,5-diF—Ph | CH2CCH | OMe | Et | 97-100 | D + A |
| 246 | Ph | CH2CCH | CHO | CF3 | 110-112 | J + K + L + A + Z23 + M |
| 247 | Ph | CH2CCH | CHNOH | CF3 | >200 | J + K + L + A + Z23 + M |
| 248 | Ph | CH2CCH | CHNOMe | CF3 | 131-132 | J + K + L + A + Z23 + M |
| 249 | Ph | CH2CCH | CH(OCH2CH2O) | CF3 | 185-187 | J + K + L + A + Z23 + Z24 |

The following ¹H-NMR data is provided for compounds in the above table which were oils or solids whose melting points were not determined. These spectra were recorded at 200 MHz in CDCl₃. Chemical shifts are expressed in parts per million downfield of tetramethylsilane, which was used as standard.

pounds listed as examples within the embodiment of the present invention:

| Compound No. | ¹H-NMR |
|---|---|
| 11 | 1.25(9H, s), 2.35(1H, t), 4.6(2H, d), 6.5(1H, s), 7.55(3Hm), 7.7(2H, m) |
| 18 | 4.6(2H, m), 5.0(1H, dd), 5.25(1H, dd), 5.9(1H, m), 6.9(1H, s), 7.55(5H, m) |
| 20 | 1.25(3H, t), 4.0(2H, q), 6.85(1H, s), 7.5(5H, m) |
| 62 | 1.25(3H, t), 2.5(1H, t), 2.80(2H, q), 4.65(2H, d), 7.35(1H, s), 7.6(1H, d), 8.5(1H, d) |
| 67 | 1.15(3H, t), 1.2(6H, d), 2.5(1H, t), 2.65(2H, q), 3.15(1H, m), 4.6(2H, d), 7.65(2H, s) |
| 81 | 2.4(1H, t), 4.3(2H, s), 4.6(2H, d), 6.65(1H, s), 7.55(3H, m), 7.7(2H, m) [6-CH₂Br] |
|    | 2.4(1H, t), 4.4(2H, s), 4.6(2H, d), 6.71(1H, s), 7.55(3H, m), 7.7(2H, m) [6-CH₂Cl] |
| 92 | 0.25(9H, s), 1.25(3H, t), 2.37(1H, t), 2.85(2H, q), 4.60(2H, d), 7.55(3H, m), 7.75(2H, m) |
| 120 | 1.25(3H, t), 2.43(1H, t), 2.61(2H, q), 4.68(2H, d), 7.5(2H, d), 7.55(3H, m), 7.75(2H, m), 8.75(2H) |
| 124 | 1.25(9H, m), 2.7(2H, q), 3.08(2H, q), 4.62(2H, d), 7.5(5H, m) |
| 142 | 1.15(3H, t), 1.25(3H, t), 2.35(1H, t), 2.60(4H, q), 3.95(6H, s), 4.55(2H, d), 6.55(2H, s) |
| .156 | 1.25(6H, m), 2.4(1H, t), 2.65(4H, q), 4.6(2H, d), 7.35–7.75(4H, m) |
| 178 | 1.35(6H, m), 2.78(4H, m), 2.95(1H, t), 4.9(2H, d), 8.2(1H, s) |
| 180 | 1.20(3H, t), 1.25(3H, t), 2.45(1H, t), 2.65(4H, q), 4.60(2H, d), 8.10(1H, s), 8.75(1H, s), 8.85(1H, s). |
| 181 | 1.2(6H, m), 2.65(4H, m), 4.5(2H, m), 5.95(2H, m), 7.5(5H, m), {cis} |
|     | 1.2(6H, m), 2.65(4H, m), 4.7(2H, m), 5.95(1H, m), 6.15(1H, m), 7.5(5H, m) {trans} |
| 182 | 0.18(9H, s), 1.25(6H, m), 2, 65(4H, q), 4.6(2H, s), 7.42–7.8(5H, m) |
| 220 | 2.5(1H, t), 4.6(2H, d)6.9(1H, s), 7.8(2H, d) |
| 224 | 1.25(3H, t), 2.50(1H, t), 2.77(2H, q), 4.60(2H, d), 6.55(1H, t), 7.65(2H, s) |
| 232 | 1.25(3H, t), 2.60(2H, q), 4.5(2H, d), 4.9(1H, d), 5.15(1H, d), 5.85(1H, m), 6.35(1H, s), 7.5(5H). |
| 234 | 2.35(3H, s), 2.5(1H, t), 4.0(3H, s), 4.6(2H, d), 7.62(2H, s). |

The following table of compounds are additional com-

TABLE 2

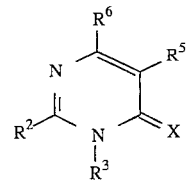

For the below table, "Me" is methyl, "Et" is ethyl, "Pr" is propyl and "Ph" is phenyl. For the compounds, X is preferably oxygen.

| No | R² | R³ | R⁵ | R⁶ |
|---|---|---|---|---|
| 186 | —Ph | —CH₂CCH | —CF₃ | —Et |
| 187 | —Ph | —CH₂CCH | —Et | —CN |
| 188 | —Ph | —CH₂CCH | —CH₂F | —Et |
| 192 | -2,6-diCl-4-pyridyl | —CH₂CCH | —Et | —Cl |
| 193 | -2-CF₃-4-pyridyl | —CH₂CCH | —Et | —Et |
| 194 | -4-Cl-2-pyridyl | —CH₂CCH | —Et | —Et |
| 195 | -4,6-diCl-2-pyridyl | —CH₂CCH | —Et | —Et |
| 196 | -2-pyridyl | —CH₂CCH | —Et | —Et |
| 197 | -2-naphthyl | —CH₂CCH | —Et | —Et |
| 198 | -2,6-diF-4-pyridyl | —CH₂CCH | —Et | —Et |
| 200 | —Ph | —CH₂CCH | —Et | —C(CH₃)CH₂ |
| 201 | —Ph | —CH₂CCH | —Et | —CH₂CCH |
| 202 | —Ph | —CH₂CCH | —Et | —CH₂CHCH₂ |
| 204 | —Ph | —CH₂CCH | —Et | —OMe |
| 205 | —Ph | —CH₂CCH | —Et | —OCHF₂ |
| 206 | —Ph | —CH₂CCH | —OCHF₂ | —Et |
| 208 | -5-Cl-3-furyl | —CH₂CCH | —Et | —Et |
| 211 | -3,5-diF—Ph | —CH₂CCH | —H | —CF₃ |
| 213 | -3-Cl-4-F—Ph | —CH₂CCH | —H | —CF₃ |
| 214 | -3,4-diF—Ph | —CH₂CCH | —H | —CF₃ |
| 217 | -5-Cl-3-thienyl | —CH₂CCH | —Et | —CF₃ |
| 218 | -3,4,5-triF—Ph | —CH₂CCH | —Et | —CF₃ |

TABLE 2-continued

| Compound No. | $R^2$ | $R^3$ | $R^5$ | $R^6$ |
|---|---|---|---|---|
| 250 | 2-Cl-4-pyridyl | CH2CCH | OMe | Et |
| 251 | 2,6-diCl-4-pyridyl | CH2CCH | OMe | i-Pr |
| 252 | 3-F—Ph | CH2CCH | H | CHF2 |
| 257 | 2-Cl-4-pyridyl | CH2CCH | H | CHF2 |
| 258 | Ph | CH2CCH | SMe | Et |
| 259 | Ph | CH2CCH | CH2OH | Et |
| 260 | 2,6-diCl-4-pyridyl | CH2CCH | CH2OH | Et |
| 261 | Ph | CH2CCH | CH2OMe | Et |
| 262 | 2,6-diCl-4-pyridyl | CH2CCH | CH2OMe | Et |
| 263 | Ph | CH2CCH | CH2F | Et |
| 264 | Ph | CH2CCH | Et | CH2F |
| 265 | 2,6-diCl-4-pyridyl | CH2CCH | CH2OMe | Et |
| 266 | 2,6-diCl-4-pyridyl | CH2CCH | CHNOMe | Et |
| 267 | 2,6-diCl-4-pyridyl | CH2CCH | CH(OCH2CH2O) | Et |
| 268 | 2,6-diCl-4-pyridyl | CH2CCH | CHNOH | Et |
| 269 | 2,6-diCl-4-pyridyl | CH2CCH | CHO | Et |
| 270 | Ph | CH2CCH | COME | CF3 |
| 271 | ph | CH2ccH | CH(OMe)2 | CF3 |

Methods of Preparation.

The 2-arylpyrimidines of the present invention may be prepared by standard synthetic routes such as those illustrated below.

Method A—General Description:

A precursor compound having the structure of formula I above with hydrogen (H) in the $R^3$ substituent position is selected. Reaction with $R^3Y$ is performed in a base-solvent mixture. Y can be a halogen, alkanesulfonate, haloalkanesulfonate or optionally substituted benzenesulfonate. The bases can be sodium hydride, alkali metal hydroxides, alkali metal carbonates or alkali metal alkoxides. The solvent can be alcohol, ketone, water, ether, DMSO or DMF. A mixture of N— and O— alkylated products results.

Method A—Specific Example 1—Preparation of 6-ethyl-5-methyl-2-phenyl-3-propargyl- 4(3H)-pyrimidinone:

To a stirred solution of 24.30 g (0.45 mol) of sodium methoxide in 400 mL of methanol was added a slurry of 61.78 g (0.29 mol) of 6-ethyl-5-methyl-2-phenyl- 4(3H)-pyrimidinone in 100 mL of methanol. The mixture was heated to reflux to give a clear orange solution to which 44.89 g (0.30 mol) of an 80% weight solution of propargyl bromide in toluene was added. The course of the reaction was followed by GC. Refluxing was continued for 6.5 h, when an additional 20.63 g (0.14 mol) of an 80% weight solution of propargyl bromide in toluene was added. Refluxing was continued for an additional 4.5 h. The reaction mixture was allowed to cool to room temperature and 250 mL of water and 250 mL of saturated aqueous NaHCO3 were added. The mixture was rotovaped to remove the bulk of the methanol and extracted with three 200 mL portions of ethyl acetate. The ethyl acetate extracts were combined, filtered and extracted with three 200 mL portions of 5% aq HCl. The combined aqueous HCl extracts were basified to pH 11 with 50% aqueous NaOH and extracted with three 250 mL portions of ether. The combined ether extracts were washed with 100 mL of brine, dried over MgSO4 and rotovaped to leave 30.46 g of a yellowish solid. This material was triturated with 100 mL portions of 10, 25 and 50% ether in hexanes and recrystallized from 25 mL of toluene to furnish 15.11 g. of Compound 5 as a white solid mp 115°–117° C. $^1$H-NMR (d$^6$-DMSO)δ1.15(3H, t, J=7.8), 2.07(3H, s), 2.58(2H, q, J=7.8), 3.32(1H, t, J=2.4), 4.55(2H, d, J=2.4), 7.58(3H, m), 7.65(2H, m).

Method A—Specific Example 2—Preparation of 2-(2, 6-dichloro-4-pyridyl)-5,6-diethyl-3-propargyl- 4(3H)-pyrimidinone (Compound 110)

A stirred suspension of 84.63 g (0.28 mol) of 2-(2,6-dichloro-4-pyridyl)-5,6-diethyl-4(3H)-pyrimidinone, 12.74 g (0.30 mol) of lithium hydroxide monohydrate, 300 mL of water and 300 mL of methanol was heated to reflux and 48.41 g (0.33 mol) of 80% propargyl bromide in toluene was added dropwise over 10 min. The mixture was heated at reflux for 16 h. The mixture was cooled and rotovaped to remove the bulk of the methanol. The residue was treated with 300 mL of 5% aqueous hydrochloric acid and 600 mL of ethyl acetate and filtered. The grey solid collected was dried to afford 22.21 g of recovered 2-(2,6-dichloro-4-pyridyl)-5,6-diethyl-4(3H)-pyrimidinone. The organic layer of the filtrate was separated, washed with 300 mL of 5% aqueous hydrochloric acid and 300 mL of brine and dried over MgSO4. Removal of the solvent on the rotovap left 56.55 g of crude compound 110 as a grey solid. Purification was effected by chromatography on silica gel followed by filtration through activity III neutral alumina to afford 12.61 g (13%) of 2-(2,6-dichloro-4-pyridyl)-5,6-diethyl-3-propargyl-4(3H)-pyrimidinone (Compound 110) as a pale yellow solid mp 140°–142° C. 1H-NMR (CDCl3) 1.19 (3H,t), 1.28 (3H,t), 2.55 (1H,t), 2.65 (4H,m), 4.6 (2H,d), 7.68 (2H,s).

Method B—General Description:

Direct condensation of an N-alkylamidine and a beta-keto ester is performed by warming the reagents in a solvent such as THF or neat: $R^2C(=NH)N(H)R^3$ + $R^6C(=O)CH(R^5)C(=O)OR \rightarrow$ 2-arylpyrimidine (FIG. I) Preferably $R^3$ is a non-reactive group and when $R^3$ is a propargyl group, preferably $R^6$ is $CF_3$.

Method B—Specific Example—Preparation of 5-ethyl-2-phenyl-3-propargyl-6 -trifluoromethyl-4(3H)-pyrimidinone To a stirred solution of 22.66 g (0.13 mol) of methyl benzimidate hydrochloride in 80 mL of methanol was added 11.09 g (0.13 mol) of powdered sodium bicarbonate. The mixture was stirred for 0.5 h and 9.1 mL (0.13 mol) of propargylamine was added. The mixture was stirred for 4 h at room temperature and then rotovapped to remove most of the methanol. To the oily orange residue was added 34.00 g of 80% pure ethyl 2-trifluoroacetylbutyrate (0.13 mol). The mixture was heated at 55°–60° C. for 40 h. The mixture was diluted with 300 mL of ether, washed with two 150 mL portions of 5% aqueous HCl and 150 mL of saturated aqueous sodium bicarbonate and dried over MgSO4.

Removal of the solvent and drying at 50° C. under high vacuum afforded 22.58 g of an orange solid. This material was purified by flash chromatography on 325 g of silica gel, eluting with 0, 10, 20, 30 and finally 40% ether in hexanes to furnish 16.86 g of a yellow solid. This material was triturated with two 100 mL portions of boiling hexanes and recrystallized from 150 mL of 10% ether in hexanes to give 10.31 g (26%) of 5-ethyl-2-phenyl-3-propargyl-6 -trifluoromethyl-4(3H)-pyrimidinone (Compound No. 46) as a white solid, mp 111°–114° C. $^1$H-NMR (CDCl$_3$)δ1.24(3H, t), 2.38(1H,t), 2.75(2H, q), 4.62(2H,d), 7.55(3H,m), 7.74(2H,m).

Method D—General Description

An amidine hydrochloride or other salt is heated with a beta-keto ester in a solvent in the presence of a base to neutralize the hydrochloric acid. Solvents usable include xylene or toluene, preferably, or ethanol or heptane. Sodium acetate or sodium ethoxide can be the base:

R$^2$C(=NH)NH$_2$+R$^6$C(=O)CH(R$^5$)C(=O)OR→FIG. I with R$^3$=H; precursor for Method A Method D—Preparation of 6-ethyl-5-methyl-2-phenyl-4(3H)-pyrimidinone.

A 2 L 3-neck flask equipped with mechanical stirrer, Dean Stark trap and a reflux condenser was purged with nitrogen and charged with 93.91 g. (0.59 mol) of methyl 2-propionylpropionate, 103.58 g (≦0.66 mol) of benzamidine hydrochloride hydrate, 54.30 g (0.66 mol) of anhydrous sodium acetate and 1 L of xylenes. The mixture was stirred and heated to reflux under a nitrogen atmosphere for 46 h.

The Dean Stark trap was replaced with a distillation head and about 75% of the solvent was distilled off at atmospheric pressure. After the flask had cooled to room temperature, 500 mL of water and 200 mL of ether were added. The mixture was filtered and the solid collected was washed thoroughly with water and ether and dried in a vacuum oven at 60° C. to give 74.73 g (50%) of the desired product, mp 195°– 199° C. $^1$H-NMR (d$^6$-DMSO)δ1.23(3H, t, J=7.8), 2.02(3H, s), 2.61 (2H, q, J=7.8),7.50 (3H,m), 8.13(2H, m).

The filtrate was separated into aqueous and organic layers. The organic layer was extracted with three 125 mL portions of 5% aqueous NaOH. The combined aqueous base extracts were acidified to pH 7 with aqueous HCl, allowed to cool and filtered. The solid collected was washed with water and ether and dried in a vacuum oven at 60° C. to afford an additional 5.16 g (4%) of the desired product, mp 196°–199° C.

Method E—General Description

Malonate diester is condensed with an amidine under basic conditions. For example, sodium methoxide in refluxing methanol may be used:

R$^2$C(=NH)NH$_2$+ROC(=O)CH(R$^5$)C(=O)OR→FIG. I with R$^3$=H and R$^6$=OH.

Method E—Preparation of 5-ethyl-6-hydroxy-2-phenyl-4(3H)-pyrimidinone

A mixture of 45.19 g (0.29 mol) of benzamidine hydrochloride hydrate, 127.42 g (0.59 mol) of 25% sodium methoxide in methanol, 55 mL (0.29 mol) of diethyl ethylmalonate and 175 mL of methanol was heated at reflux for 25 h. The mixture was rotovapped to remove the bulk of the methanol. The residue was diluted with 300 mL of water and the pH was adjusted to 7 with concentrated hydrochloric acid. The solid precipitate was collected by filtration and dried under vacuum at 50° C. to afford 31.89 g (51%) of crude 5-ethyl-6-hydroxy-2-phenyl-4(3H)-pyrimidinone as a pale yellow solid. $^1$H-NMR (d$^6$-DMSO)δ1.05(3H, t), 2.39(2H,q), 7.5(3H,m), 8.1 (2H,m).

Method F—General Description

Method F is similar to Method D except that a 3-alkoxyacrylate ester is used instead of a beta-keto ester:

R$^2$C(=NH)NH$_2$+RO(R$^6$)C=C(R$^5$)C(=O)OR→FIG. I with R$^3$=H

Various conditions are usable: for example, amidine hydrochloride/3-alkoxyacrylate in NaOAc/DMSO at 120 degrees Centigrade or in sodium methoxide/ethanol at 5 degrees Centigrade.

Method F—Specific Example—Preparation of 6-ethoxy-2-phenyl-4(3H)-pyrimidinone

A mixture of 3.14 g (20.0 mmol) of benzamidine hydrochloride hydrate, 1.65 g (20.1 mmol) of powdered anhydrous sodium acetate, 4.17 g (22.2 mmol) of ethyl 3,3-diethoxyacrylate and 10 mL of DMSO was heated at 120° C. for 8 h. The mixture was cooled, diluted with 50 mL of 5% aqueous NaOH and washed with two 100 mL portions of ether. The aqueous layer was acidified with concentrated hydrochloric acid and the precipitate was collected by filtration and dried under vacuum at 50° C. to furnish 2.28 g (57%) of crude 6-ethoxy-2-phenyl-4(3H)-pyrimidinone as a yellow solid $^1$H-NMR (d6-DMSO)δ1.35(3H,t), 4.33(2H, q), 5.60(1H,s), 7.50(3H,m), 8.2(2H,m).

Method H—General Description

6-Hydroxy-4(3H)-pyrimidinones were heated with phosphorus oxyhalide with or without a cosolvent to give 6-halo-4(3H)-pyrimidinones. For example, phosphorous oxybromide was used with an inert solvent (1,2-dichloroethane) at reflux. See U.S. Pat. No. 4,617,393.

Method H—Specific Example—Preparation of 4,6-dibromo-5-ethyl-2 -phenylpyrimidine A mixture of 24.50 g (85.3 mmol) of phosphorus oxybromide, 7.56 g (37.3 mmol) of 5-ethyl-6-hydroxy-2-phenyl-4(3H)-pyrimidinone and 20 mL of 1,2-dichloroethane was heated at reflux for 2 h. After cooling to room temperature, the mixture was poured onto 300 g of crushed ice. The ice was allowed to melt, the mixture was basified by cautious addition of solid Na$_2$CO$_3$ and then extracted with two 200 mL portions of ethyl acetate. The combined ethyl acetate extracts were dried over MgSO$_4$ and concentrated to afford 11.79 g (92%) of crude 4,6-dibromo-5-ethyl- 2-phenylpyrimidine. This material was recrystallized from hexanes to furnish 6.62 g (52%) of pure product, mp 101°–103° C. $^1$H-NMR (CDCl$_3$)δ1.20(3H,t), 2.95(2H,q), 7.45(3H,m), 8.35(2H,m).

Method I—General Description 4,6-dihalopyrimidines are acidically hydrolyzed to give 6-halo-4(3H)-pyrimidinones. See U.S. Pat. No. 4,617,393.

Method I—Specific Example—Preparation of 6-bromo-5-ethyl-2-phenyl-4(3H)-pyrimidinone To 8.29 g (26.1 mmol) of crude 4,6-dibromo-5-ethyl-2-phenylpyrimidine was added a mixture of 4 mL of water and 15 mL of concentrated sulfuric acid. The mixture was stirred for 18 h and poured onto 200 g of crushed ice. After the ice had melted the precipitate was collected by filtration and dried under vacuum to afford 7.21 g (99%) of crude 6-bromo-5-ethyl-2-phenyl-4(3H)-pyrimidinone. $^1$H-NMR (d$^6$-DMSO)δ1.10(3H,t), 2.55(2H,q), 7.55(3H, m), 8.10(2H, m).

Method J—General Description:

Direct condensation of an amidine and an α-alkylidene malonate derivative is performed by stirring the reagents in a solvent such as DMF.

Method J—Specific Example—Preparation of 5-methoxycarbonyl-2-phenyl-6-trifluoromethyl-5,6-dihydro-4(3H)-pyrimidinone To 29.0 g (170 mmol) of 80% methyl 2-methoxycarbonyl-4,4,4-trifluorocrotonate in 100 mL of DMF was added a suspension of 29.8 g (170 mmol) of benzamidine hydrochloride and 14.3 g (170 mmol) of sodium bicarbonate in 200 mL of DMF. The reaction was stirred at room temperature overnight before quenching onto 600 mL of ice/water and collecting the resultant precipitate by vacuum filtration. The solid was washed with hexanes and dried at 60° C. in a vacuum oven overnight yielding 33.7 g (112 mmol) of white solid with mp 180°–182° C. 1H NMR (d6-acetone, 200 MHz)δ3.8(3H, s), 3.9(1H), d), 4.8(1H, m), 7.5(3H, m), 8.0(2H, dd), 11.0(1H, s, b).

Method K—General Description:

A dihydropyrimidinone with R5 as alkoxycarbonyl is dissolved in carbon tetrachloride and N-bromosuccinimide, a radical initiator and a base are added before refluxing the reaction. The base is usually potassium carbonate, benzoyl peroxide is the initiator and the reaction is generally complete within two hours.

Method K—Specific Example—Preparation of 5-methoxycarbonyl-2-phenyl-6-trifluoromethyl-4(3H)-pyrimidinone:

To 7.5 g (25 mmol) of 5-methoxycarbonyl-2-phenyl-6-trifluoromethyl-5,6-dihydro-4(3H)-pyrimidinone in 150 mL of carbon tetrachloride was added 4.45 g (25 mmol) of N-bromosuccinimide, 242 mg (1 mmol) of benzoyl peroxide and 34 g (250 mmol) of potassium carbonate and then refluxed for 2 hrs. The reaction is cooled to room temperature where it is quenched onto 400 mL of water. The layers are separated, aqueous is extracted with dichloromethane (2×300 mL), organics are combined, dried over $MgSO_4$ and evaporated to dryness in vacuo to give 6.55 g (21.9 mmol, 88%) of a white solid with mp 200°–203° C. 1H NMR ($d^6$-acetone)δ3.9(3H, s), 7.7(3H,m), 8.3(2H,d).

Method L—General Procedure:

A THF solution of pyrimidinone is added dropwise to a cold solution of a hydride reducing agent in an inert solvent, preferably lithium borohydride in THF and stirred at 0° C. The reaction does not generally go to completion and if it is allowed to run until the pyrimidinone is consumed, byproducts begin to form.

Unreacted pyrimidinone is recycled.

Method L—Specific Example—Preparation of 5-hydroxymethyl-2-phenyl-6-trifluoromethyl-4(3H)-pyrimidinone:

To 1.4 g (64.4 mmol) of lithium borohydride in 50 mL of THF at 0° C. was added dropwise a solution of 6.4 g(21.5 mmol) of 5-methoxycarbonyl-2-phenyl-6-trifluoromethyl-4(3H)-pyrimidinone in 50 mL of THF. Stirred at 0° C. for 4 hrs before quenching carefully onto 400 mL of water. The mixture was diluted with 200 mL of ethyl acetate and carefully acidified to pH=3 with conc. HCl before extracting with ethyl acetate (3×200 mL). Organic phases were combined, dried over sodium sulfate, filtered and evaporated to dryness in vacuo. The residue was triturated with ethyl acetate (100 mL) and the solid product collected by vacuum filtration. The filtrate may be evaporated to dryness in vacuo to obtain recovered starting material. Yield: 3.5 g (12.95 mmol, 60%) of a white solid with mp>215° C. 1H NMR (d6-acetone)δ4.7 (2H, s), 7.6 (3H,m), 8.3 (2H, d).

Method M—General Procedure:

A pyrimidinone with a formyl substituent is dissolved in a solvent mix and reacted with base and an alkoxylamine or hydroxylamine hydrochloride. The solvent is preferably a 1:1 mix of DMF and toluene, the base is triethylamine and the reaction is carried out between room temperature and 70° C.

Method M—Specific Example—Preparation of 5-methoximino-2-phenyl-3-propargyl-6-trifluorom-ethyl-4(3H)-pyrimidinone (Compound 248):

To 700 mg of 5-formyl-2-phenyl-3-propargyl-6-trifluoromethyl-4(3H)-pyrimidinone in 30 mL of 1:1 toluen:DMF was added 398 mL (2.68 mmol) of triethylamine and 239 mg (2.86 mmol) of methoxylamine hydrochloride and heated at 70° C. for 4 hrs. After cooling to room temperature the reaction is quenched with water (30 mL), the layers are separated and the aqueous extracted with ethyl acetate (3×30 mL). The organics are combined, washed with water (3×30 mL) and saturated sodium chloride (1×30 mL) before drying over $MgSO_4$, filtering and evaporating to dryness in vacuo to give 600 mg (1.79 mmol, 78%) of product as an off-white solid with mp 131°–132° C. 1H NMR ($CDCl_3$)δ2.45 (1H, t), 4.0 (3H, s), 4.65 (2H, d), 7.6 (3H, m), 7.8 (2H, m), 8.25 (1H,s).

Method Y1

(a) Preparation of 5-bromo-2-phenyl-6-trifluoromethyl 4(3H)-pyrimidinone.

To a solution of 1.0 g (3.94 mmol) of 2-phenyl-6-trifluoromethyl-4(3H)-pyrimidinone and 20 mL of glacial acetic acid was added 1.0 g (5.6 mmol) N-bromosuccinimide and the mixture was left to stir at room temperature for 16 h. The reaction was poured onto ice water and vacuum filtered, washing well with water. The crude product was recrystallized from ethyl acetate to yield 1.05 g (83.5%) of 5-bromo-2-phenyl-6-trifluoromethyl-4(3H)-pyrimidinone, as a white solid. $^1$H-NMR ($d_6$DMSO)δ7.6 (3H, m); 8.15 (2H, m).

(b) Preparation of 5-bromo-2,6-diphenyl-4(3H)-pyrimidinone.

To a suspension of 13.37 g (56 mmol) of 2,6-diphenyl-4(3H)-pyrimidinone and 200 mL glacial acetic acid was added 15.1 g (84.8 mmol) of N-bromosuccinimide and the mixture was left to stir at room temperature for 60 h. The reaction was poured onto 100 g crushed ice and vacuum filtered, washing well with water, then air dried to yield 8.85 g (48%) 5-bromo-2,6 -diphenyl-4(3H)-pyrimidinone, as a white solid. $^1$H-NMR ($d_6$DMSO)δ7.55 (6H, m); 7.75 (2H, m); 8.15 (2H, m).

Method Y2—Preparation of 6-ethyl-5-iodo-2-phenyl-4(3H)-pyrimidinone

A mixture of 8.18 g (40.9 mmol) of 6-ethyl-2-phenyl-4(3H)-pyrimidinone, 1.68 g (42.0 mmol) of sodium hydroxide, 10.42 g (41.0 mmol) of iodine and 50 mL of water was heated at 50° C. for 4 h. The mixture was cooled and filtered. The white solid collected was dried in a vacuum oven to leave 12.60 g (75%) of 6-ethyl-5-iodo-2 -phenyl-4(3H)-pyrimidinone. $^1$H-NMR (d6-DMSO)δ1.25(3H,t), 2.85(2H, q), 7.50(3H,m), 8.15(2H,m).

Method Y3—Preparation of 4,6-difluoro-5-ethyl-2-phenyl-pyrimidinone.

To a stirred solution of 3.14 g (12.41 mmol) portion of 4,6-dichloro-5 -ethyl-phenylpyrimidine in 25 mL of sulfolane at 70°–80° C. was added 6.37 g (109.8 mmol) of spray-dried potassium fluoride. The mixture was heated at 200° C. for 0.5 h. After cooling, the mixture was diluted with 100 mL of water and extracted with 400 mL of 1:1 ether-:hexanes. The organic layer was washed with two 100 mL portions of water, dried over $MgSO_4$ and concentrated to give 2.30 g of crude product. This material was combined with 0.29 g of crude product from another run and purified by flash chromatography on a column of 40 g of silica gel. The column was eluted with 0, 5, 10, 15 and 20% ether in hexanes to furnish 2.18 g (71%) of 4,6-difluoro-5-ethyl-2phenylpyrimidine as a white solid, m.p. 49°–51° C. $^1$H-NMR ($CDCl_3$)δ1.2(3H, t), 2.65(2H,q), 7.50(3H,m), 8.4(2H,m).

Method Y4—Preparation of 5-Chloro-6-ethyl-2-phenyl-

4(3H)-pyrimidinone

A stirred solution of 7.81 g (39.1 mmol) of 6-ethyl-2-phenyl-4(3H)-pyrimidinone and 5.80 g (43.4 mmol) of N-chlorosuccinimide in 100 mL of glacial acetic acid was heated at 90° C. for 4 h. The mixture was cooled, poured onto crushed ice and allowed to stand until the ice had melted. The mixture was filtered and the solid collected was washed with water and a little ether. The solid was dried in a vacuum oven at 50° C. to afford 7.99 g of 5-chloro-6-ethyl-2-phenyl-4(3H)-pyrimidinone (an intermediate for compound 172) as a white solid. $^1$H-NMR (d6-DMSO) 1.30(3H,t), 2.8(2H,q), 7.6(3H,m), 8.2(2H.m).

Method Y5 —Preparation of 6-phenoxy-2-phenyl-4(3H)-pyrimidinone

A solution of 4.28 g (40.4 mmol) of sodium carbonate and 7.53 g (40.1 mmol) of 4,6-dihydroxy-2-phenylpyrimidine in 100 mL of water was prepared and added to a stirred solution of 4.27 g (40.3 mmol) of sodium carbonate and 12.90 g (40.1 mmol) of iodobenzene diacetate in 100 mL of water. The mixture was heated at 40° C. for 3 h and allowed to cool. The white precipitate was collected by filtration and dried in a vacuum oven for 3 days to afford 13.00 g of crude 6-oxy-2-phenyl-5-phenyliodonium-4(3H)-pyrimidinone. This material was heated at reflux in 50 mL of DMF for 2 h. The mixture was cooled, poured into 500 mL of water and allowed to stand. The orange solid was collected by filtration and dried in a vacuum oven to afford 8.54 g of crude 5-iodo-6-phenoxy-2-phenyl-4(3H)-pyrimidinone.

A mixture of 7.07 g (18.1 mmol) of crude 5-iodo-6-phenoxy-2-phenyl-4(3H)-pyrimidinone, 2.02 g (31.1 mmol) of zinc dust and 25 mL of glacial acetic acid was heated to reflux. After 15 min an additional 2.06 g (31.7 mmol) of zinc dust was added, followed 15 min later by a further 2.04 g (31.4 mmol) of zinc dust. The mixture was maintained at reflux for 2 h, cooled and filtered to remove unreacted zinc. The filtrate was rotovaped to leave a semi-solid which was triturated with 75 mL of boiling water to afford 6.01 g (57% from 4,6-dihydroxy-2-phenylpyrimidine) of 6-phenoxy-2-phenyl-4(3H)-pyrimidinone as a yellow solid. 1H-NMR (d6-DMSO)δ5.5 (1H,s), 7.1–7.5 (8H), 8.1 (2H).

Method Z1—Preparation of 6-dimethylaminocarbonyl-5-methyl- 2-phenyl-3-propargyl-4(3H)-pyrimidinone. (Compound 19)

To a solution of 1.81 g (6.1 mmol) of 6-ethoxycarbonyl-5-methyl-2-phenyl- 3-propargyl-4(3H)-pyrimidinone in 100 mL of ethanol and 50 mL of THF was added 50 mL of 5% aqueous sodium hydroxide. The mixture was stirred at room temperature for 24 h and rotovapped to remove the bulk of the organic solvents. The residue was diluted with 50 mL of 5% aqueous sodium hydroxide and washed with 100 mL of ether. The aqueous phase was acidified with concentrated hydrochloric acid and extracted with two 100 mL portions of ethyl acetate. The combined ethyl acetate extracts were washed with 50 mL of brine, dried over MgSO$_4$ and concentrated to leave 0.87 g (53%) of crude 6-carboxy-5-methyl-2-phenyl-3 -propargyl-4(3H)-pyrimidinone as a brown oil.

To a stirred solution of 0.87 g (3.2 mmol) of crude 6-carboxy-5-methyl-2 -phenyl-3-propargyl-4(3H)-pyrimidinone, 0.32 g (3.9 mmol) of dimethylamine hydrochloride and 2 mL of pyridine in 10 mL of THF was added 0.74 g (3.6 mmol) of solid N,N'-dicyclohexylcarbodiimide. The mixture was stirred at room temperature for 4 days and filtered to remove insoluble material. The filtrate was diluted with 150 mL of ethyl acetate, washed with 50 mL of 5% aqueous HCl and 50 mL of saturated aqueous sodium bicarbonate and dried over MgSO$_4$. Removal of the solvent left 0.40 g of crude product which was purified by flash chromatography on a 30 g column of silica gel, eluted with 60, 80 and 100% ethyl acetate in hexanes to furnish 0.30 g (32%) of 6-dimethylaminocarbonyl-5-methyl-2-phenyl-3-propargyl-4(3H)-pyrimidinone (compound 19), mp 137°–140° C. $^1$H-NMR (CDCl$_3$)δ2.15(3H,s), 2.40(1H, t), 3.00(3H,s), 3.10(3H,s), 4.65(2H,d), 7.55(3H,m), 7.70 (2H,m).

Method Z2—Preparation of 6-dimethylamino-5-methyl-2-phenyl-3-propargyl-4(3H)-pyrimidinone. (Compound 23)

To an ice cooled solution of 1.5 g (3.8 mmol) 6-chloro-5-methyl-2-phenyl- 3-propargyl-4(3H)-pyrimidinone in 4 mL of tetrahydrofuran, was added 22 mL (99 mmol) of 4.5M dimethylamine in ether portionwise (2–4 mL) over a period of 7 days. The reaction mixture was allowed to warm and stir at room temperature after each addition. The progress of the reaction was followed by gas chromatography and proceeded to 80% completion. The solvent was removed in vacuo and the residue was taken up in ether and washed twice with water. The organic layer was dried over MgSO$_4$ and concentrated to yield 1.15 g crude solid product. Flash column chromatography on silica gel (gradient elution 25–30% ethyl acetate-hexane) afforded pure 6-dimethylamino-5-methyl-2-phenyl-3-propargyl-4(3H)-pyrimidinone (compound 23), as a white solid. $^1$H-NMR (CDCl$_3$)δ2.2 (3H, s); 2.35 (1H, t); 3.5 (6H, s); 4.6 (2H, d); 7.65 (3H, m); 7.75 (2H, m).

Method Z3—Preparation of 5-Ethyl-3-(2-oxopropyl)-2-phenyl-6-trifluoromethyl( 4(3H)-pyrimidinone (Compound 179)

To a stirred solution of 4.83 g (15.8 mmol) of 5-ethyl-3-propargyl-2-phenyl-6 -trifluoromethyl-4(3H)-pyrimidinone (compound 46) in 50 mL of THF was added 50 mL of 10% aq NaOH. The mixture was heated at reflux for 2 h, cooled and diluted with 150 mL of ethyl acetate. The organic layer was separated, washed with 50 mL of water and 50 mL of brine and dried over MgSO$_4$. Removal of the solvent afforded 4.74 g of 5-ethyl-3-(2-oxopropyl)-2-phenyl-6-trifluoromethyl-4(3H)-pyrimidinone (compound 179) as a white solid. $^1$H-NMR (CDCl$_3$) 1.2(3H), 2.2(3H,s), 2.7(2H, q), 4.7(2H,s), 7.45(5H,m).

Method Z4—Preparation of 5-methyl-2-phenyl-3-propargyl-6-methylthio-4(3H)-pyrimidinone. (Compound 26)

To a solution of 2.5 g (9.67 mmol) of 6-chloro-5-methyl-2-phenyl-3 -propargyl-4(3H)-pyrimidinone in 100 mL of methanol, was added 0.8 g (11.4 mmol) sodium thiomethoxide and the reaction was stirred at room temperature for 4 days. The methanol was evaporated and the residue was dissolved in 100 mL of ethyl acetate, then washed three times with 50 mL of 1M sodium hydroxide followed by one time with 50 mL of brine. The organic layer was dried over MgSO$_4$ and concentrated to yield 2.6 g crude product. Flash column chromatography on silica gel (100% methylene chloride) afforded 5-methyl-2-phenyl-3-propargyl-6-thiomethyl- 4(3H)-pyrimidinone (Compound 26) as a white solid. $^1$H-NMR (CDCl$_3$)δ2.1 (3H, s); 2.35 (1H, t); 2.5 (3H, s); 4.55 (2H, d); 7.5 (3H, m); 7.7 (2H, m).

Method Z5—Preparation of 3-(2,2-dimethoxypropyl)-6-ethyl-5-methyl-2-phenyl- 4(3H)-pyrimidinone (Compound 36)

To a stirred suspension of 4.51 g (17.9 mmol) of 6-ethyl-5-methyl-2-phenyl 3-propargyl-4(3H)-pyrimidinone (Compound 5) in 30 mL of methanol was added 7.50 g (34.7 mmol) of a 25% by weight solution of sodium methoxide in methanol. The mixture was warmed until homogeneous and 2.2 mL (35.3 mmol) of methyl iodide was added. The mixture was refluxed for 4 h and then rotovapped to remove the bulk of the methanol. The residue was partitioned between 100 mL of water and two 100 mL portions of ether. The combined ether layers were washed with 50 mL of brine and dried over MgSO$_4$. Removal of the solvent afforded 4.35 g of a yellow oil. Flash chromatography on a column of 50 g of silica gel, eluting with 20, 30, 40 and 50% ether in hexanes furnished 3.30 g (58%) of 3-(2,2-dimethoxypropyl)-6-ethyl-5-methyl-2-phenyl-4(3H)-pyrimidinone (compound 36), mp 80°–83° C. $^1$H-NMR (CDCl$_3$)δ1.15(3H,s), 1.25(3H, t), 2.15(3H,s), 2.65(2H,q), 2.85 (6H,s), 4.4(2H,m), 7.45(5H,s).

Method Z6—Preparation of 3-methoxymethyl-2-phenyl-6-trifluoromethyl-4(3 H)-pyrimidinone (Compound 6)

To a solution of 1.5 g (5.9 mmol) of 2-phenyl-6-trifluoromethyl-4(3H)-pyrimidinone, 17.2 g (226.3 mmol) dimethoxymethane, and 35 mL of chloroform was added 2.5 g (17.6 mmol) phosphorous pentoxide, at room temperature. By TLC (25% ethyl acetate in hexane) the reaction was incomplete after 4 h and an additional 3 g (21.1 mmol) phosphorous pentoxide was added. Stirring was continued for 16 h. The reaction mixture was poured onto crushed ice and 1M sodium hydroxide and methylene chloride were added. The layers were separated and the aqueous layer was extracted twice with methylene chloride. The organic extracts were combined and washed with brine, then dried over MgSO$_4$ and concentrated to yield 1.1 g crude product, which was purified by recrystallization from hexane. Thus, 0.55 g (32%) 3-methoxymethyl-2-phenyl-6-trifluoromethyl-4(3H)-pyrimidinone (Compound 6) as a yellow solid was obtained. $^1$H-NMR (CDCl$_3$)δ3.55 (3H, s); 5.2 (2H, d); 6.85 (1H, s); 7.65 (3H, m); 7.75 (2H, m).

Method Z7—Preparation of 6-ethyl-2-phenyl-3-propargyl-5-(2-trimethylsilylethynyl)- 4(3H)-pyrimidinone (Compound 92)

To a stirred solution of 3.59 g (9.86 mmol) of 6-ethyl-5-iodo-2-phenyl-3-propargyl-4(3H)-pyrimidinone and 16.45 g (167.5 mmol) of trimethylsilylacetylene in 40 mL of DMF were added 1.13 g (0.98 mmol) of tetrakis(triphenylphosphine) palladium(0), 0.41 g (2.15 mmol) of copper (I) iodide and 2.8 mL (20.0 mmol) of triethylamine. The mixture was stirred at room temperature for 18 h, diluted with 200 mL of water and extracted with two 200 mL portions of ether. The combined ether extracts were dried over MgSO$_4$ and evaporated under reduced pressure to leave 5.71 g of a black oil. This material was subjected to flash chromatography on a column of 50 g of silica gel, eluted with 0, 10, 20, 30, 40, 50, 60 and 80% ether in hexanes to afford 0.80 g of material. Further purification was effected by chromatography on a column of activity I alumina eluted with 0, 10, 20, 35, 50, 75 and 100% ether in hexanes. This process yielded 0.43 g (13%) of 6-ethyl-2-phenyl-3-propargyl-5-(2-trimethylsilylethynyl)-4(3H)-pyrimidinone as an oil. $^1$H-NMR (CDCl3)δ0.25(9H,s), 1.25(3H, t), 2.37(1H,t), 2.85(2H,q), 4.60 (2H,d), 7.55(3H,m), 7.75(2H,m).

Method Z8—5-Ethyl-2-(1-oxo-4-pyridyl)-3-propargyl-6-trifluoromethyl-4(3H)-pyrimidinone (Compound 133)

To a stirred suspension of 8.54 g (27.8 mmol) of -5-ethyl-3-propargyl-2-(4-pyridyl)-6-trifluoromethyl-4(3H)-pyrimidinone (compound 58) in 50 mL of ethanol was adsded 9.07 g (18.3 mmol) of monoperoxyphthalic acid magnesium salt hexahydrate. The mixture was stirred at room temperature for 24 h. The bulk of the ethanol was removed on the rotovap and the residue was partitioned between 150 mL of ethyl acetate and 75 mL of 5% aqueous hydrochloric acid. The organic layer was washed with two 75 mL portions of saturated aqueous NaHCO$_3$, dried MgSO$_4$ and concentrated to leave 8.42 g of 5-ethyl-2-(1-oxo-4-pyridyl)-3-propargyl-6-trifluoromethyl-4(3H)-pyrimidinone (compound 133) as a yellow solid. $^1$H-NMR (CDCl$_3$) 1.25(3H, t), 1.30(3H, t), 2.60(1H,t), 2.8(4H,m), 4.7(2H,d), 7.8(2H,d),8.35(2H,d).

Method Z9—Preparation of 2-(2-Cyano-4-pyridyl)75-ethyl-3-propargyl-6-trifluoromethyl-4(3H)-pyrimidinone (Compound 141)

To a stirred solution of 6.96 g (21.6 mmol) of 5-ethyl-2-(1-oxo-4-pyridyl)-3-propargyl-6-trifluoromethyl-4(3H)-pyrimidinone and 6.0 mL (42.8 mmol) of triethylamine in 20 mL of acetonitrile was added 11.5 mL (86.3 mmol) of trimethylsilyl cyanide. The mixture was heated at reflux for 4 h. After standing overnight, the mixture was diluted with 150 mL of ether, washed with three 50 mL portions of water and dried over MgSO$_4$. Removal of the solvent left 4.94 g of crude product as a black tar. This material was purified by flash chromatography on 60 g of silica gel, eluting with 0, 20, 35, 50, 65, 80 and 100% ether in hexanes to furnish 1.78 g of 2-(2-cyano-4-pyridyl)-5-ethyl-3-propargyl-6-trifluoromethyl-4(3H)-pyrimidinone (compound 141) as a solid. $^1$H-NMR (CDCl$_3$) 1.25(3H, t), 2.60(1H,t), 2.8(2H,q), 4.6(2H,d), 8.0 (1H,d), 8.10(1H,s), 9.0(1H,d).

Method Z10—Preparation of 2-phenyl-3,5,6-triethyl-4(3H)-pyrimidinethione (Compound 124)

A mixture of 1.0 g (3.9 mmol) 2-phenyl-3,5,6-triethyl-4(3H)-pyrimidinone, 0.87 g (2.1 mmol) Lawesson's reagent and 35 mL toluene was refluxed for 20 h. By TLC (20% ethyl acetate-hexane) the product was more polar than the starting material. The reaction was incomplete and an additional 1.2 g (2.96 mmol) of Lawesson's reagent was added and refluxing was continued for 16 h. The solvent was removed in vacuo to leave 2.2 g yellow wet solid. Flash column chromatography on silica gel (20% ethyl acetate in hexane) afforded 0.5 g of material containing the thione, which was again purified by flash chromatography (5% ethyl acetate-hexane) to yield 280 mg (26.4%) of 2-phenyl-3,5,6-triethyl-4(3H)-pyrimidinthione (compound 124), as an oil. $^1$H-NMR (CDCl$_3$)δ1.25 (9H, m); 2.7 (2H, q); 3.05 (2H, q); 4.6 (2H, q); 7.5 (5H, m).

Method Z11—Preparation of 5,6-Diethyl-2-phenyl-3-(3-trimethylsilylprop2-ynyl)- 4(3H)-pyrimidinone (Compound 182)

To an oven-dried 50 mL 3-neck flask were charged 0.9 g (3.38 mmol) of 5,6-diethyl-2-phenyl-3-propargyl-4(3H)-pyrimidinone and 25 mL freshly distilled THF. The solution was cooled to −70° C. and 2.2 mL of 1.6M (3.52 mmol) n-butyllithium in hexane was added at a rate to maintain the temperature below −62° C. during the addition. The reaction mixture turned black and was allowed to stir for 12 minutes at −70° C. A 0.47 mL (3.70 mmol) portion of trimethylsilyl chloride was added and the reaction stirred for 20 minutes at −70° C. The dry ice bath was removed and the reaction was left to stir and warm to room temperature overnight. The THF was removed in vacuo and ether was added. The ether solution was washed 3 times with water then dried over MgSO$_4$ and concentrated to yield 1.2 g of crude product, as a brown oil. The crude product was purified by chromatography on a 30 g silica gel column eluting with 18% ethyl acetate in hexane. 0.8 g (70% yield) of 5,6-diethyl-2-phenyl-3-(3-trimethylsilyl-2-propynyl)-4(3H)-pyrimidinone (compound 182), was obtained as a yellow oil. $^1$H-NMR (CDCl$_3$) 0.18(9H,s), 1.25(6H,m), 2,65(4H, q), 4.6(2H,s), 7.6(3H,m), 7.42–7.8(5H,m)

Method Z12—Preparation of 5-ethyl-3-(pent-2-yn-4-en-1-yl)-2-phenyl- 6-trifluoromethyl-4(3H)-pyrimidinone (Compound 111)

To a deoxygenated solution of 1.01 g (3.28 mmol) of 5-ethyl-2-phenyl-3-propargyl-6-trifluoromethyl-4(3H)-pyrimidinone and 0.61 g (3.96 mmol) of vinyl iodide in 25 mL of triethylamine was added a mixture of 60 mg of copper (I) iodide and 60 mg of bis(triphenylphosphine) palladium (II) chloride. The mixture was stirred at room temperature for 22 h and rotovapped to remove the bulk of the triethylamine. The residue was taken up in 150 mL of ethyl acetate, washed with 75 mL of 5% aqueous hydrochloric acid, 75 mL of saturated aqueous sodium bicarbonate and 75 mL of brine, and dried. Removal of the solvent left 1.51 g of a brown tar. Flash chromatography on a column of 30 g of silica gel eluting with 20, 40, 60 and 60% ether in hexanes afforded 0.31 g of crude 5-ethyl-3-(pent-2-yn-4 -en-1 -yl)-2-phenyl-6-trifluoromethyl-4(3H)-pyrimidinone. A second chromatography yielded 0.25 g (23%) of pure 5-ethyl-3-(pent-2-yn-4-en-1-yl)-2-phenyl-6 -trifluoromethyl-4(3H)-pyrimidinone (compound 111) as a solid, mp 104°–106° C. $^1$H-NMR (CDCl$_3$) d 1.25(3H,t), 2.8(2H, q), 4.75(2H,s), 5.5–5.9(3H,m), 7.55(3H,m) 7.7(2H,m).

Z13—Preparation of 2-(1-methyl-3-pyridinium)-5-ethyl-3-propargyl 6-trifluoromethyl-4(3H)-pyrimidinone iodide (Compound 61)

A solution of 1.23 g (4.01 mmol) of 5-ethyl-3-propargyl-2-(3-pyridyl)-6 -trifluoromethyl-4(3H)-pyrimidinone and 1.0 mL (16.1 mmol) of methyl iodide in 5 mL of CHCl$_3$ was heated at reflux for 6 h. An additional 1.0 mL portion of methyl iodide was added and refluxing was continued overnight. The mixture was rotovapped to leave 1.86 g of 2-(1-methyl-3-pyridinium)-5-ethyl-3-propargyl-6 -trifluoromethyl-4(3H)-pyrimidinone iodide as a brown solid. $^1$H-NMR (CDCl$_3$)δ 1.2(3H, t), 2.7(1H, t), 2.75(2H,q), 4.65(3H, s), 4.9(2H,d), 8.4(1H,t), 8.9(1H, d), 9.2(1H, s), 9.5(1H,d).

Method Z14—Preparation of 5,6-diethyl-2-(3-formylphenyl)-3-propargyl-4(3H)-pyrimidinone (Compound 69)

To a solution of 2.3 g (6.8 mmol) of 5,6-diethyl-2-[3-(2-dioxolanyl)phenyl]- 3-propargyl-4(3H)-pyrimidinone in 1 mL of ethyl acetate was added 50 mL of 6M hydrochloric acid and the mixture was stirred for 4 hours. The reaction was followed by gas chromatography and TLC(20% ethyl acetate in hexane). Upon completion of reaction, 75 mL of ether and 150 mL of water were added to the reaction mixture. The layers were separated and the aqueous layer was extracted twice with 50 mL of ether. The organic layers were combined, dried over MgSO$_4$ and concentrated to yield 1.73 g of 5,6-diethyl-2-(3-formylphenyl)-3-propargyl-4(3H)-pyrimidinone (Compound 69) as a yellow oil (86%), which solidified on standing. Mp.=82°–86° C. $^1$H-NMR (CDCl$_3$)δ1.25(6H,m), 2.4(1H, t), 2.65(4H,q), 4.6(2H,d), 7.7(1H, t), 8.05(2H,m), 8.25(1H,s), 10.15(1H,s).

Method Z15—Preparation of 3,6-diethyl-2-phenyl-5-trifluoromethyl- 4(3H)-pyrimidinone (Compound 185)

A mixture of 1.00 g (2.5 mmol) of 3,6-diethyl-5-iodo-2-phenyl-4(3H)-pyrimidinone, 1.08 g (5.7 mmol) of copper (I) iodide, 1.54 g (11.3 mmol) of sodium trifluoroacetate and 8 mL of anhydrous N-methylpyrrolidinone was heated at 175° C. for 2 h. The mixture was cooled, diluted with 175 mL of ether, washed with four 50 mL portions of water and dried over MgSO$_4$. Removal of the solvent on the rotovap afforded 0.92 g of crude product as a brown oil. This material was purified by flash chromatography on a 25 g column of silica gel eluting with 100 mL portions of 0, 10, 20, 30, 40, 50 and 75% ether in hexanes to afford 0.35 g of 3,6-diethyl-2-phenyl-5-trifluoromethyl-4(3H)-pyrimidinone (compound 185) as a white solid. $^1$H-NMR (CDCl$_3$) 1.25(3H,t), 1.30(3H,t), 2.8(2H,q), 4.0(2H, q), 7.5(5H).

Method Z16—Preparation of 5,6-Diethyl-2-(3-hydroxyiminophenyl)-3-propargyl- 4(3H)-pyrimidinone (Compound 139)

To a 100 mL RBF were charged 1.1 g (3.7 mmol) of 5,6-diethyl-2-(3-formyl-phenyl)-3 -propargyl-4(3H)-pyrimidinone, 0.52 g (7.5 mmol) of hydroxylamine hydrochloride and 50 mL of ethanol. The reaction mixture was refluxed for 17 hours. The ethanol was removed in vacuo and ether and ethyl acetate were added to the residue. The organics were washed 3 times with water. The organic layer was gravity filtered to remove 0.22 g of 5,6-diethyl-2-(3-hydroxyiminophenyl)-3-propargyl-4(3H)-pyrimidinone (compound 139). The organic layer was dried over MgSO$_4$ and concentrated to yield a further 0.67 g of 5,6-diethyl-2-(3-hydroxyiminophenyl)-3 -propargyl-4(3H)-pyrimidinone (compound 139) as a white solid. A combined yield of 77.6% was obtained. $^1$H-NMR (CDCl$_3$) 1.25(6H,m); 2.35(1H,t); 2.65(4H,m); 4.6(2H,d); 7.49–8.15(4H,m); 8.7(1H,s)

Method Z17—Preparation of 5,6-Diethyl-2-(3-cyanophenyl)-3-propargyl-4(3H)-pyrimidinone (Compound 137)

To an ice cooled solution of 0.64 g (2.07 mmol) of 5,6-diethyl-2-( 3-hydroxyiminophenyl)-3-propargyl-4(3H)-pyrimidinone in 10 mL methylene chloride, 1.5 mL (20.5 mmol) of thionyl chloride was added dropwise. The ice bath was removed and the reaction continued to stir at room temperature for 16 h. The reaction mixture was concentrated and 10 mL portions of methylene chloride were added and removed in vacuo twice. 0.65 g of a light brown solid was obtained as crude product. This was combined with 0.15 g crude product from a previous run. The crude product was purified by passing it through a 4 inch plug of basic alumina and washing with 700 mL of methylene chloride. 400 mg of 5,6-diethyl-2-( 3-cyanophenyl)-3-propargyl-4(3H)-pyrimidinone (compound 137) was obtained. $^1$H-NMR (CDCl$_3$) 1.25(6H,m); 2.4(1H,t); 2.65(4H,m); 4.58(2H,d); 7.64–8.1(4H,m).

Method Z18—Preparation of 5-ethyl-3-(3-iodopropargyl)-2-phenyl-6-trifluoromethyl- 4(3H)-pyrimidinone (Compound 219)

A stirred solution of 1.53 g (5.0 mmol) of 5-ethyl-2-phenyl-3-propargyl- 6-trifluoromethyl- 4(3H)-pyrimidinone (Compound 46) in 30 mL of THF was cooled to −70° C. and 4.5 mL of 1.6M n-BuLi in hexanes (7.2 mmol) was added dropwise over 15 min. The mixture was stirred at −70° C. for 45 min and a solution of 1.50 g (6.7 mmol) of N-iodosuccinimide in 10 mL of THF was added dropwise over 15 min. The mixture was stirred at −70° C. for 45 min and at room temperature for 30 min. The mixture was diluted with 175 mL of ether, washed with two 50 mL portions of water and 50 mL of saturated aqueous NaHCO$_3$ and dried over MgSO$_4$. Removal of the solvent left 2.36 g of crude product as a brown solid which was purified by flash chromatography on 30 g of silica gel, eluting with 0, 10, 20, 30 and 40% ether in hexanes, to furnish 0.96 g (44%) of 5-ethyl-3-(3-iodopropargyl)-2-phenyl-6 -trifluoromethyl-4(3H)-pyrimidinone (Compound 219) as a an off-white solid, m.p. 120°–125° C (dec). $^1$H-NMR (CDCl$_3$)δ1.25(3H, t), 2.75(2H,q), 4.75 (2H,s), 7.5–7.7 (5H).

Method Z19—General Procedure:

An hydroxymethylpyrimidinone is reacted with a methylating agent, preferably dimethyl sulfate, using phase transfer conditions between an inert solvent, preferably dichloromethane, and basic water in the presence of a quarternary ammonium catalyst, usually benzyltriethylammonium chloride.

Method Z19—Specific Example-Preparation of 5-methoxymethyl-2-phenyl-3-propargyl-6-trifluoromethyl-4(3H)-pyrimidinone (Compound 240):

To 0.22 mL (2.38 mmol) of dimethyl sulfate in 7 mL of dichloromethane was added in rapid succession 272 mg (3.4 mmol) of 50% sodium hydroxide, 1 mL of water, a catalytic amount of benzyltriethylammonium chloride and 700 mg (2.27 mmol) of 5-hydroxymethyl-2-phenyl-3-propargyl-6-trifluoromethyl-4(3H)-pyrimidinone. The reaction was stirred at room temperature overnight before quenching onto water (30 mL). The layers were separated and the aqueous extracted with dichloromethane (2×30 mL). Organics were combined, dried over MgSO$_4$, filtered and evaporated to dryness in vacuo. The product was purified by medium pressure liquid chromatography in 2:1 hexanes/ethyl acetate to give 200 mg (0.62 mmol, 27%) of a white solid with mp 131°–132° C. 1H NMR (CDCl$_3$) d 1.45 (1H, t), 3.5 (3H, s), 4.6 (2H,s), 4.7 (2H, d), 7.6 (3H, m), 7.8 (3H, m).

Method Z20—General Procedure:

An hydroxymethylpyrimidinone in an inert solvent such as dichloromethane is added dropwise at low temperature, preferably −78° C., to a solution of diethylaminosulfur trifluoride in that same solvent and allowed to react.

Method Z20—Specific Example—Preparation of 5-monofluoromethyl-2-phenyl-3-propargyl-6-trifluoromethyl-4(3H)-pyrimidinone (Compound 241):

To 0.29 mL (365 mg, 2.27 mmol) of diethylaminosulfur trifluoride in 5 mL of dichloromethane at −78° C. was added dropwise over 0.5 hr a solution of 0.7 g (2.27 mmol) of 5-hydroxymethyl-2-phenyl-3-propargyl-6-trifluoromethyl-4(3H)-pyrimidinone in 10 mL of dichloromethane. After addition was complete the reaction was stirred at −78° C. for 0.5 hr before warming to room temperature and carefully quenching onto 100 mL of ice. Layers were separated and the aqueous extracted with ethyl acetate (2×50 mL). Organics were combined, dried over MgSO$_4$, filtered and evaporated to dryness in vacuo to give 520 mg (1.78 mmol, 79%) of a white solid with mp 134°–135° C. $^1$H NMR (CDCl$_3$)δ2.8 (1H, t, J=2.4 Hz), 5.0 (2H, d, J=2.4 Hz), 5.9 (2H,dd, J=46.8, 1.2 Hz), 7.9 (3H,m), 8.1 (2H, m).

Method Z22— 2-(2,6-dichloro-4-pyridyl)-6-ethyl-5-methoxy-3-(2-oxo-propyl)-4(3H)-pyrimidinone (Compound 221)

1.0 g of crude 2-(2,6-dichloro-4-pyridyl)-6-ethyl-5-methoxy-3-propargyl-4(3H) pyrimidinone (compound 199) was dissolved in a minimal amount of methylene chloride and vacuum filtered through a four inch plug of neutral alumina, washing with 500 mL of methylene chloride followed by 500 mL of ether. After standing for 64 h, the alumina was washed with 500 mL of THF. Removal of the THF left 1.0 g of a solid residue. The residue had 2 spots by TLC (20% EtOAC/Hexane) and was purified on a 40 g silica gel column using 30% EtOAC/Hexane. By TLC, the less polar spot corresponded to Compound 199 and the more polar spot corresponded to Compound 221. 0.3 g of 2-(3,5-dichloro-4-pyridyl)6-ethyl-5-methoxy-3-(2-oxo-propane)-4(3H)-pyrimidinone (compound 221) was isolated as a solid. 1H-NMR (CDCl3) 1.25 (3H,t), 2.3(3H, s), 2.68(2H, q), 3.94(3H,s), 4.65(2H,s), 7.4(2H,s).

Method Z23—General Procedure:

An hydroxymethylpyrimidinone in a solvent such as dichloromethane is added at low temperature, preferably −50° to −60° C., to an activated dimethyl sulfoxide reagent in the same solvent. After stirring for a period of time a base, usually triethylamine, is added and the reaction is warmed to room temperature and the product isolated.

Method Z23—Specific Example—Preparation of 5-formyl-2-phenyl-3-propargyl-6-trifluoromethyl-4(3H)-pyrimidinone (Compound 246):

To 30 mL of dichloromethane at −60° C. was added 433 mL (630 mg, 4.96 mmol) of oxalyl chloride followed by the dropwise addition of 704 mL (755 mg, 9.92 mmol) of dimethyl sulfoxide. This mixture is stirred for 10 min before the addition of a solution of 1.39 g (4.5 mmol) of 5-hydroxymethyl-2-phenyl-3-propargyl-6-trifluoromethyl-4(3H)-pyrimidinone in 20 mL of dichloromethane. The reaction is stirred at −60° C. for one hour before adding dropwise 3.13 ml (2.28 g, 22.5 mmol) of triethylamine warming to room temperature and quenching with 20 mL of water. Layers are separated and the aqueous extracted with dichloromethane (2×30 mL). Organics are combined and washed with saturated sodium bicarbonate before drying over MgSO$_4$, filtering and evaporating to dryness in vacuo to give 1.22 g (3.98 mmol, 88%) of the product as a white solid with mp 110°–112° C. 1H NMR (CDCl3)d 2.5 (1H, t), 4.7 (2H, d), 7.6 (3H, m), 7.8 (2H, m), 10.4 (1H, s).

Method Z24—General Procedure:

A pyrimidinone with an aldehyde substituent is dissolved in an inert solvent and an alcohol, for example ethylene glycol, and acid catalyst are added before refluxing the mixture while removing water with a Dean-Stark apparatus. The usual solvent is toluene and the catalyst is toluensulfonic acid.

Method Z24—Specific Example—Preparation of 5-(1,3-dioxalan-2-yl)-2-phenyl-3-propargyl-6-trifluoromethyl-4(3H)-pyrimidinone (Compound 249):

To 650 mg (2.12 mmol) of 5-formyl-2-phenyl-3-propargyl-6-trifluoromethyl-4(3H)-pyrimidinone in 30 mL of toluene was added 130 mL (144 mg, 2.33 mmol) of ethylene glycol and a catalytic amount of toluensulfonic acid. The reaction was refluxed overnight while removing water with a Dean-Stark apparatus then cooled to room temperature, washed with saturated sodium bicarbonate (1×40 mL) and saturated sodium chloride (1×40 mL) before drying over MgSO$_4$, filtering and evaporating to dryness in vacuo to give 620 mg (1.85 mmol, 87%) of product as a white solid with mp 185°–187° C. 1H NMR (CDCl3) d 2.4 (1H, t), 4.1 (2H, t), 4.4 (2H,t), 4.6 (2H, d), 6.2 (1H, s), 7.55 (3H,m), 7.75 (2H, m).

Methods of Use.

In another aspect, this invention relates to a method of controlling weeds comprising applying to said weed or the locus of said weed or to the surface of the growth medium of said weed a herbicidally effective amount of a compound of the formula:

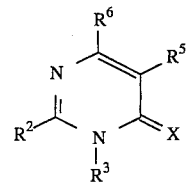

Ia wherein $R^2$ is a substituted or unsubstituted aryl group (e.g. aromatic ring structure having four to ten carbon atoms) or a substituted or unsubstituted heteroaromatic group (e.g. a heteroaromatic ring structure having four to five carbon atoms and one heteroatom selected from nitrogen, oxygen or sulfur); $R^3$ is an alkyl, haloalkyl, polyhaloalkyl, alkenyl, haloalkenyl, polyhaloalkenyl, alkynyl, haloakynyl, polyhaloalkynyl, alkenynyl, alkoxyalkyl, dialkoxyalkyl, haloalkoxyalkyl, oxoalkyl, trimethylsilyalkynyl, cyanoalkyl or aryl group; $R^5$ is a hydrogen, halogen, acyl, alkyl, alkenyl, alkynyl, alkoxy, alkylthio, alkoxyalkyl, alkoxyimino, alkoxycarbonylalkyl, dialkoxyalkyl, formyl, haloalkyl, haloalkenyl, haloalkynyl, haloalkoxy, hydroxyalkyl, hydroxyimino, polyhaloalkyl, polyhaloalkenyl, polyhaloalkynyl, polyhaloalkoxy, trimethylsilylalkynyl, or cyano group; and $R^6$ is a hydrogen, halo, alkyl, alkenyl, alkynyl, alkoxy, haloalkoxy, alkylthio, haloalkylthio, alkoxyalkyl, alkoxycarbonyl, alkoxycarbonylalkyl, haloalkyl, haloalkenyl, haloalkynyl, polyhaloalkyl, polyhaloalkenyl, polyhaloalkynyl, polyhaloalkoxy, polyhaloalkythio, cycloalkyl, aryl, heterocyclyl, aralkyl, aryloxy, alkylamino, dialkylamino, dialkylaminocarbonyl, or cyano group; the aryl, aralkyl and aryloxy groups may be substituted or unsubstituted; and X is oxygen or sulfur. The particulars as to the substituents and preferences therefore are the same as stated hereinabove in the compound embodiments. Such herbicidal compositions additionally can comprise one or more carriers suitable for herbicidal compositions.

The compounds of the invention are useful as preemergence and postemergence herbicides. In general, they require lower doses to control weeds preemergence. Preemergence herbicides are usually applied to the soil either before, during or after seeding, but before the crop emerges. Postemergence herbicides are applied after the plants have emerged and during their growth period. The embodied materials generally show selectivity to several agronomically important crops such as corn, cotton, rice, soybean, sugarbeet, sunflower, peanut and wheat.

Under some conditions the compounds of the invention may be incorporated into the soil or other growth medium prior to planting a crop. This incorporation may be by any convenient means, including mixing with the soil, applying the compound to the surface of the soil and then dishing or dragging into the soil to the desired depth, or by employing a liquid carrier.

The 2-arylpyrimidines of the present invention can be applied to various loci such the soil or the foliage. For such purposes these compounds can be used in the technical or pure form as prepared, as solutions or as formulations. The compounds are usually taken up in a carrier or are formulated so as to render them suitable for subsequent dissemination as herbicides. For example, these chemical agents can be formulated as wettable powders, emulsifiable concentrates, dusts, granular formulations, aerosols, or flowable emulsion concentrates. In such formulations, the compounds are extended with a liquid or solid carrier and, when desired, suitable surfactants are incorporated.

It is usually desirable, particularly in the case of foliar spray formulations, to include adjuvants, such as wetting agents, spreading agents, dispersing agents, stickers, adhesive and the like in accordance with agricultural practices. Such adjuvants commonly used in the art can be found in the John W. McCutcheon, Inc. publication "Detergents and Emulsifiers, Annual." Allured Publishing Company, Ridgewood, N.J., U.S.A.

The 2-arylpyrimidines can be applied as herbicidal sprays by methods commonly employed, such as conventional high-gallonage hydraulic sprays, low-gallonage sprays, airblast spray, aerial sprays and dusts. The dilution and rate of application will depend upon the type of equipment employed, the method of application and weeds to be controlled, but the preferred effective amount is usually from about 0.01 lb. to about 10 lbs. per acre of the active ingredient.

As a soil treatment the chemical can be incorporated in the soil or applied to the surface usually at a rate of from about 0.01 to about 10 lbs. per acre. As a foliar spray, the toxicant is usually applied to growing plants at a rate of from about 0.01 to about 10 lbs. per acre.

The 2-arylpyrimidines of the invention can also be mixed with fertilizers or fertilizing materials before their application. In one type of solid fertilizing composition in which the arylpyrimidines can be used, particles of a fertilizer or fertilizing ingredients, such as ammonium sulfate, ammonium nitrate, or ammonium phosphate, can be coated with one or more of the compounds. The solid compounds and solid fertilizing material can also be admixed in mixing or blending equipment, or they can be incorporated with fertilizers in granular formulations. Any relative proportion of fertilizer can be used which is suitable for the crops and weeds to be treated. The 2-arylpyrimidine will commonly be from about 5% to about 25% of the fertilizing composition. These compositions provide fertilizing materials which promote the rapid growth of desired plants, and at the same time control the growth of undesired plants.

For some applications, one or more other herbicides may be added of the herbicides of the present invention, thereby providing additional advantages and effectiveness. When mixtures of herbicides are employed, the relative proportions which are used will depend upon the relative efficacy of compounds in the mixture with respect to the plants to be treated. Examples of other herbicides which can be combined with those of the present invention include:

Carboxylic Acids and Derivatives 2,3,6-trichlorobenzoic acid and its salts;
2,3,5,6-tetrachlorobenzoic acid and its salts;
2-methoxy-3,5,6-trichlorobenzoic acid and its salts;
2-methoxy-3,6-dichlorobenzoic acid and its salts;
2-methyl-3,6-dichlorobenzoic acid and its salts;
2,3-dichloro-6-methylbenzoic acid and its salts;
2,4-dichlorophenoxyacetic acid and its salts and esters;
2,4,5-trichlorophenoxyacetic acid and its salts and esters;
2-methyl-4-chlorophenoxyacetic acid and its salts and esters;
2-(2,4,5-trichlorophenoxy)propionic acid and its salts and esters;
4-(2,4-dichlorophenoxy)butyric acid and its salts and esters;
4-(2-methyl-4-chlorophenoxy)butyric acid and its salts and esters;
2,3,6-trichlorophenylacetic acid and its salts;
3,6-endoxohexahydrophthalic acid and its salts;
dimethyl 2,3,5,6-tetrachloroterephthalate; trichloroacetic acid and its salts;
2,2-dichloropropionic acid and its salts;
2,3-dichloroisobutyric acid and its salts;
isopropylammonium 2-(4-isopropyl-4-methyl-5-oxo-2-imidazolin-2-yl)nicotinate;
2-[4,5-dihydro-4-methyl-4-(1-methylethyl)-5-oxo-1H-imidazol-2-yl]-3-quinolinecarboxylic acid;
6-(4-isopropyl-4-methyl-5-oxo-2-imidazolin-2-yl)-m-toluic acid, methyl ester and
6-(4-isopropyl-4-methyl-5-oxo-2-imidazolin-2-yl)-p-toluic acid, methyl ester;
N-(phosphomethyl)glycine isopropylammonium salt;
[3,5,6-trichloro-(2-pyridinyl)oxy]acetic acid;
3,7-dichloro-8-quinolinecarboxylic acid;
ammonium DL-homoalanin-4-yl(methyl)phosphinate;

Carbamic Acid Derivatives ethyl N,N-di(n-propyl)thiolcarbamate;
n-propyl N,N-di(n-propyl)thiolcarbamate;
ethyl N-ethyl-N-(n-butyl)thiolcarbamate;
n-propyl N-ethyl-N-(n-butyl)thiolcarbamate;
2-chloroallyl N,N-diethyldithiocarbamate;

isopropyl N-phenylcarbamate;
isopropyl N-(m-chlorophenyl)carbamate;
4-chloro-2-butynyl-N-(m-chlorophenyl)carbamate;
methyl N-(3,4-dichlorophenyl)carbamate;
dinitro-o-(sec-butyl)phenol and its salts;
pentachlorophenol and its salts
S-(4-chlorobenzyl)-N,N-diethyl thiolcarbamate;

Substituted Ureas 3-(m-trifluoromethylphenyl)-1,1-dimethylurea
2-chloro-N-[(4-methoxy-6-methyl-1,3,5-triazin-2-yl)aminocarbonyl]-benzenesulfonamide;
3-(3,4-dichlorophenyl)-1,1-dimethylurea;
3-phenyl-1,1-dimethylurea;
3-(3,4-dichlorophenyl)-3-methoxy-1,1-dimethylurea;
3-(4-chlorophenyl)-3-methoxy-1,1-dimethylurea;
3-(3,4-dichlorophenyl)-1-n-butyl-1-methylurea;
3-(3,4-dichlorophenyl)-1-methoxy-1-methylurea;
3-(4-chlorophenyl)-1-methoxy-1-methylurea;
3-(3,4-dichlorophenyl)-1,1,3-trimethylurea;
3-(3,4-dichlorophenyl)diethylurea;
N-(4-isopropylphenyl)-N,N-dimethylurea;
dichloral urea;
methyl 2-[[[[(4,6-dimethyl-2-pyrimidinyl)amino]-carbonyl]amino]sulfonyl]benzoate;
N-((6-methoxy-4-methyl-1,3,5-triazin-2-yl)aminocarbonyl)-2-(2-chloroethoxy)-benzenesulfonamide;
2-[[[(4-chloro-6-methoxypyrimidine-2-yl)aminocarbonyl]amino]-sulfonyl]benzoic acid, ethyl ester;
methyl 2-[[[[(4-methoxy-6-methyl-1,3,5-triazin-2-yl)amino]-carbonyl]amino]sulfonyl] benzoate;
methyl 3-[[(4-methoxy-6-methyl-1,3,5-triazin-2-yl)aminocarbonyl]aminosulfonyl] -2-thio-phenecarboxylate;
methyl 2-[[[[(4,6-dimethoxypyrimidin-2-yl)amino]carbonyl]amino]sulfonyl] -methyl]benzoate;
methyl 2-[[[[(4-methoxy-6-methyl-1,3,5-triazin-2-yl)methylamino]carbonyl]amino] -sulfonyl]benzoate;

Substituted Triazines 2-chloro-4,6-bis(ethylamino)-s-triazine;
2-chloro-4-ethylamino-6-isopropylamino-s-triazine;
2-chloro-4,6-bis(3-methoxy-n-propylamino)-s-triazine;
2-methoxy-4,6-bis(isopropylamino)-s-triazine;
2-chloro-4-ethylamino-6-(3-methoxy-n-propylamino)-s-triazine;
2-methylmercapto-4,6-bis(isopropylamino)-s-triazine;
2-methylmercapto-4,6-bis(ethylamino)-2-triazine;
2-methylmercapto-4-ethylamino-6-isopropylamino-s-triazine;
2-chloro-4,6-bis(isopropylamino)-s-triazine;
2-methoxy-4-ethylamino-6-isopropylamino-s-triazine;
2-methylmercapto-4-(2-methoxyethylamino)-6-isopropylamino-s-triazine;
4-amino-6-(t-butyl)-3-(methylthio)-1,2,4-triazine-5(4H)-one;

Diphenyl Ether Derivatives 2,4-dichloro-4'-nitrodiphenyl ether;
2,4,6-trichloro-4'-nitrodiphenyl ether;
2,4-dichloro-6-fluoro-4'-nitrodiphenyl ether;
3-methyl-4'-nitrodiphenyl ether;
3,5-dimethyl-5'-nitrodiphenyl ether;
2,4'-dinitro-4-(trifluoromethyl)diphenyl ether;
2,4-dichloro-3'-methoxy-4'-nitrodiphenyl ether;
sodium 5-(2-chloro-4-(trifluoromethyl)phenoxy)-2-nitrobenzoate;
2-chloro-1-(3-ethoxy-4-nitrophenoxy)-4-(trifluoromethyl)benzene;
1-(carboethoxy)ethyl 5-[2-chloro-4-(trifluoromethyl)-phenoxy]-2-nitrobenzoate;
5-[2-chloro-4-(trifluoromethyl)phenoxyl]-N-(methylsulphony)-2-nitrobenzamide;

Anilides 2-chloro-N-(2-ethyl-6-methylphenyl)-N-(2-methoxy-1-methylethyl)acetamide;
2-chloro-2',6'-diethyl-N-(2-propyloxyethyl)acetanilide;
N-(3,4-dichlorophenyl)propionamide;
N-(3,4-dichlorophenyl)methacrylamide;
N-(3-chloro-4-methylphenyl)-2-methylpentanamide;
N-(3,4-dichlorophenyl)trimethylacetamide;
N-(3,4-dichlorophenyl)-alpha,alpha-dimethylvaleramide;
N-isopropyl-N-phenylchloroacetamide;
N-n-butoxymethyl-N-(2,6-diethylphenyl)chloroacetamide;
N-methoxymethyl-N-(2,6-diethylphenyl)chloroacetamide;

Oxyphenoxy Herbicides 2-(4-(2,4-dichlorophenoxy)phenoxy)methyl propionate;
methyl 2-(4-(3-chloro-5-(trifluoromethyl)-2-pyridinyloxy)phenoxy)propanoate;
butyl (R)-2-[4-[5-(trifluoromethyl)-2-pyridinyloxy]-phenoxy]propionate;
ethyl 2-[4-[(6-chloro-2-benzoxazolyl)oxy]phenoxy]propanoate;
butyl 2-[4-[[5-(trifluoromethyl)-2-pyridinyl]oxy]phenoxy] propionate;
2-[4-[(6-chloro-2-quinoxalinyl)oxy]phenoxy]propionic acid, ethyl ester;

Uracils 5-bromo-3-s-butyl-6-methyluracil;
5-bromo-3-cyclohexyl-1,6-dimethyluracil;
3-cyclohexyl-5,6-trimethylencuracil;
5-bromo-3-isopropyl-6-methyluracil;
3-tert-butyl-5-chloro-6-methyluracil;

Nitriles 2,6-dichlorobenzonitrile;
diphenylacetonitrile;
3,5-dibromo-4-hydroxybenzonitrile;
3,5-diiodo-4-hydroxybenzonitrile;

Other Organic Herbicides 2-chloro-N,N-diallylacetamide;
N-(1,1-dimethyl-2-propynyl)-3,5-dichlorobenzamide;
maleic hydrazide;
3-amino-1,2,4-triazole; monosodium methanearsonate;
disodium methanearsonate;
N,N-dimethyl-alpha,alpha-diphenylacetamide;
N-N-di(n-propyl)-2,6-dinitro-4-(trifluoromethyl)aniline;
N,N-di(n-propyl)-2,6-dinitro-4-methylaniline;
N,N-di(n-propyl)-2,6-dinitro-4-methylsulfonylaniline;
O-(2,4-dichlorophenyl)—O—methyl isopropylphosphoramidothioate;
4-amino-3,5,6-trichloropicolinic acid;
2,3-dichloro-1,4-naphthoquinone;
di(methoxythiocarbonyl)disulfide;
3-(1-methylethyl)-1H-2,1,3-benzothiadiazin-(4)3H-one-2,2-dioxide;

6,7-dihydrodipyridol[1,2-a:2',1'-c]pyrazidiium salts;
1,1'-dimethyl-4,4'-bipyridinium salts;
3,4,5,6-tetrahydro-3,5-dimethyl-2-thio-2H- 1,3,5-thiadiazine;
2-[1-(ethoxyimino)butyl]-5-[s-(ethylthio)propyl]-3-hydroxy-2-cyclohexen-1-one;
2-(2-chlorophenyl)methyl-4,4-dimethyl-3-isoxazolidinone;
N-(1-ethylpropyl)-3,4-dimethyl-2,6-dinitrobenzamide;
4-chloro-5-(methylamino)-2-(a,a,a-trifluoro-m-toluyl)-3-(2H)-pyridazinone;
2-(3,5-dichlorophenyl)-2-(2,2,2-trichloromethyl)oxirane.

When mixtures of herbicides are employed, the relative proportions which are used will depend upon the crop to be treated and the degree of selectivity in weed control desired. The herbicidal activity of the 2-arylpyrimidines of the present invention towards a number of common weeds was evaluated using a greenhouse or a field method of testing. Using the procedures described below, the aryl pyrimidines of the present invention were evaluated for safety to crops and control of weeds selected from the following:

| | Crops |
|---|---|
| Winter Barley (BAR) | *Hordeum sativum* |
| Winter Wheat (WHE) | *Triticum aestivium* |
| Rice (RI) | *Oryza sativa* |
| | Monocots |
| Annual Bluegrass (POA) | *Poa Annua* |
| Barnyardgrass (BYG) | *Echinochloa crus-galli* |
| Crabgrass (CRB) | *Digitaria sanguinalis* |
| Foxtail (FOX) | *Setaria viridis* |
| Johnsongrass (JON) | *Sorghum halegense* |
| Meadow Foxtail (MF) | *Alopecurus pratensis* |
| Nutsedge (NUT) | *Cyperus esculentus* |
| Ryegrass (RYE) | *Lolium perenne* |
| Wild Oat (WO) | *Avena fatua* |
| Signalgrass (SIG) | *Brachiaria platyphylla* |
| Sprangletop (SPR) | *Leptochloa dubia* |
| Spring Oat (OAT) | *Avena sativa* |
| | Dicots |
| Beggartick (BID) | *Bidens pilosa* |
| Chickweed (CW) | *Stellaria media* |
| Cocklebur (CKL) | *Xanthium strumarium* |
| Hemp Sesbania (CFW) | *Sesbania exaltata* |
| Morningglory (MG) | *Ipomoea lacunosa* |
| Nightshade (NS) | *Solanum nigrum* |
| Pigweed (PIG) | *Amaranthus retroflexus* |
| Pineappleweed (MAT) | *Matricaria matricariodies* |
| Smartweed (SMT) | *Polygonum lapathifolium* |
| Velvetleaf (VEL) | *Abutilon theophrasti* |
| Yellow Rocket (YR) | *Barbarea vulgaris* |

Greenhouse Test Method

The following test procedure was employed. Seeds of selected plants were planted in flats or pots. For preemergence tests, immediately after planting, the test compound was sprayed directly onto the soil surface. The flats or pots were placed in the greenhouse and then watered. For postemergence tests, the seeds were allowed to germinate and grow for 10 to 21 days. Before application, each series of test plants were selected for uniformity, size and stage of development. The test plants were then treated with the test compound, returned to the greenhouse and watered.

The compound to be evaluated was dissolved in an appropriate solvent, usually acetone, and sprayed over the flats or pots using a carrier volume equivalent to 25 or 50 gallons per acre at the rate of application in pounds per acre (Lb/A) or grams per hectare (g/Ha) specified in the below tables. About two or three weeks after application of the test compound, the state of growth of the plant was observed. Each species was evaluated on a scale of 0–100 in which 0 equals no activity and 100 equals total control.

Field Test Method

Field applications were made by applying treatments on individual plots usually measuring eight feet in width and twenty feet in length. Each treatment was replicated three times. The test species were either planted into the plots or were found to be indigenous in the test area. Applications were made by moving spray nozzles across the plots at a constant speed and a constant height above the spray target, such that the plots were sprayed uniformly. The rate of application of individual treatments was determined by varying the concentration of the spray solution. The spray solution was prepared by mixing a measured amount of the formulated test material into water, which was the spray carrier. The test material was formulated in an agronomically acceptable formulation. The formulated material when mixed with the water formed a sprayable suspension. The plots were evaluated using a rating system similar to that used in the greenhouse evaluations.

The column heading abbreviations in the below tables for the plants tested are the same as for the monocots and dicots hereinabove. The dash ("-") entry signifies no testing for the specified conditions. The following tables show the results obtained for the test compounds at the stated rate of application are provided merely as illustrations and are not to be considered as limitations or restrictions of the scope of this invention which is defined by the claims.

TABLE 3

| COMPOUND | TYPE | LB/A | GREENHOUSE DATA | | | | | | | | | |
|---|---|---|---|---|---|---|---|---|---|---|---|---|
| | | | CKL | MG | PIG | SMT | VEL | BYG | FOX | JON | NUT | WO |
| 1 | PRE | 4.00 | 20 | 100 | 100 | 100 | 100 | 100 | 100 | 99 | 55 | 100 |
| | POST | 4.00 | 25 | 70 | 100 | 100 | 55 | 80 | 50 | 0 | 15 | 100 |
| 2 | PRE | 4.00 | 5 | 100 | 100 | 100 | 100 | 100 | 100 | 100 | 65 | 60 |
| | POST | 4.00 | 15 | 75 | 75 | 50 | 35 | 80 | 75 | 0 | 0 | 35 |
| 4 | PRE | 4.00 | 25 | 100 | 100 | 100 | 100 | 100 | 100 | 100 | 85 | 100 |
| | POST | 4.00 | 20 | 45 | 100 | 55 | 50 | 95 | 95 | 70 | 35 | 90 |
| 5 | PRE | 4.00 | 40 | 100 | 100 | 100 | 100 | 100 | 100 | 100 | 100 | 98 |
| | POST | 4.00 | 20 | 85 | 70 | 99 | 65 | 98 | 95 | 65 | 80 | 70 |
| 6 | PRE | 4.00 | 15 | 100 | 100 | 100 | 100 | 100 | 100 | 100 | 100 | 85 |
| | POST | 4.00 | 0 | 10 | 45 | 40 | 0 | 20 | 0 | 70 | 15 | 0 |
| 7 | PRE | 4.00 | 0 | 10 | — | 100 | 60 | 90 | 100 | 55 | — | 40 |
| | POST | 4.00 | 0 | 0 | 20 | 15 | 20 | 0 | 0 | 0 | 0 | 0 |

"—" EQUALS NOT TESTED

TABLE 3A

| COMPOUND | TYPE | LB/A | BID | NS | SMT | VEL | BYG | CRB | FOX | MF |
|---|---|---|---|---|---|---|---|---|---|---|
| 8 | PRE | 4.00 | 100 | 100 | 100 | 100 | 100 | 100 | 100 | — |
|   | POST | 4.00 | 15 | 100 | 5 | 5 | 20 | 20 | 75 | 65 |
| 9 | PRE | 2.00 | — | 80 | 100 | 10 | 100 | — | 100 | — |
|   | POST | 2.00 | — | 30 | 0 | 0 | 0 | — | 0 | — |
| 11 | PRE | 2.00 | — | 100 | 100 | 100 | 100 | — | 100 | — |
|   | POST | 2.00 | — | 45 | 0 | 0 | 15 | — | 15 | — |
| 12 | PRE | 1.00 | 25 | 100 | 100 | 100 | 100 | 100 | 100 | 100 |
|   | POST | 1.00 | 25 | 100 | 100 | 35 | 95 | 95 | 95 | 95 |
| 13 | PRE | 1.00 | 0 | 100 | 95 | 0 | 90 | 100 | 100 | 90 |
|   | POST | 1.00 | 0 | 20 | 20 | 20 | 0 | 20 | 0 | 0 |
| 14 | PRE | 1.00 | 60 | 100 | 100 | 95 | 100 | 100 | 100 | 100 |
|   | POST | 1.00 | 75 | 95 | 95 | 80 | 100 | 95 | 80 | 50 |
| 15 | PRE | 1.00 | 25 | 40 | 100 | 90 | 0 | 80 | 0 | 0 |
|   | POST | 1.00 | 0 | 60 | 0 | 0 | 0 | 0 | 0 | 0 |
| 16 | PRE | 1.00 | 80 | 100 | 100 | 90 | 100 | 100 | 100 | 100 |
|   | POST | 1.00 | 35 | 100 | 95 | 10 | 90 | 95 | 85 | 90 |
| 17 | PRE | 1.00 | 0 | 90 | 100 | 80 | 40 | 90 | 25 | 0 |
|   | POST | 1.00 | 20 | 100 | 20 | 0 | 0 | 20 | 0 | 0 |
| 18 | PRE | 1.00 | 0 | 0 | 0 | 0 | 0 | 40 | 0 | 0 |
|   | POST | 1.00 | 0 | 100 | 0 | 0 | 0 | 0 | 0 | 0 |
| 19 | PRE | 1.00 | 0 | 25 | 25 | 0 | 0 | 0 | 0 | 0 |
|   | POST | 1.00 | 10 | 100 | 0 | 20 | 0 | 0 | 0 | 0 |
| 20 | PRE | 1.00 | 50 | 75 | 20 | 40 | 75 | 90 | 100 | 75 |
|   | POST | 1.00 | 0 | 0 | 0 | 0 | 0 | 0 | 0 | 0 |
| 21 | PRE | 1.00 | 0 | 10 | 90 | 0 | 90 | 100 | 50 | 90 |
|   | POST | 1.00 | 0 | — | 0 | 0 | 0 | 0 | 0 | 0 |
| 22 | PRE | 1.00 | 90 | 100 | 100 | 100 | 100 | 100 | 100 | 100 |
|   | POST | 1.00 | 70 | — | 100 | 0 | 100 | 100 | 80 | 100 |
| 23 | PRE | 1.00 | 25 | 95 | 0 | 100 | 25 | 0 | 95 | 100 |
|   | POST | 1.00 | 10 | — | 10 | 0 | 0 | 20 | 0 | 0 |
| 25 | PRE | 1.00 | 0 | — | 0 | 0 | 0 | 0 | 0 | 0 |
|   | POST | 1.00 | 25 | 50 | 25 | 0 | 0 | 0 | 0 | 0 |
| 26 | PRE | 1.00 | 0 | — | 0 | 0 | 50 | 75 | 40 | 0 |
|   | POST | 1.00 | 0 | 0 | 0 | 0 | 0 | 0 | 0 | 0 |
| 27 | PRE | 1.00 | 0 | — | — | 20 | 95 | 100 | 100 | 100 |
|   | POST | 1.00 | 0 | 85 | 60 | 0 | 75 | 75 | 10 | 75 |
| 28 | PRE | 1.00 | 0 | — | — | 20 | 100 | 100 | 100 | 100 |
|   | POST | 1.00 | 20 | 95 | 50 | 60 | 95 | 95 | 50 | 90 |
| 29 | PRE | 1.00 | 25 | — | — | 60 | 100 | 100 | 100 | 100 |
|   | POST | 1.00 | 25 | 100 | 100 | 50 | 95 | 95 | 90 | 100 |
| 30 | PRE | 1.00 | 0 | 0 | 25 | 0 | 60 | 100 | 90 | 80 |
|   | POST | 1.00 | 0 | 75 | 0 | 0 | 0 | 0 | 0 | 0 |
| 31 | PRE | 1.00 | 10 | 100 | 100 | 20 | 100 | 100 | 100 | 100 |
|   | POST | 1.00 | 25 | 90 | 95 | 20 | 95 | 100 | 70 | 95 |
| 32 | PRE | 1.00 | 0 | 95 | 100 | 25 | 95 | 100 | 100 | 95 |
|   | POST | 1.00 | 25 | 90 | 90 | 20 | 95 | 95 | 80 | 90 |
| 33 | PRE | 1.00 | 20 | 100 | 100 | 0 | 95 | 100 | 100 | 100 |
|   | POST | 1.00 | 20 | 80 | 40 | 0 | 25 | 25 | 25 | 50 |
| 35 | PRE | 1.00 | 20 | 0 | 100 | 40 | 100 | 100 | 100 | 100 |
|   | POST | 1.00 | 10 | 95 | 95 | 10 | 95 | 95 | 70 | 60 |
| 36 | PRE | 1.00 | 0 | 100 | 60 | 0 | 75 | 95 | 75 | 75 |
|   | POST | 1.00 | 40 | 80 | 40 | 0 | 50 | 40 | 40 | 10 |
| 37 | PRE | 1.00 | 10 | 95 | 95 | 10 | 90 | 95 | 90 | 90 |
|   | POST | 1.00 | 30 | 25 | 40 | 0 | 20 | 0 | 0 | 0 |
| 38 | PRE | 1.00 | 0 | 25 | 0 | 80 | 0 | 0 | 0 | 0 |
|   | POST | 1.00 | 20 | 20 | 0 | 0 | 0 | 0 | 0 | 0 |
| 39 | PRE | 1.00 | 80 | 95 | — | 80 | 95 | 100 | 100 | 100 |
|   | POST | 1.00 | 70 | 95 | 90 | 25 | 90 | 95 | 60 | 95 |
| 40 | PRE | 1.00 | 0 | 90 | — | 0 | 50 | 75 | 80 | 0 |
|   | POST | 1.00 | 40 | 0 | 0 | 0 | 25 | 0 | 0 | 0 |
| 41 | PRE | 1.00 | 40 | 25 | 100 | 95 | 0 | 60 | 40 | 0 |
|   | POST | 1.00 | 0 | 0 | 0 | 0 | 0 | 0 | 0 | 0 |
| 45 | PRE | 1.00 | 0 | 95 | 100 | 0 | 85 | 95 | 100 | 95 |
|   | POST | 1.00 | 70 | 90 | 90 | 60 | 85 | 80 | 20 | 85 |
| 46 | PRE | 1.00 | 80 | 100 | 100 | 100 | 100 | 100 | 100 | 100 |
|   | POST | 1.00 | 95 | 100 | 100 | 85 | 95 | 100 | 95 | 95 |
| 47 | PRE | 1.00 | 0 | 90 | 90 | 20 | 95 | 95 | 95 | 95 |
|   | POST | 1.00 | 0 | 100 | 0 | 0 | 25 | 25 | 0 | 0 |
| 48 | PRE | 1.00 | 95 | 100 | 100 | 80 | 100 | 100 | 100 | 100 |
|   | POST | 1.00 | 70 | 100 | 100 | 70 | 100 | 95 | 90 | 95 |
| 51 | PRE | 1.00 | 80 | 95 | 20 | 50 | 100 | 95 | 100 | 100 |
|   | POST | 1.00 | 20 | 90 | 25 | 0 | 40 | 50 | 20 | 0 |
| 52 | PRE | 2.00 | — | 95 | 100 | 0 | 35 | — | 100 | — |
|   | POST | 2.00 | — | 0 | 0 | 0 | 0 | — | 0 | — |
| 53 | PRE | 1.00 | 0 | 90 | — | 25 | 90 | 95 | 95 | 40 |
|   | POST | 1.00 | 0 | 90 | 80 | 10 | 50 | 40 | 25 | 10 |
| 54 | PRE | 1.00 | 100 | 100 | 95 | 100 | 100 | 100 | 100 | 100 |

TABLE 3A-continued

| COMPOUND | TYPE | LB/A | BID | NS | SMT | VEL | BYG | CRB | FOX | MF |
|---|---|---|---|---|---|---|---|---|---|---|
|  | POST | 1.00 | 95 | 100 | 100 | 90 | 95 | 95 | 95 | 95 |
| 55 | PRE | 1.00 | 25 | 95 | 95 | 50 | 100 | 100 | 100 | 100 |
|  | POST | 1.00 | 20 | 90 | 90 | 75 | 80 | 90 | 80 | 80 |
| 56 | PRE | 1.00 | 95 | 100 | 95 | 40 | 100 | 100 | 100 | 100 |
|  | POST | 1.00 | 70 | 100 | 90 | 50 | 95 | 95 | 95 | 95 |
| 57 | PRE | 1.00 | 25 | 100 | 85 | 25 | 100 | 100 | 100 | 100 |
|  | POST | 1.00 | 25 | 100 | 90 | 50 | 90 | 95 | 80 | 90 |
| 58 | PRE | 1.00 | 95 | 100 | 95 | 100 | 100 | 100 | 100 | 100 |
|  | POST | 1.00 | 80 | 80 | 90 | 85 | 80 | 100 | 75 | 70 |
| 59 | PRE | 1.00 | 20 | 100 | 95 | 80 | 100 | 100 | 100 | 100 |
|  | POST | 1.00 | 20 | 70 | 40 | 20 | 80 | 90 | 40 | 70 |
| 60 | PRE | 1.00 | 40 | 100 | 85 | 40 | 95 | 100 | 100 | 100 |
|  | POST | 1.00 | 25 | 95 | 85 | 25 | 70 | 95 | 60 | 40 |
| 61 | PRE | 1.00 | 0 | 70 | 0 | 0 | 0 | 0 | 0 | 0 |
|  | POST | 1.00 | 0 | 80 | 20 | 0 | 20 | 0 | 20 | 0 |
| 62 | PRE | 1.00 | 90 | 100 | 90 | 100 | 100 | 100 | 100 | 100 |
|  | POST | 1.00 | 80 | 100 | 100 | 90 | 90 | 95 | 95 | 100 |
| 63 | PRE | 1.00 | 0 | 90 | 10 | 0 | 0 | 10 | 20 | 0 |
|  | POST | 1.00 | 10 | 10 | 0 | 0 | 0 | 20 | 0 | 0 |
| 64 | PRE | 1.00 | 20 | 100 | 95 | 50 | 100 | 100 | 100 | 100 |
|  | POST | 1.00 | 60 | 100 | 100 | 75 | 95 | 95 | 95 | 95 |
| 65 | PRE | 1.00 | 10 | 100 | 100 | 20 | 100 | 100 | 100 | 100 |
|  | POST | 1.00 | 40 | 100 | 75 | 50 | 95 | 95 | 95 | 90 |
| 66 | PRE | 1.00 | 10 | 95 | 100 | 100 | 100 | 100 | 100 | 100 |
|  | POST | 1.00 | 70 | 100 | 100 | 80 | 95 | 100 | 90 | 95 |
| 67 | PRE | 1.00 | 0 | 95 | 80 | 10 | 95 | 100 | 100 | 100 |
|  | POST | 1.00 | 10 | 100 | 80 | 20 | 90 | 95 | 90 | 90 |
| 68 | PRE | 1.00 | 50 | 100 | 100 | 40 | 100 | 100 | 100 | 100 |
|  | POST | 1.00 | 70 | 100 | 85 | 70 | 95 | 95 | 85 | 85 |
| 69 | PRE | 1.00 | — | — | 100 | 0 | 0 | 0 | 0 | 0 |
|  | POST | 1.00 | 0 | 50 | 10 | 0 | 0 | 0 | 0 | 0 |
| 70 | PRE | 1.00 | 0 | 100 | 100 | 50 | 100 | 100 | 100 | 100 |
|  | POST | 1.00 | 25 | 80 | 85 | 60 | 70 | 90 | 60 | 50 |
| 71 | PRE | 1.00 | 20 | 100 | 100 | 0 | 100 | 100 | 100 | 100 |
|  | POST | 1.00 | 40 | 95 | 70 | 60 | 80 | 95 | 60 | 70 |
| 76 | PRE | 1.00 | 0 | 100 | 90 | 85 | 95 | 100 | 100 | 100 |
|  | POST | 1.00 | 25 | 100 | 95 | 25 | 85 | 75 | 70 | 75 |
| 77 | PRE | 1.00 | 20 | 100 | 90 | 100 | 100 | 100 | 100 | 100 |
|  | POST | 1.00 | 90 | 100 | 100 | 85 | 95 | 90 | 90 | 90 |
| 79 | PRE | 1.00 | 0 | 0 | 0 | 0 | 0 | 0 | 0 | 0 |
|  | POST | 1.00 | 0 | 50 | 0 | 0 | 0 | 0 | 0 | 0 |
| 80 | PRE | 1.00 | 0 | 90 | 20 | 0 | 60 | 95 | 95 | 70 |
|  | POST | 1.00 | 10 | 95 | 20 | 40 | 0 | 0 | 20 | 0 |
| 81 | PRE | 1.00 | 0 | 0 | 0 | 0 | 0 | 90 | 0 | 0 |
|  | POST | 1.00 | 20 | 20 | 0 | 0 | 0 | 0 | 0 | 0 |
| 83 | PRE | 1.00 | 0 | 90 | 90 | 0 | 70 | 95 | 40 | 30 |
|  | POST | 1.00 | 30 | 50 | 20 | 10 | 0 | 0 | 0 | 0 |
| 84 | PRE | 1.00 | 75 | 95 | 60 | 80 | 90 | 100 | 100 | 100 |
|  | POST | 1.00 | 50 | 100 | 90 | 50 | 85 | 90 | 75 | 75 |
| 85 | PRE | 1.00 | 60 | 80 | 95 | 70 | 100 | 100 | 100 | 100 |
|  | POST | 1.00 | 90 | 100 | 95 | 75 | 95 | 100 | 90 | 90 |
| 87 | PRE | 1.00 | 0 | 0 | 0 | 0 | 80 | 90 | 100 | 90 |
|  | POST | 1.00 | 0 | 20 | 0 | 0 | 25 | 95 | 0 | 0 |
| 88 | PRE | 1.00 | 0 | 90 | 85 | 60 | 95 | 100 | 100 | 95 |
|  | POST | 1.00 | 40 | 100 | 70 | 80 | 85 | 95 | 75 | 80 |
| 89 | PRE | 1.00 | 0 | 0 | 0 | 0 | 0 | 100 | 0 | 0 |
|  | POST | 1.00 | 0 | 70 | 0 | 0 | 0 | 0 | 0 | 0 |
| 90 | PRE | 1.00 | 80 | 100 | 100 | 20 | 100 | 100 | 100 | 100 |
|  | POST | 1.00 | 80 | 100 | 90 | 35 | 95 | 95 | 90 | 90 |
| 91 | PRE | 1.00 | 0 | 0 | 0 | 0 | 10 | 80 | 10 | 0 |
|  | POST | 1.00 | 0 | 0 | 0 | 0 | 0 | 0 | 0 | 0 |
| 92 | PRE | 1.00 | 0 | 0 | 0 | 0 | 0 | 100 | 0 | 0 |
|  | POST | 1.00 | 0 | 0 | 0 | 0 | 0 | 0 | 0 | 0 |
| 94 | PRE | 1.00 | 0 | 100 | 100 | 70 | 100 | — | 100 | 100 |
|  | POST | 1.00 | 70 | 100 | 90 | 60 | 90 | 90 | 85 | 80 |
| 95 | PRE | 1.00 | 60 | 90 | 95 | 70 | 100 | — | 85 | 100 |
|  | POST | 1.00 | 70 | 100 | 85 | 80 | 95 | 90 | 85 | 90 |
| 96 | PRE | 1.00 | 20 | 100 | — | 40 | 90 | 95 | 90 | 95 |
|  | POST | 1.00 | 60 | 100 | 90 | 75 | 95 | 95 | 50 | 90 |
| 97 | PRE | 1.00 | 60 | 100 | — | 25 | 100 | 100 | 100 | 100 |
|  | POST | 1.00 | 85 | 100 | — | 100 | 100 | 100 | 100 | 100 |
| 98 | PRE | 1.00 | 80 | 100 | — | 100 | 100 | 100 | 100 | 100 |
|  | POST | 1.00 | 90 | 100 | 90 | 85 | 95 | 95 | 90 | 90 |
| 99 | PRE | 1.00 | 0 | 100 | 80 | 10 | 100 | 95 | 100 | 100 |
|  | POST | 1.00 | 0 | 100 | 90 | 0 | 80 | 95 | 20 | 90 |
| 103 | PRE | 1.00 | 10 | 95 | 95 | 75 | 100 | 100 | 100 | 100 |
|  | POST | 1.00 | 40 | 95 | 100 | 25 | 100 | 95 | 85 | 95 |

TABLE 3A-continued

| COMPOUND | TYPE | LB/A | BID | NS | SMT | VEL | BYG | CRB | FOX | MF |
|---|---|---|---|---|---|---|---|---|---|---|
| 105 | PRE | 1.00 | 0 | 0 | 0 | 0 | 0 | 0 | 0 | 0 |
|  | POST | 1.00 | 0 | 25 | 0 | 0 | 0 | 25 | 0 | 0 |
| 106 | PRE | 1.00 | 25 | 90 | 50 | 100 | 100 | — | 100 | 100 |
|  | POST | 1.00 | 50 | 80 | 70 | 60 | 85 | 90 | 70 | 60 |
| 107 | PRE | 1.00 | 95 | 95 | 70 | 50 | 90 | — | 95 | 95 |
|  | POST | 1.00 | 40 | 80 | 85 | 75 | 90 | 85 | 35 | 60 |
| 108 | PRE | 1.00 | 95 | 100 | 95 | 70 | 100 | 100 | 100 | 100 |
|  | POST | 1.00 | 85 | 85 | 80 | 40 | 65 | 90 | 50 | 50 |
| 110 | PRE | 1.00 | 100 | 100 | 100 | 100 | 100 | 100 | 100 | 100 |
|  | POST | 1.00 | 75 | 100 | 85 | 70 | 90 | 95 | 85 | 80 |
| 111 | PRE | 1.00 | 100 | 40 | 20 | 0 | 20 | 100 | 50 | 0 |
|  | POST | 1.00 | 0 | 60 | 0 | 0 | 10 | 0 | 0 | 0 |
| 112 | PRE | 1.00 | 0 | 100 | 0 | 0 | 80 | — | 95 | — |
|  | POST | 1.00 | 0 | 75 | 60 | 35 | 25 | 75 | 15 | 10 |
| 113 | PRE | 1.00 | 40 | 100 | 40 | 0 | 20 | 0 | 0 | 0 |
|  | POST | 1.00 | 0 | 80 | 50 | 20 | 35 | 20 | 0 | 10 |
| 114 | PRE | 1.00 | 0 | 80 | 20 | 0 | 50 | 95 | 60 | 50 |
|  | POST | 1.00 | 0 | 80 | 40 | 20 | 40 | 30 | 0 | 0 |
| 115 | PRE | 1.00 | 100 | 100 | 25 | 0 | 40 | 100 | 60 | 90 |
|  | POST | 1.00 | 0 | 80 | 60 | 20 | 0 | 50 | 0 | 0 |
| 116 | PRE | 1.00 | 50 | 100 | 100 | 60 | 100 | 100 | 100 | 100 |
|  | POST | 1.00 | 25 | 95 | 100 | 85 | 90 | 95 | 80 | 95 |
| 117 | PRE | 1.00 | 80 | 100 | 40 | 35 | 95 | 95 | 100 | 95 |
|  | POST | 1.00 | 20 | 90 | 25 | 35 | 50 | 60 | 30 | 25 |
| 118 | PRE | 1.00 | 50 | 95 | 80 | 0 | 95 | 100 | 95 | 95 |
|  | POST | 1.00 | 60 | 90 | 95 | 40 | 90 | 95 | 85 | 90 |
| 119 | PRE | 1.00 | 85 | 95 | 80 | 0 | 90 | 100 | 100 | 95 |
|  | POST | 1.00 | 80 | 90 | 95 | 70 | 90 | 95 | 70 | 75 |
| 120 | PRE | 1.00 | 0 | 0 | 0 | 0 | 25 | 20 | 20 | 0 |
|  | POST | 1.00 | 25 | 80 | 60 | 50 | 40 | 40 | 25 | 10 |
| 121 | PRE | 1.00 | 90 | 95 | 40 | 25 | 85 | 95 | 100 | 80 |
|  | POST | 1.00 | 25 | 100 | 100 | 75 | 90 | 90 | 80 | 85 |
| 122 | PRE | 1.00 | 80 | 95 | 70 | 60 | 100 | 100 | 100 | 100 |
|  | POST | 1.00 | 50 | 90 | 80 | 60 | 85 | 85 | 80 | 60 |
| 123 | PRE | 1.00 | 100 | 100 | 95 | 40 | 100 | 100 | 100 | 100 |
|  | POST | 1.00 | 75 | 100 | 100 | 35 | 95 | 90 | 85 | 85 |
| 124 | PRE | 4.00 | 95 | 75 | 0 | 0 | 10 | 90 | 10 | 20 |
|  | POST | 4.00 | 25 | 100 | 80 | 50 | 80 | 80 | 25 | 40 |
| 125 | PRE | 1.00 | 95 | 100 | 95 | 40 | 100 | 100 | 100 | 100 |
|  | POST | 1.00 | 85 | 100 | 100 | 80 | 95 | 95 | 90 | 90 |
| 126 | PRE | 1.00 | 95 | 95 | 50 | 0 | 100 | 100 | 100 | 100 |
|  | POST | 1.00 | 30 | 90 | 80 | 70 | 95 | 95 | 95 | 95 |
| 127 | PRE | 1.00 | 0 | 0 | 0 | 0 | 0 | 0 | 0 | 0 |
|  | POST | 1.00 | 0 | 25 | 10 | 0 | 0 | 10 | 0 | 0 |
| 128 | PRE | 1.00 | 0 | 85 | 20 | 0 | 60 | 85 | 95 | 85 |
|  | POST | 1.00 | 80 | 80 | 60 | 40 | 10 | 70 | 25 | 10 |
| 129 | PRE | 1.00 | 100 | 100 | 60 | 0 | 100 | 95 | 100 | 100 |
|  | POST | 1.00 | 40 | 95 | 85 | 75 | 95 | 90 | 85 | 85 |
| 130 | PRE | 1.00 | 95 | 100 | 100 | 60 | 100 | 100 | 100 | 100 |
|  | POST | 1.00 | 35 | 100 | 100 | 95 | 95 | 95 | 90 | 95 |
| 131 | PRE | 1.00 | 0 | 20 | 0 | 0 | 80 | 95 | 60 | 50 |
|  | POST | 1.00 | 0 | 80 | 25 | 25 | 20 | 70 | 0 | 0 |
| 132 | PRE | 1.00 | 0 | 100 | 95 | 10 | 100 | 100 | 100 | 100 |
|  | POST | 1.00 | 40 | 100 | 100 | 80 | 90 | 95 | 85 | 95 |

"—" MEANS NOT TESTED

TABLE 3B

| | | GREENHOUSE DATA | | | | | | | |
|---|---|---|---|---|---|---|---|---|---|
| COMPOUND | TYPE | g/HA | BID | BYG | CRB | FOX | MF | NS | SMT | VEL |
| 133 | POST | 1200 | 40 | 20 | 70 | 0 | 0 | 80 | 50 | 40 |
|  | PRE | 1200 | 20 | 60 | 100 | 40 | 10 | 100 | 20 | 0 |
| 134 | POST | 1200 | 80 | 85 | 95 | 85 | 80 | 90 | 85 | 80 |
|  | PRE | 1200 | 100 | 100 | 100 | 100 | 100 | 100 | 100 | 100 |
| 135 | POST | 1200 | 25 | 90 | 100 | 70 | 75 | 90 | 75 | 40 |
|  | PRE | 1200 | 95 | 100 | 100 | 100 | 100 | 100 | 100 | 0 |
| 136 | POST | 1200 | 85 | 90 | 100 | 95 | 95 | 95 | 85 | 60 |
|  | PRE | 1200 | 95 | 95 | 95 | 95 | 95 | 100 | 95 | 25 |
| 137 | POST | 1200 | 60 | 0 | 85 | 0 | 0 | 80 | 70 | 10 |
|  | PRE | 1200 | 25 | 90 | 95 | 95 | 95 | 100 | 75 | 0 |

TABLE 3B-continued

| | | | GREENHOUSE DATA | | | | | | | |
|---|---|---|---|---|---|---|---|---|---|---|
| COMPOUND | TYPE | g/HA | BID | BYG | CRB | FOX | MF | NS | SMT | VEL |
| 138 | POST | 1200 | 0 | 0 | 0 | 0 | 0 | 25 | 0 | 0 |
| | PRE | 1200 | 70 | 0 | 0 | 0 | 0 | 25 | 0 | 0 |
| 139 | POST | 1200 | 0 | 0 | 0 | 0 | 0 | 0 | 0 | 0 |
| | PRE | 1200 | 0 | 10 | 75 | 0 | 0 | 85 | 0 | 0 |
| 140 | POST | 1200 | 25 | 90 | 100 | 100 | 95 | 100 | 100 | 80 |
| | PRE | 1200 | 0 | 100 | 100 | 100 | 100 | 100 | 100 | 80 |
| 141 | POST | 1200 | 0 | 0 | 0 | 0 | 0 | 70 | 10 | 0 |
| | PRE | 1200 | 100 | 0 | 100 | 100 | 25 | 100 | 95 | 0 |
| 142 | POST | 1200 | 0 | 0 | 0 | 0 | 0 | 0 | 0 | 0 |
| | PRE | 1200 | 0 | 0 | 60 | 95 | 0 | 0 | 0 | 0 |
| 143 | POST | 1200 | 25 | 85 | 90 | 90 | 90 | 95 | 85 | 75 |
| | PRE | 1200 | 100 | 100 | 100 | 100 | 100 | 100 | 100 | 100 |
| 144 | POST | 1200 | 20 | 85 | 95 | 40 | 80 | 100 | 90 | 10 |
| | PRE | 1200 | 25 | 100 | 100 | 100 | 100 | 100 | 40 | 0 |
| 145 | POST | 1200 | 50 | 100 | 100 | 95 | 95 | 100 | 50 | 40 |
| | PRE | 1200 | 100 | 100 | 100 | 100 | 100 | 100 | 100 | 50 |
| 146 | POST | 1200 | 25 | 95 | 100 | 90 | 95 | 100 | 75 | 20 |
| | PRE | 1200 | 100 | 100 | 100 | 100 | 100 | 100 | 100 | 80 |
| 147 | POST | 1200 | 10 | 100 | 95 | 80 | 95 | 100 | 100 | 40 |
| | PRE | 1200 | 95 | 100 | 100 | 100 | 100 | 100 | 100 | 95 |
| 148 | POST | 1200 | 25 | 90 | 90 | 95 | 95 | 100 | 100 | 80 |
| | PRE | 1200 | 100 | 100 | 100 | 100 | 100 | 100 | 100 | 80 |
| 149 | POST | 1200 | 50 | 95 | 95 | 95 | 95 | 100 | 95 | 70 |
| | PRE | 1200 | 100 | 100 | 100 | 100 | 100 | 100 | 100 | 100 |
| 150 | POST | 1200 | 0 | 0 | 20 | 0 | 0 | 20 | 0 | 0 |
| | PRE | 1200 | 0 | 0 | 95 | 50 | 10 | 20 | 0 | 0 |
| 151 | POST | 1200 | 40 | 20 | 10 | 20 | 10 | 70 | 75 | 0 |
| | PRE | 1200 | 95 | 100 | 100 | 95 | 100 | 100 | 80 | 20 |
| 152 | POST | 1200 | 50 | 80 | 85 | 80 | 85 | 100 | 80 | 25 |
| | PRE | 1200 | 0 | 100 | 100 | 100 | 100 | 100 | 100 | 0 |
| 153 | POST | 1200 | 90 | 90 | 85 | 90 | 100 | 95 | 95 | 80 |
| | PRE | 1200 | 100 | 100 | 100 | 100 | 100 | 100 | 100 | 100 |
| 154 | POST | 1200 | 70 | 85 | 95 | 90 | 85 | 100 | 85 | 80 |
| | PRE | 1200 | 100 | 100 | 100 | 100 | 100 | 100 | 100 | 80 |
| 155 | POST | 1200 | 25 | 70 | 90 | 25 | 80 | 100 | 70 | 40 |
| | PRE | 1200 | 0 | 100 | 100 | 100 | 100 | 100 | 100 | 0 |
| 156 | POST | 1200 | 0 | 0 | 40 | 0 | 0 | 60 | 0 | 0 |
| | PRE | 1200 | 0 | 25 | 95 | 100 | 100 | 95 | 25 | 20 |
| 157 | POST | 1200 | 10 | 50 | 85 | 20 | 50 | 95 | 75 | 70 |
| | PRE | 1200 | 0 | 100 | 100 | 100 | 100 | 100 | 75 | 10 |
| 158 | POST | 1200 | 40 | 40 | 90 | 70 | 60 | 90 | 80 | 20 |
| | PRE | 1200 | 80 | 70 | 100 | 95 | 100 | 100 | 100 | 0 |
| 159 | POST | 1200 | 75 | 85 | 90 | 85 | 85 | 95 | 85 | 70 |
| | PRE | 1200 | 0 | 100 | 100 | 100 | 100 | 100 | 100 | 60 |
| 160 | POST | 1200 | 10 | 40 | 90 | 10 | 25 | 95 | 20 | 10 |
| | PRE | 1200 | 70 | 75 | 100 | 100 | 95 | 100 | 80 | 25 |
| 161 | POST | 1200 | 10 | 90 | 95 | 90 | 95 | 100 | 90 | 30 |
| | PRE | 1200 | 0 | 100 | 95 | 100 | 100 | 100 | 100 | 20 |
| 162 | POST | 1200 | 10 | 10 | 75 | 10 | 0 | 75 | 10 | 10 |
| | PRE | 1200 | 40 | 0 | 100 | 0 | 20 | 40 | 20 | 0 |
| 163 | POST | 1200 | 40 | 90 | 90 | 70 | 95 | 95 | 75 | 35 |
| | PRE | 1200 | 0 | 100 | 100 | 100 | 100 | 100 | 70 | 0 |
| 164 | POST | 1200 | 20 | 95 | 95 | 40 | 90 | 80 | 70 | 20 |
| | PRE | 1200 | 95 | 100 | 100 | 100 | 100 | 100 | 100 | 25 |
| 165 | POST | 1200 | 20 | 10 | 10 | 10 | 10 | 75 | 10 | 10 |
| | PRE | 1200 | 90 | 25 | 95 | 0 | 0 | 100 | 0 | 0 |
| 166 | POST | 1200 | 20 | 95 | 95 | 100 | 100 | 100 | 90 | 60 |
| | PRE | 1200 | 0 | 100 | 100 | 100 | 100 | 100 | 100 | 100 |
| 167 | POST | 1200 | 0 | 10 | 95 | 10 | 10 | 85 | 25 | 0 |
| | PRE | 1200 | 0 | 40 | 95 | 20 | 10 | 95 | 0 | 0 |
| 168 | POST | 1200 | 85 | 80 | 90 | 80 | 90 | 70 | 70 | 40 |
| | PRE | 1200 | 25 | 95 | 95 | 100 | 100 | 100 | 25 | 25 |
| 169 | POST | 1200 | 0 | 0 | 50 | 0 | 0 | 80 | 0 | 0 |
| | PRE | 1200 | 0 | 90 | 95 | 95 | 10 | 100 | 0 | 0 |
| 170 | POST | 1200 | 0 | 20 | 95 | 0 | 25 | 95 | 50 | 10 |
| | PRE | 1200 | 0 | 90 | 100 | 95 | 90 | 95 | 40 | 0 |
| 171 | POST | 1200 | 10 | 40 | 90 | 40 | 60 | 90 | 70 | 0 |
| | PRE | 1200 | 0 | 90 | 95 | 100 | 95 | 95 | 50 | 0 |
| 172 | POST | 1200 | 25 | 80 | 95 | 90 | 90 | 10 | 95 | 10 |
| | PRE | 1200 | 100 | 100 | 95 | 100 | 100 | 100 | 100 | 10 |
| 173 | POST | 1200 | 25 | 25 | 25 | 20 | 20 | 90 | 20 | 20 |
| | PRE | 1200 | 100 | 100 | 95 | 100 | 100 | 100 | 100 | 40 |
| 174 | POST | 1200 | 0 | 0 | 0 | 0 | 0 | 80 | io | 0 |
| | PRE | 1200 | 20 | 70 | 40 | 80 | 70 | 40 | 20 | 10 |
| 175 | POST | 1200 | 0 | 0 | 0 | 0 | 0 | 95 | 10 | 10 |

TABLE 3B-continued

GREENHOUSE DATA

| COMPOUND | TYPE | g/HA | BID | BYG | CRB | FOX | MF | NS | SMT | VEL |
|---|---|---|---|---|---|---|---|---|---|---|
|  | PRE | 1200 | 95 | 95 | 100 | 95 | 100 | 100 | 70 | 20 |
| 176 | POST | 1200 | 90 | 80 | 80 | 70 | 85 | 90 | 90 | 85 |
|  | PRE | 1200 | 0 | 100 | 95 | 100 | 95 | 80 | 80 | 80 |
| 177 | POST | 1200 | 0 | 70 | 75 | 0 | 0 | 95 | 60 | 0 |
|  | PRE | 1200 | 40 | 100 | 100 | — | 100 | 100 | 90 | 10 |
| 178 | POST | 1200 | 0 | 65 | 75 | 20 | 40 | 95 | 60 | 25 |
|  | PRE | 1200 | 20 | 95 | 95 | — | 100 | 100 | 75 | 25 |
| 179 | POST | 1200 | 0 | 20 | 70 | 0 | 20 | 70 | 10 | 0 |
|  | PRE | 1200 | 0 | 70 | 100 | — | 100 | 90 | 60 | 20 |
| 180 | POST | 1200 | 80 | 75 | 60 | 65 | 90 | 90 | 75 | 40 |
|  | PRE | 1200 | 100 | 100 | 100 | — | 100 | 100 | 100 | 75 |
| 181 | POST | 1200 | 0 | 0 | 0 | 0 | 0 | 10 | 0 | 0 |
|  | PRE | 1200 | 100 | 25 | 100 | — | 25 | 70 | 100 | 100 |
| 182 | POST | 1200 | 0 | 80 | 95 | 10 | 0 | 90 | 90 | 10 |
|  | PRE | 1200 | 0 | 100 | 100 | — | 100 | 95 | 95 | 95 |
| 183 | POST | 1200 | 40 | 75 | 85 | 70 | 75 | 95 | 80 | 40 |
|  | PRE | 1200 | 95 | 95 | 100 | 95 | 95 | 95 | 95 | 60 |
| 184 | POST | 1200 | 20 | 90 | 65 | 75 | 25 | 95 | 85 | 75 |
|  | PRE | 1200 | 100 | 95 | 95 | 95 | 95 | 95 | 100 | 40 |
| 185 | POST | 4800 | 10 | 0 | 0 | 0 | 0 | 40 | 20 | 75 |
|  | PRE | 4800 | 0 | 100 | 100 | 100 | 100 | 75 | 20 | 0 |
| 189 | POST | 1200 | 60 | 80 | 90 | 75 | 85 | 100 | 95 | 60 |
|  | PRE | 1200 | 0 | 100 | 95 | 95 | 100 | 100 | 95 | 25 |
| 191 | POST | 1200 | 50 | 80 | 70 | 70 | 95 | 100 | 100 | 10 |
|  | PRE | 1200 | 95 | 100 | 100 | 100 | 100 | 100 | 90 | 10 |
| 207 | POST | 1200 | 40 | 85 | 90 | 20 | 100 | 80 | 90 | 0 |
|  | PRE | 1200 | 40 | 60 | 95 | 60 | 50 | 100 | 50 | 10 |
| 209 | POST | 1200 | 20 | 80 | 95 | 25 | 100 | 100 | 100 | 20 |
|  | PRE | 1200 | 100 | 100 | 95 | 100 | 100 | 100 | 100 | 100 |
| 210 | POST | 1200 | 10 | 90 | 95 | 85 | 100 | 100 | 100 | 85 |
|  | PRE | 1200 | 0 | 90 | 95 | 100 | 100 | 95 | 95 | 80 |
| 212 | POST | 1200 | 20 | 40 | 10 | 10 | 0 | 75 | 70 | 25 |
|  | PRE | 1200 | 0 | 90 | 95 | 40 | 90 | 100 | 70 | 0 |
| 215 | POST | 1200 | 10 | 25 | 85 | 20 | 100 | 60 | 80 | 10 |
|  | PRE | 1200 | 0 | 40 | 90 | 50 | 90 | 10 | 0 | 0 |
| 219 | POST | 1200 | 40 | 95 | 95 | 70 | 100 | 100 | 95 | 75 |
|  | PRE | 1200 | 80 | 100 | 95 | 100 | 100 | 100 | 100 | 100 |
| 220 | POST | 1200 | 85 | 100 | 95 | 85 | 95 | 100 | 100 | 85 |
|  | PRE | 1200 | 95 | 95 | 95 | 100 | 100 | 100 | 100 | 80 |

TABLE 3C

| COMPOUND | TYPE | Gm/HA | BID | BYG | CRB | FOX | NS | SMT | VEL | RYE |
|---|---|---|---|---|---|---|---|---|---|---|
| 190 | POST | 600 | 5 | 60 | 0 | 5 | 20 | 20 | 0 | 0 |
|  | PRE | 600 | 25 | 100 | 100 | 100 | 100 | 98 | 10 | 10 |
| 199 | POST | 600 | 0 | 85 | 85 | 100 | 100 | 20 | 10 | 30 |
|  | PRE | 600 | 80 | 100 | 100 | 100 | 100 | 100 | 95 | 98 |
| 203 | POST | 600 | 0 | 0 | 0 | 0 | 20 | 10 | 5 | 0 |
|  | PRE | 600 | 0 | 15 | 90 | 10 | 0 | 0 | 0 | 0 |
| 221 | POST | 600 | 0 | 0 | 0 | 0 | 50 | 0 | 0 | 0 |
|  | PRE | 600 | 0 | 0 | 0 | 0 | 5 | 0 | 0 | 0 |
| 222 | POST | 600 | 0 | 80 | 20 | 0 | 100 | 0 | 0 | 0 |
|  | PRE | 600 | 100 | 100 | 100 | 100 | 100 | 100 | 10 | 65 |
| 223 | POST | 600 | 5 | 75 | 15 | 15 | 80 | 75 | 5 | 0 |
|  | PRE | 600 | 0 | 100 | 100 | 100 | 100 | 100 | 15 | 90 |
| 224 | POST | 600 | 5 | 75 | 90 | 95 | 100 | 85 | 5 | 80 |
|  | PRE | 600 | 25 | 99 | 100 | 98 | 99 | 25 | 15 | 15 |
| 225 | POST | 600 | 25 | 5 | 5 | 0 | 50 | 20 | 0 | 5 |
|  | PRE | 600 | 95 | 100 | 100 | 100 | 100 | 100 | 45 | 50 |
| 226 | POST | 2400 | 85 | 90 | 95 | 100 | 100 | 100 | 90 | 100 |
|  | PRE | 2400 | 75 | 100 | 100 | 100 | 100 | 100 | 90 | 100 |
| 227 | POST | 2400 | 80 | 90 | 100 | 100 | 100 | 100 | 85 | 95 |
|  | PRE | 2400 | 100 | 100 | 100 | 100 | 100 | 95 | 100 | 100 |
| 228 | POST | 2400 | 90 | 90 | 90 | 95 | 95 | 95 | 85 | 50 |
|  | PRE | 2400 | 100 | 100 | 100 | 100 | 100 | 100 | 100 | 100 |
| 229 | POST | 600 | 0 | 0 | 50 | 0 | 15 | 0 | 0 | 0 |
|  | PRE | 600 | 0 | 15 | 50 | 10 | 100 | 75 | 0 | 0 |

TABLE 3C-continued

| COMPOUND | TYPE | Gm/HA | BID | BYG | CRB | FOX | NS | SMT | VEL | RYE |
|---|---|---|---|---|---|---|---|---|---|---|
| 230 | POST | 600 | 0 | 0 | 15 | 0 | 90 | 100 | 0 | 0 |
|  | PRE | 600 | 0 | 15 | 85 | 15 | 80 | 10 | 0 | 0 |
| 231 | POST | 2400 | 0 | 0 | 0 | 0 | 15 | 0 | 0 | 0 |
|  | PRE | 2400 | 0 | 15 | 70 | 5 | 15 | 0 | 0 | 0 |
| 232 | POST | 2400 | 0 | 0 | 0 | 5 | 10 | 0 | 5 | 0 |
|  | PRE | 2400 | 0 | 0 | 20 | 0 | 70 | 0 | 0 | 0 |
| 233 | POST | 600 | 55 | 5 | 15 | 5 | 90 | 35 | 5 | 0 |
|  | PRE | 600 | 65 | 100 | 100 | 100 | 100 | 90 | 40 | 50 |
| 234 | POST | 600 | 45 | 90 | 35 | 80 | 85 | 45 | 10 | 20 |
|  | PRE | 600 | 30 | 100 | 100 | 100 | 100 | 90 | 50 | 75 |
| 235 | POST | 600 | 0 | 0 | 0 | 5 | 60 | 10 | 0 | 0 |
|  | PRE | 600 | 0 | 10 | 100 | 50 | 50 | 35 | 0 | 0 |
| 236 | POST | 600 | 0 | 75 | 65 | 5 | 90 | 98 | 0 | 35 |
|  | PRE | 600 | 100 | 95 | 100 | 100 | 100 | 80 | 5 | 99 |
| 237 | POST | 600 | 15 | 0 | 5 | 10 | 85 | 10 | 0 | 0 |
|  | PRE | 600 | 20 | 98 | 100 | 25 | 99 | 95 | 0 | 10 |
| 238 | POST | 600 | 70 | 90 | 95 | 5 | 95 | 75 | 70 | 80 |
|  | PRE | 600 | 80 | 100 | 100 | 100 | 100 | 90 | 35 | 90 |
| 239 | POST | 600 | 15 | 80 | 15 | 30 | 98 | 65 | 75 | 20 |
|  | PRE | 600 | 35 | 100 | 100 | 100 | 100 | 100 | 100 | 100 |
| 240 | POST | 600 | 0 | 45 | 55 | 5 | 90 | 80 | 25 | 20 |
|  | PRE | 600 | 90 | 90 | 100 | 100 | 100 | 100 | 100 | 80 |
| 241 | POST | 600 | 10 | 0 | 0 | 10 | 60 | 50 | 0 | 0 |
|  | PRE | 600 | 0 | 25 | 100 | 100 | 100 | 35 | 0 | 0 |
| 244 | POST | 2400 | 0 | 0 | 0 | 0 | 15 | 0 | 0 | 0 |
|  | PRE | 2400 | 100 | 0 | 20 | 0 | 25 | 0 | 0 | 0 |

We have also discovered that combinations of the compounds of the present invention with certain of the above disclosed other herbicides provide unexpectedly enhanced efficacy. Data in Tables 4–7 show this effect. These data demonstrate that the combinations are synergistic rather than additive.

TABLE 4

POSTEMERGENCE FIELD TEST DATA
% CROP INJURY OR WEED CONTROL
(28 DAYS AFTER APPLICATION)

|  | g/Ha | WHE | CW | MAT | POA | RYE | YR |
|---|---|---|---|---|---|---|---|
| Compound 46 | 150 | 0 | 57 | 13 | 17 | 20 | 13 |
|  | 300 | 0 | 72 | 27 | 37 | 47 | 28 |
|  | 600 | 0 | 95 | 43 | 97 | 93 | 83 |
| A | 1000 | 0 | 27 | 7 | 7 | 10 | 50 |
| A + 46 | 1000 + 150 | 0 | 100 | 75 | 55 | 47 | 83 |
|  | 1000 + 300 | 0 | 100 | 73 | 97 | 98 | 93 |
| B | 20 | 0 | 98 | 95 | 17 | 73 | 87 |
| B + 46 | 20 + 150 | 0 | 100 | 95 | 82 | 77 | 85 |
|  | 20 + 300 | 0 | 100 | 97 | 72 | 85 | 82 |
| UNTREATED | — | 0 | 0 | 0 | 0 | 0 | 0 |

A = N-(4-isopropylphenyl) N,N-dimethylurea
B = 62.5% 2-chloro-N-[[(4-methoxy-6-methyl-1,3,5-triazine-2-yl)amino]-carbonyl]benzenesulfonamide
12.5% methyl 2-[[[[(4-methoxy-6-methyl-1,3,5-triazin-2-yl)amino]-carobnyl]amino]-sulfonyl]benzoate.

TABLE 5

PREEMERGENCE FIELD TEST DATA
% CROP INJURY OR WEED CONTROL
(28 DAYS AFTER APPLICATION)

|  | g/Ha | WHE | BAR | OAT |
|---|---|---|---|---|
| Compound 46 | 150 | 5 | 8 | 33 |
|  | 300 | 25 | 33 | 93 |
|  | 600 | 67 | 78 | 100 |
| B | 20 | 0 | 0 | 0 |

TABLE 5-continued

PREEMERGENCE FIELD TEST DATA
% CROP INJURY OR WEED CONTROL
(28 DAYS AFTER APPLICATION)

|  | g/Ha | WHE | BAR | OAT |
|---|---|---|---|---|
|  | 35 | 0 | 7 | 5 |
| B + 46 | 20 + 150 | 7 | 18 | 67 |
|  | 20 + 300 | 23 | 33 | 88 |
| UNTREATED | — | 0 | 0 | 0 |

TABLE 6

POSTEMERGENCE FIELD TEST DATA
% CROP INJURY OR WEED CONTROL
(28 DAYS AFTER APPLICATION)

|  | g/Ha | WHE | BAR | OAT | RYE |
|---|---|---|---|---|---|
| Compound 153 | 150 | 0 | 0 | 48 | 82 |
|  | 300 | 13 | 13 | 60 | 93 |
|  | 600 | 27 | 30 | 85 | 100 |
| A | 600 | 0 | 0 | 43 | 90 |
|  | 1200 | 0 | 0 | 87 | 100 |
| A + 153 | 150 + 600 | 0 | 0 | 75 | 100 |
| UNTREATED | — | 0 | 0 | 0 | 0 |

TABLE 7

POSTEMERGENCE GREENHOUSE DATA
% CROP INJURY OR WEEK CONTROL
(14 DAYS AFIFER APPLICATION)
TEST I

|  | g/Ha | RI | BYG |
|---|---|---|---|
| Compound 46 | 38 | 0 | 5 |
|  | 75 | 0 | 20 |
|  | 150 | 0 | 35 |
|  | 300 | 0 | 50 |
| C | 600 | 0 | 0 |
| C + 46 | 600 + 38 | 0 | 35 |

TABLE 7-continued

|   |   |   |   |
|---|---|---|---|
|   | 600 + 75 | 0 | 78 |
|   | 600 + 150 | 0 | 88 |
| C | 1200 | 0 | 73 |
| C + 46 | 1200 + 38 | 0 | 100 |
|   | 1200 + 75 | 3 | 100 |
|   | 1200 + 150 | 8 | 100 |
| C | 2400 | 0 | 100 |
| C + 46 | 2400 + 38 | 0 | 100 |
|   | 2400 + 75 | 8 | 100 |
|   | 2400 + 150 | 18 | 100 |
| UNTREATED | — | 0 | 0 |

TEST II

|   | g/Ha | RI | BYG | SIG | SPR | MG | CFW |
|---|---|---|---|---|---|---|---|
| 46 | 38 | 0 | 20 | 0 | 0 | 35 | 5 |
|   | 75 | 0 | 13 | 30 | 48 | 18 | 0 |
|   | 150 | 0 | 35 | 38 | 60 | 65 | 30 |
|   | 300 | 18 | 38 | 60 | 85 | 65 | 43 |
| C | 600 | 0 | 0 | 85 | 0 | 60 | 100 |
| C + 46 | 600 + 38 | 0 | 30 | 80 | 0 | 68 | 75 |
|   | 600 + 75 | 0 | 40 | 80 | 28 | 90 | 100 |
|   | 600 + 150 | 10 | 70 | 100 | 75 | 75 | 100 |
| C | 1200 | 0 | 23 | 100 | 30 | 70 | 100 |
| C + 46 | 1200 + 38 | 0 | 38 | 100 | 43 | 93 | 100 |
|   | 1200 + 75 | 0 | 43 | 100 | 60 | 100 | 100 |
|   | 1200 + 150 | 10 | 70 | 100 | 83 | 100 | 100 |
| C | 2400 | 0 | 65 | 100 | 50 | 100 | 100 |
| C + 46 | 2400 + 38 | 0 | 43 | 100 | 75 | 100 | 100 |
|   | 2400 + 75 | 0 | 78 | 100 | 93 | 100 | 100 |
|   | 2400 + 150 | 10 | 100 | 100 | 98 | 100 | 100 |
| UN-TREAT-ED | — | 0 | 0 | 0 | 0 | 0 | 0 |

C = N-(3,4-dichlorophenyl-propionamide)

Other herbicides which, in combination with compounds of the present invention, result in enhanced efficacy include phenyl substituted ureas, benzenesulfonyl substituted ureas, and N-(3,4-dichlorophenyl)propionamide. Preferred phenyl substituted ureas and benzenesulfonyl substituted ureas are 2-chloro-N-[[(4-methoxy-6-methyl-1,3,5-triazin-2-yl)amino]carbonyl]-benzenesulfonamide, N-(4-isopropylphenyl)-N,N-dimethylurea, and methyl 2-[[[[(4-methoxy-6-methyl-1,3,5-triazin-2-yl)amino]-carbonyl]amino]-sulfonyl]benzoate. Preferred compounds of the present invention are 5-ethyl-2-phenyl-3-propargyl-6-trifluoromethyl-4(3H)-pyrimidinone and 6-difluoromethyl-5-ethyl-2-phenyl-3-propargyl-4(3H)-pyrmidinone.

It is to be understood that changes and variations may be made without departing from the spirit and scope of the invention as defined by the appended claims.

We claim:

1. A method of controlling a weed comprising applying a herbicidally effective amount of a composition comprising a compound of the formula

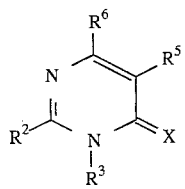

wherein (a) $R^2$ is a furyl, phenyl, naphthyl pyridyl, or thienyl group, each of said group is optionally substituted with up to three substituents independently selected from a bromo, chloro, fluoro, $(C_1-C_{12})$alkyl, cyclo$(C_3$-$C_8)$alkyl, $(C_2$-$C_{12})$alkenyl, cyclo$(C_3$-$C_8)$alkenyl, $(C_2$-$C_{12})$alkynyl, halo$(C_1$-$C_{12})$alkyl, polyhalo$(C_1$-$C_{12})$alkyl, halo$(C_2$-$C_{12})$alkenyl, polyhalo$(C_2$-$C_{12})$alkenyl, halo$(C_2$-$C_6)$alkynyl, polyhalo$(C_2$-$C_6)$alkynyl, $(C_1$-$C_{12})$alkoxy, $(C_1$-$C_{12})$alkylthio, $(C_1$-$C_{12})$alkylsulfonyl, $(C_1$-$C_{12})$alkylsulfinyl, phenyl, phen$(C_1$-$C_{12})$alkyl, phen$(C_2$-$C_{12})$alkenyl, phen$(C_2$-$C_{12})$alkynyl, cyano, halo$(C_1$-$C_{12})$alkoxy, 1,3-dioxolan-2-yl, hydroxyimino, or nitro group; and when $R^2$ is pyridyl, such pyridyl group is optionally substituted with oxygen on the nitrogen of the pyridyl group; or $R^2$ is a furyl, phenyl, naphthyl, pyridyl or thienyl group having a fused ring moiety composed of an oxymethyleneoxy or an oxoethyleneoxy link bonds to adjacent carbon atoms or said group:

(b) $R^3$ is a $(C_1-C_3)$alkyl, $(C_3-C_4)$alkenyl, $(C_5-C_6)$alkenynyl, $(C_3-C_6)$alkynyl, $(C_1-C_6)$alkoxy$(C_1-C_6)$alkyl, di$(C_1-C_6)$alkoxy$(C_1-C_6)$alkyl, (halo$(C_1-C_6)$alkoxy$(C_1-C_6)$alkyl, 2-oxo$(C_2-C_3)$alkyl, trimethylsilyl$(C_3-C_4)$alkynyl, cyano$(C_1-C_6)$alkyl, or phenyl group, each of said $(C_1-C_3)$alkyl, $(C_3-C_4)$alkenyl, or $(C_3-C_6)$alkynyl group is optionally substituted with up to five halogens;

(c) $R^5$ is $(C_1-C_6)$acyl, $(C_1-C_6)$alkoxy$(C_1-C_6)$alkyl, $(C_1-C_6)$alkoxyimino, di$(C_1-C_6)$alkoxy$(C_1-C_6)$alkyl, formyl, hydroxy$(C_1-C_6)$alkyl, or hydroxyimino;

(d) $R^6$ is a hydrogen, halo, $(C_1-C_8)$alkyl, $(C_2-C_6)$alkenyl, $(C_2-C_6)$alkynyl, halo$(C_1-C_6)$alkyl, polyhalo$(C_1-C_6)$alkyl, halo$(C_2-C_6)$alkenyl, polyhalo$(C_2-C_6)$alkenyl, halo$(C_2-C_6)$alkynyl, polyhalo$(C_2-C_6)$alkynyl, $(C_1-C_6)$alkoxy, $(C_1-C_6)$alkoxy$(C_1-C_4)$alkyl, $(C_1-C_6)$alkylthio, $(C_1-C_3)$alkoxycarbonyl, $(C_1-C_3)$alkoxycarbonyl$(C_1-C_3)$alkyl, $(C_6-C_{10})$aryl, ar$(C_1-C_4)$alkyl, cyclo$(C_3-C_7)$alkyl, $(C_4-C_5)$heterocyclyl selected from a group consisting of furyl, thienyl, or pyridyl, $(C_1-C_3)$alkylamino, di$(C_1-C_3)$alkylamino, di$(C_1-C_3)$alkylaminocarbonyl, halo$(C_1-C_6)$alkylthio, polyhalo$(C_1-C_6)$alkylthio, halo$(C_1-C_6)$alkoxy, polyhalo$(C_1-C_6)$alkoxy, $(C_6-C_{10})$aryloxy or cyano group; said $(C_6-C_{10})$aryl, ar$(C_1-C_4)$alkyl and $(C_6-C_{10})$aryloxy groups being optionally substituted with up to three substituents independently selected from bromo; chloro; fluoro; $(C_1-C_{12})$alkyl, cyclo$(C_3-C_8)$alkyl, $(C_2-C_{12})$alkenyl, cyclo$(C_3-C_8)$alkenyl, $(C_2-C_{12})$alkynyl, halo$(C_1-C_{12})$alkyl, polyhalo$(C_1-C_{12})$alkyl, halo$(C_2-C_{12})$alkenyl, polyhalo$(C_2-C_{12})$alkenyl, halo$(C_2-C_6)$alkynyl, polyhalo$(C_2-C_6)$alkynyl; $(C_1-C_{12})$alkoxy, $(C_1-C_{12})$alkylthio, $(C_1-C_{12})$alkylsulfonyl, $(C_1-C_{12})$alkylsulfinyl, phenyl, phen$(C_1-C_{12})$alkyl, phen$(C_2-C_{12})$alkenyl, phen$(C_2-C_{12})$alkynyl, cyano, halo$(C_1-C_{12})$alkoxy, 1,3-dioxalan-2-yl, hydroxyimino, and nitro; and (e) X is oxygen or sulfur to said weed or to the locus of said weed or to the growth medium of said weed.

2. A herbicidal composition, comprising:

(i) a compound of the formula

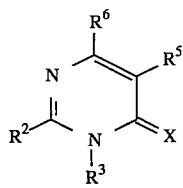

wherein (a) $R^2$ is a furyl, phenyl, naphthyl, pyridyl, or thienyl group, each of said group is optionally substituted with up to three substituents independently selected from a bromo, chloro, fluoro, $(C_1-C_{12})$alkyl, cyclo$(C_3-C_8)$alkyl, $(C_2-C_{12})$alkenyl, cyclo$(C_3-C_8)$alkenyl, $(C_2-C_{12})$alkynyl, halo$(C_1-C_{12})$alkyl, polyhalo$(C_1-C_{12})$alkyl, halo$(C_2-C_{12})$alkenyl, polyhalo$(C_2-C_{12})$alkenyl, halo$(C_2-C_6)$alkynyl, polyhalo$(C_2-C_6)$alkynyl, $(C_1-C_{12})$alkoxy, $(C_1-C_{12})$alkylthio, $(C_1-C_{12})$alkylsulfonyl, $(C_1-C_{12})$alkylsulfinyl, phenyl, phen$(C_1-C_{12})$alkyl, phen$(C_2-C_{12})$alkenyl, phen$(C_2-C_{12})$alkynyl, cyano, halo$(C_1-C_{12})$alkoxy, 1,3-dioxolan-2-yl, hydroxyimino, or nitro group; and when $R^2$ is pyridyl, such pyridyl group is optionally substituted with oxygen on the nitrogen of the pyridyl group; or $R^2$ is a furyl, phenyl, naphthyl, pyridyl or thienyl group having a fused ring moiety composed of an oxymethyleneoxy or an oxoethyleneoxy link bonds to adjacent carbon atoms or said group;

(b) $R^3$ is a $(C_1-C_3)$alkyl, $(C_3-C_4)$alkenyl, $(C_5-C_6)$alkenynyl, $(C_3-C_6)$alkynyl, $(C_1-C_6)$alkoxy$(C_1-C_6)$alkyl, di$(C_1-C_6)$alkoxy$(C_1-C_6)$alkyl, (halo$(C_1-C_6)$alkoxy$(C_1-C_6)$alkyl, 2-oxo$(C_2-C_3)$alkyl, trimethylsilyl$(C_3-C_4)$alkynyl, cyano$(C_1-C_6)$alkyl, or phenyl group, each of said $(C_1-C_3)$alkyl, $(C_3-C_4)$alkenyl, or $(C_3-C_6)$alkynyl, group is optionally substituted with up to five halogens;

(c) $R^5$ is a hydrogen, $(C_1-C_5)$alkyl, $(C_3-C_6)$alkenyl, $(C_2-C_6)$alkynyl, halo$(C_1-C_6)$alkyl, polyhalo$(C_1-C_6)$alkyl, halo$(C_2-C_6)$alkenyl, polyhalo$(C_2-C_6)$alkenyl, halo$(C_2-C_6)$alkynyl, polyhalo$(C_2-C_6)$alkynyl, halo$(C_1-C_6)$alkoxy, polyhalo$(C_1-C_6)$alkoxy, trimethylsilyl$(C_2-C_3)$alkynyl, $(C_1-C_6)$alkoxy, $(C_1-C_6)$alkylthio, $(C_1-C_3)$alkoxycarbonyl$(C_1-C_3)$alkyl, halo, cyano, $(C_1-C_6)$acyl, $(C_1-C_6)$alkoxy$(C_1-C_6)$alkyl, $(C_1-C_6)$alkoxyimino, di$(C_1-C_6)$alkoxy$(C_1-C_6)$alkyl, formyl, hydroxy$(C_1-C_6)$alkyl, or hydroxyimino;

(d) $R^6$ is a hydrogen, halo, $(C_1-C_8)$alkyl, $(C_2-C_6)$alkenyl, $(C_2-C_6)$alkynyl, halo$(C_1-C_6)$alkyl, polyhalo$(C_1-C_6)$alkyl, halo$(C_2-C_6)$alkenyl, polyhalo$(C_2-C_6)$alkenyl, halo$(C_2-C_6)$alkynyl, polyhalo$(C_2-C_6)$alkynyl, $(C_1-C_6)$alkoxy, $(C_1-C_6)$alkoxy$(C_1-C_4)$alkyl, $(C_1-C_6)$alkylthio, $(C_1-C_3)$alkoxycarbonyl, $(C_1-C_3)$alkoxycarbonyl$(C_1-C_3)$alkyl, $(C_6-C_{10})$aryl, ar$(C_1-C_4)$alkyl, cyclo$(C_3-C_7)$alkyl, $(C_4-C_5)$heterocyclyl selected from a group consisting of furyl, thienyl or pyridyl, $(C_1-C_3)$alkylamino, di$(C_1-C_3)$alkylamino, di$(C_1-C_3)$alkylaminocarbonyl, halo$(C_1-C_6)$alkylthio, polyhalo$(C_1-C_6)$alkylthio, halo$(C_1-C_6)$alkoxy, polyhalo$(C_1-C_6)$alkoxy, $(C_6-C_{10})$aryloxy or cyano group; said $(C_6-C_{10})$aryl, ar$(C_1-C_4)$alkyl and $(C_6-C_{10})$aryloxy groups being optionally substituted with up to three substituents independently selected from bromo; chloro; fluoro; $(C_1-C_{12})$alkyl, cyclo$(C_3-C_8)$alkyl, $(C_2-C_{12})$alkenyl, cyclo$(C_3-C_8)$alkenyl, $(C_2-C_{12})$alkynyl, halo$(C_1-C_{12})$alkyl, polyhalo$(C_1-C_{12})$alkyl, halo$(C_2-C_{12})$alkenyl, polyhalo$(C_2-C_{12})$alkenyl, halo$(C_2-C_6)$alkynyl, polyhalo$(C_2-C_6)$alkynyl; $(C_1-C_{12})$alkoxy, $(C_1-C_{12})$alkylthio, $(C_1-C_{12})$alkylsulfonyl, $(C_1-C_{12})$alkylsulfinyl, phenyl phen$(C_1-C_{12})$alkyl, phen$(C_2-C_{12})$alkenyl, phen$(C_2-C_{12})$alkynyl, cyano, halo$(C_1-C_{12})$alkoxy, 1,3-dioxalan-2-yl, hydroxyimino, and nitro; and (c) X is oxygen or sulfur; and (ii) at least one herbicide selected from phenyl substituted ureas, benzenesulfonyl substituted ureas, and N-(3,4-dichlorophenyl)propionamide.

3. The herbicidal composition of claim 2 wherein the compound from group (i) of the formula:

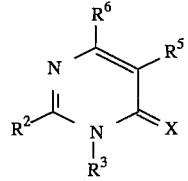

is selected from 5-ethyl-2-phenyl-3-propargyl-6-trifluoromethyl-4(3H)-pyrimidinone and 6-difluoromethyl-5-ethyl-2-phenyl-3-propargyl-4(3H)-pyrimidinone and the herbicide from group (ii) is selected from N-(4-isopropylphenyl)-N,N-dimethylurea, 2-chloro-N-(((4-methoxy-6-methyl-1,3,5-triazin-2-yl)amino)carbonyl)-benzenesulfonamide, methyl 2-(((((4-methoxy-6-methyl-1,3,5-triazin-2-yl)amino)carbonyl)amino)sulfonyl)benzoate, and N-(3,4dichlorophenyl)propionamide.

* * * * *